United States Patent [19]

Nakata et al.

[11] Patent Number: 5,046,847
[45] Date of Patent: Sep. 10, 1991

[54] METHOD FOR DETECTING FOREIGN MATTER AND DEVICE FOR REALIZING SAME

[75] Inventors: Toshihiko Nakata; Nobuyuki Akiyama; Yoshihiko Yamuchi; Mitsuyoshi Koizumi; Yoshimasa Oshima, all of Yokohama, Japan

[73] Assignee: Hitachi Ltd., Tokyo, Japan

[21] Appl. No.: 262,573

[22] Filed: Oct. 25, 1988

[30] Foreign Application Priority Data

Oct. 30, 1987 [JP] Japan ................. 62-272958
Dec. 11, 1987 [JP] Japan ................. 62-311904
Feb. 26, 1988 [JP] Japan ................. 63-42001

[51] Int. Cl.$^5$ ................................. G01N 21/00
[52] U.S. Cl. ......................... 356/338; 356/237; 356/430; 250/572
[58] Field of Search ............... 356/337–340, 356/343, 237; 250/563, 572, 205, 201; 358/199, 200

[56] References Cited

U.S. PATENT DOCUMENTS

| 4,376,951 | 3/1983 | Miyazawa | 356/430 |
| 4,433,235 | 2/1984 | Akiyama et al. | 250/205 |
| 4,610,541 | 9/1986 | Tanimoto et al. | 250/563 |
| 4,614,427 | 9/1986 | Koizumi et al. | 356/237 |
| 4,740,079 | 4/1988 | Koizumi et al. | 356/237 |
| 4,814,596 | 3/1989 | Koizumi et al. | 356/401 |

Primary Examiner—Richard A. Rosenberger
Assistant Examiner—Hoa Pham
Attorney, Agent, or Firm—Fay, Sharpe, Beall, Fagan, Minnich & McKee

[57] ABSTRACT

A method and apparatus for detecting foreign matter on a sample by illuminating a stripe-shaped region with linearly polarized light. Some of the light reflected by the sample is intercepted by a light intercepting stage, and the rest of the light reflected by the sample, which passes through the light intercepting stage is directed to a detecting optical system, to be detected by a photodetector. The sample is illuminated obliquely at a predetermined angle with respect to a group of straight lines constituting a primary pattern on the sample. The angle is selected so that the diffraction light reflected by the group of straight lines does not enter the detecting optical system. A polarizing spatial filter using a liquid crystal element may be disposed in a predetermined restricted region in a spacial frequency region, or Fourier transformation plane, within the detecting optical system. The light scattered by the sample may further be separated in the detecting optical system into partial beams having different wave orientation characteristics, which characteristics are detected by a number of one-dimensional solid state imaging elements. The signals are processed by a driver, adder, and quantizer in synchronism with the one-dimensional solid state imaging elements.

33 Claims, 35 Drawing Sheets

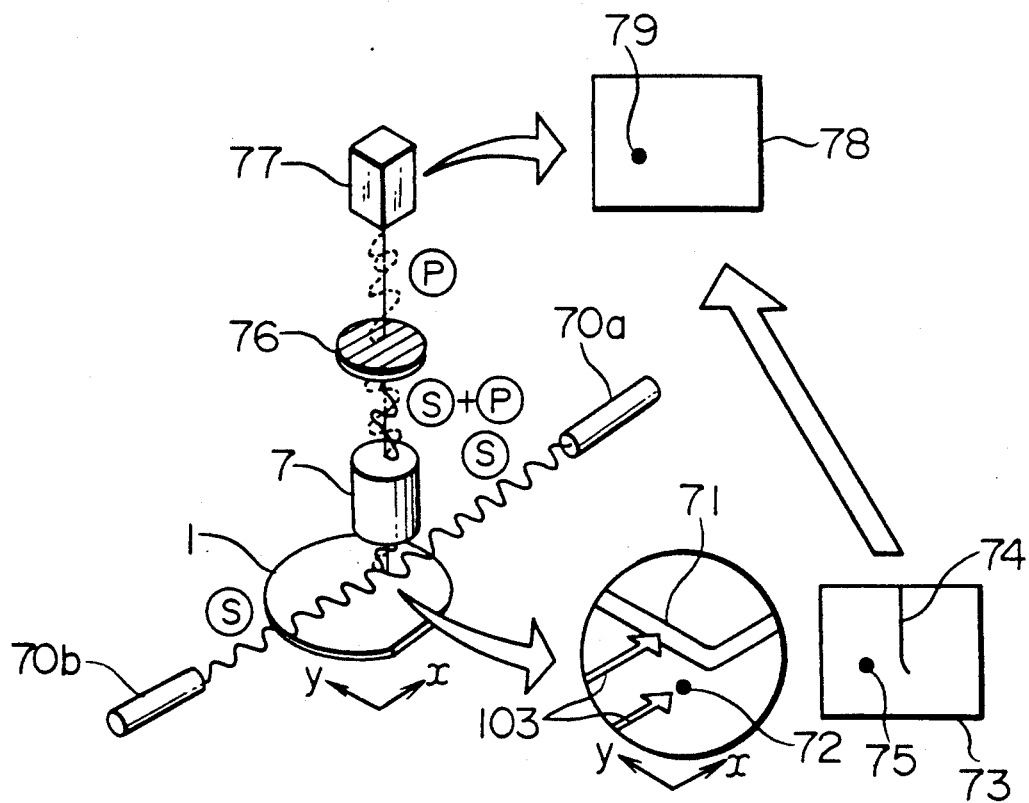
FIG. 5 PRIOR ART
FIG. 6A
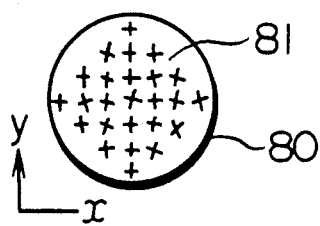
FIG. 6B
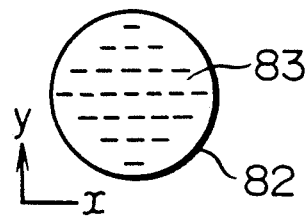
FIG. 7 PRIOR ART
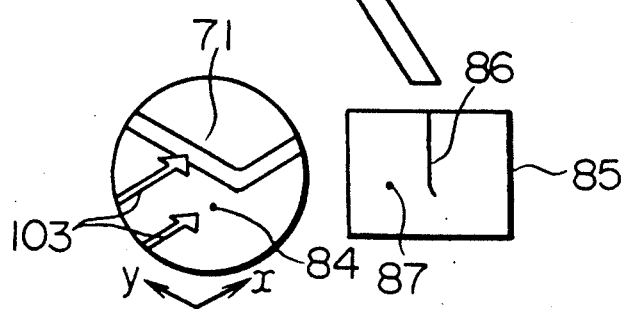

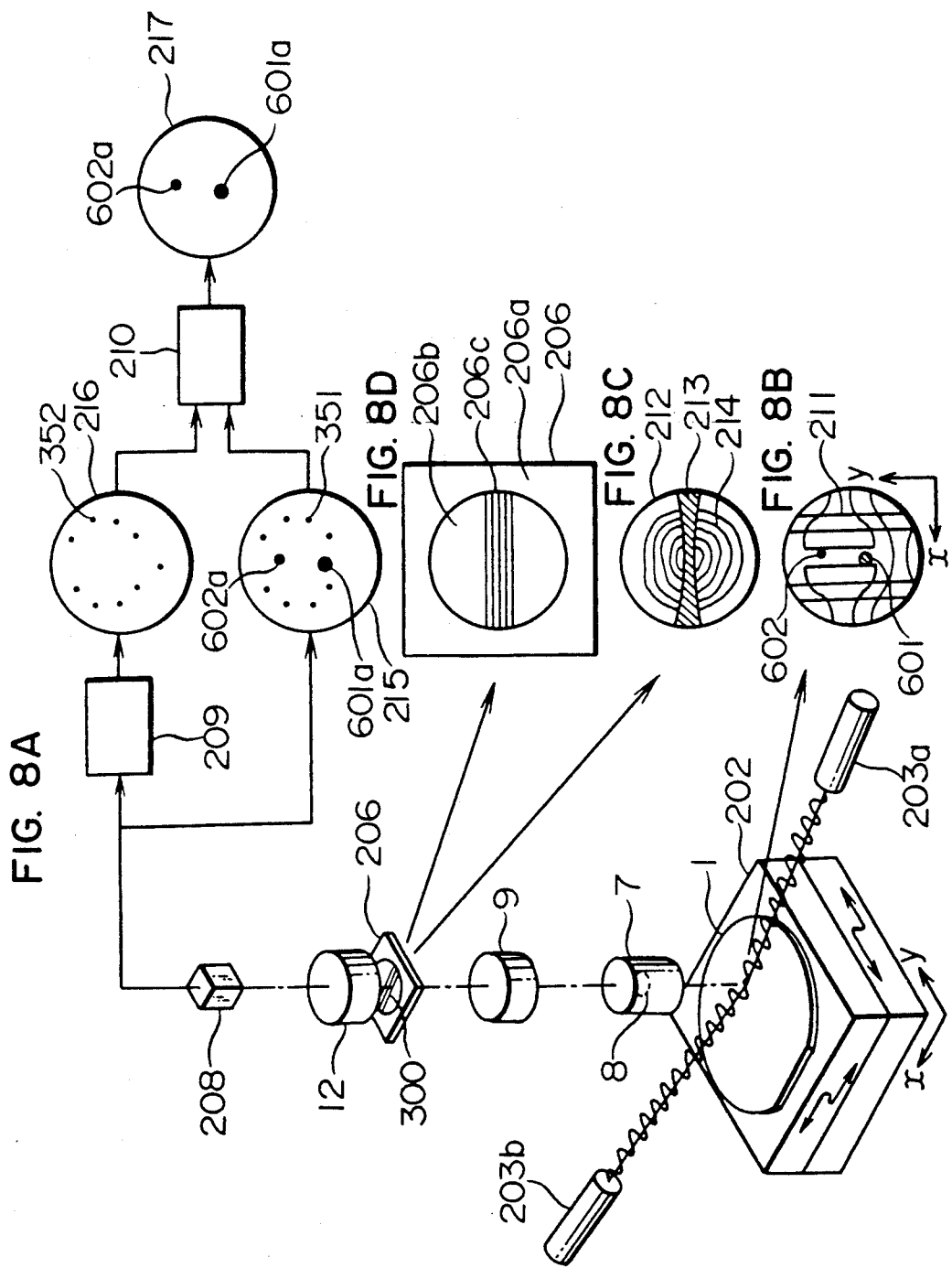

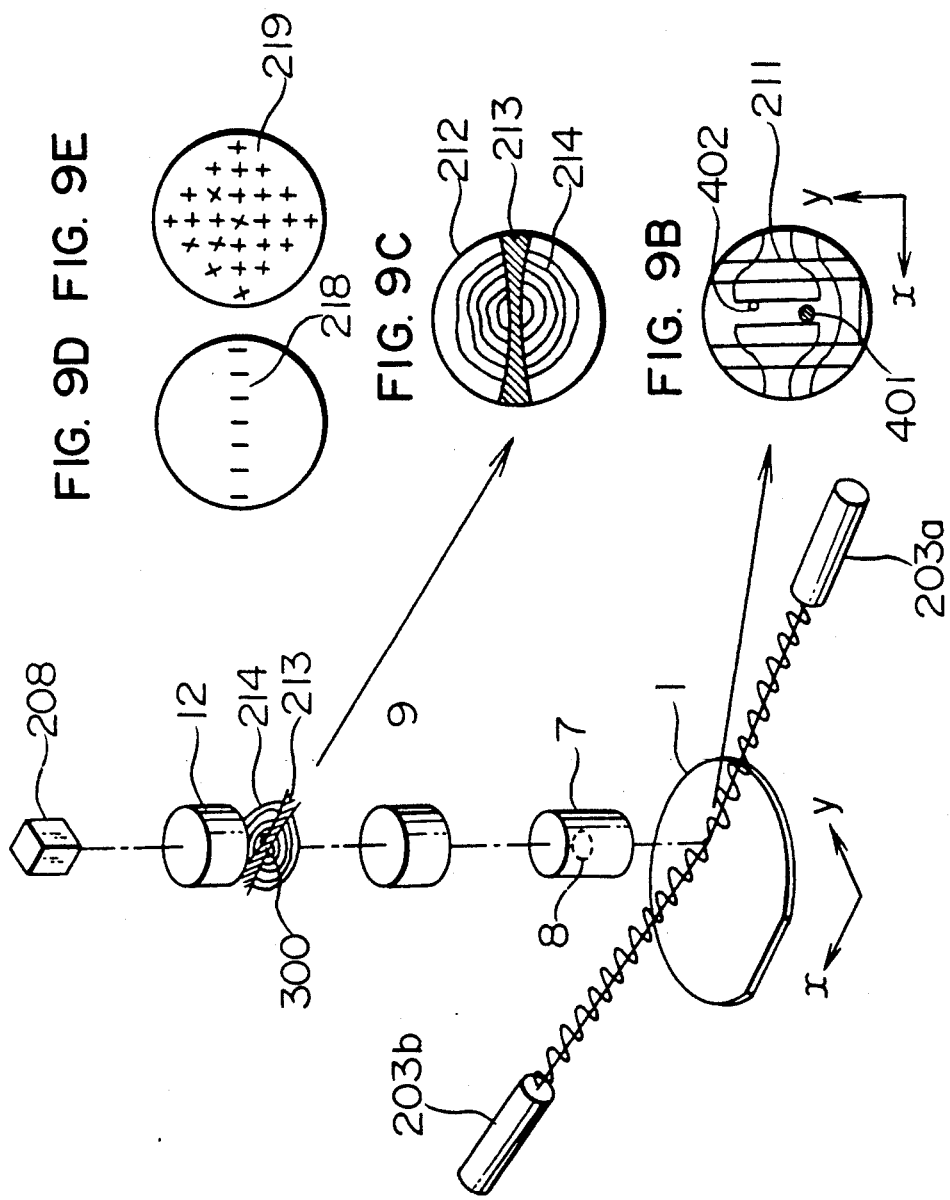

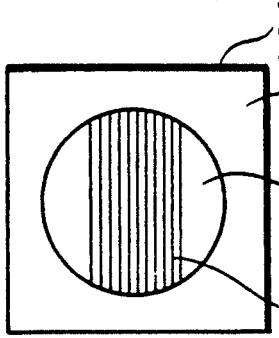
FIG. 11C
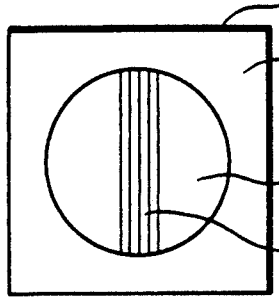
FIG. 11A
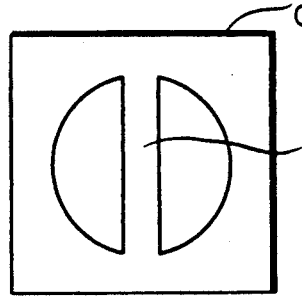
FIG. 10E
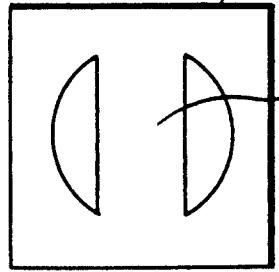
FIG. 10C
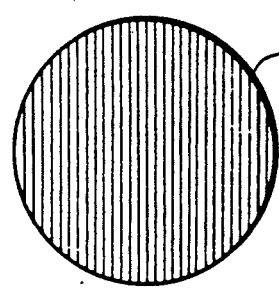
FIG. 10A
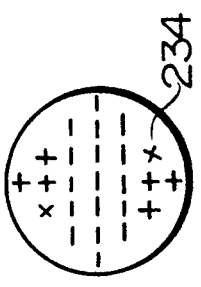
FIG. 11D
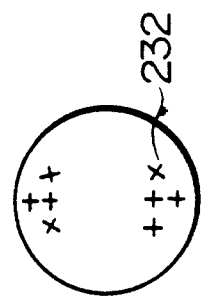
FIG. 11B
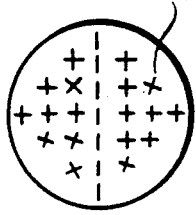
FIG. 10F
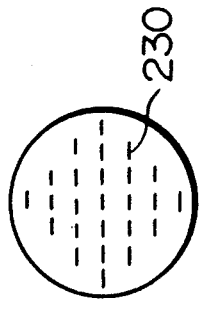
FIG. 10D
FIG. 10B

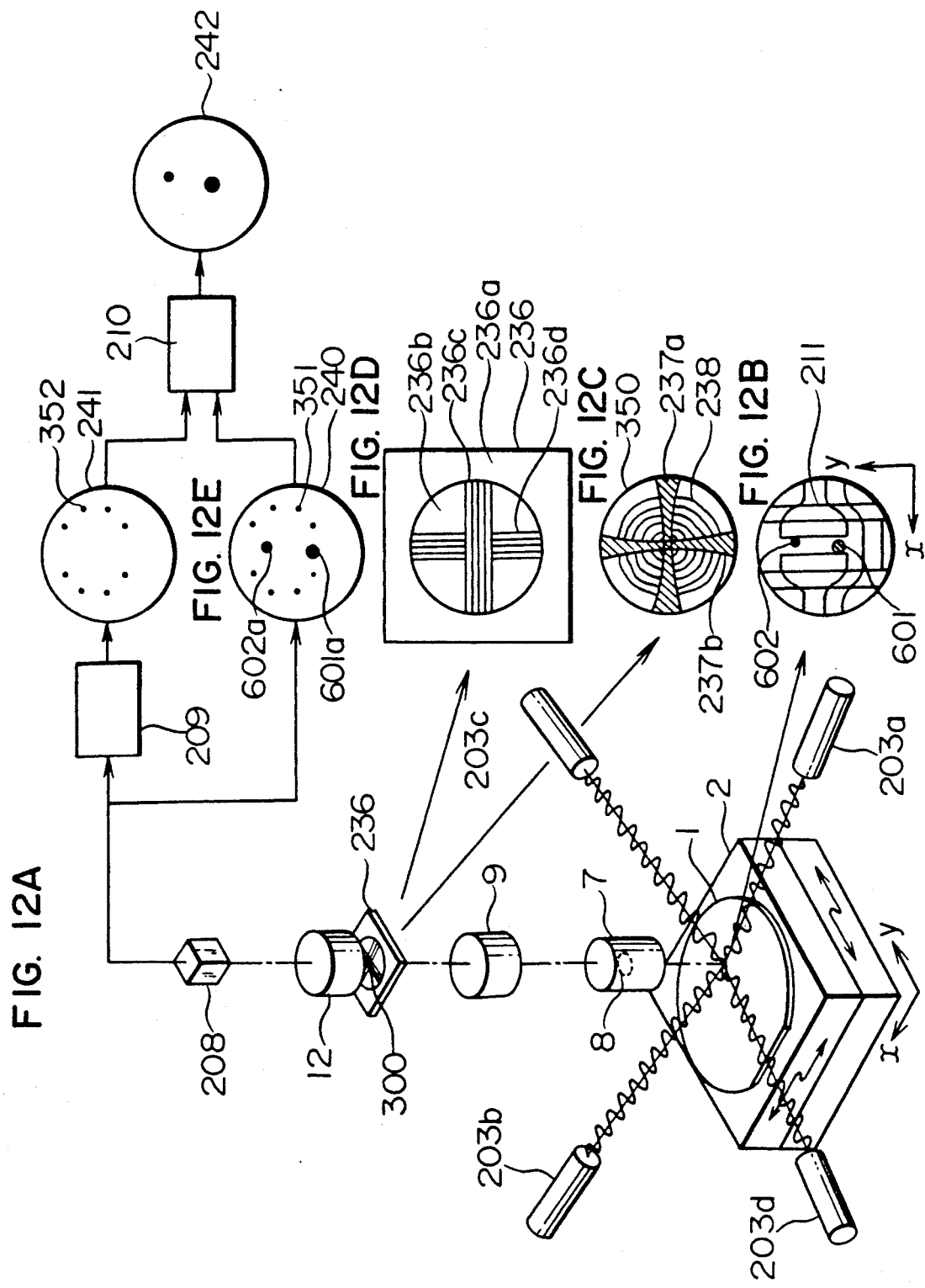

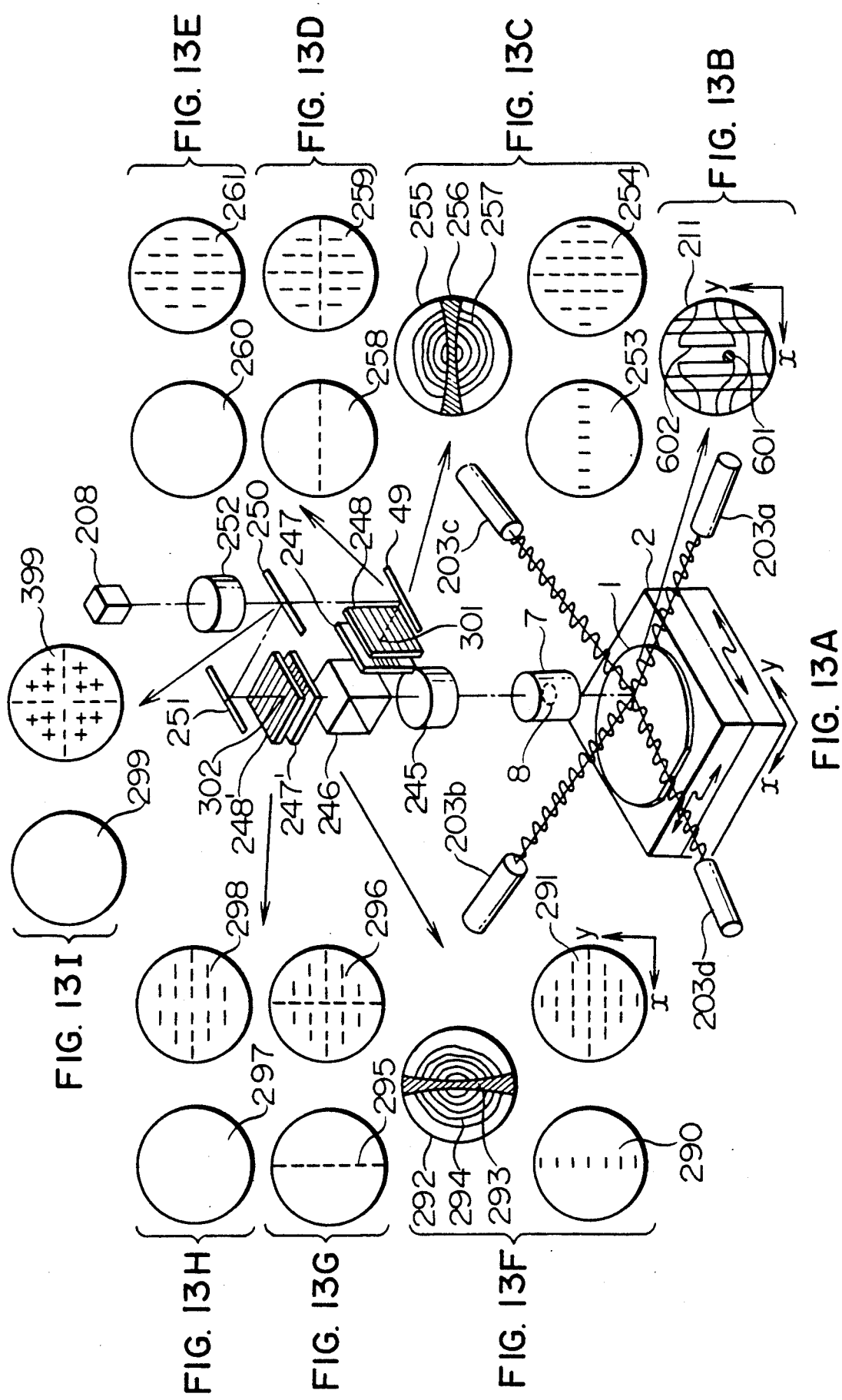

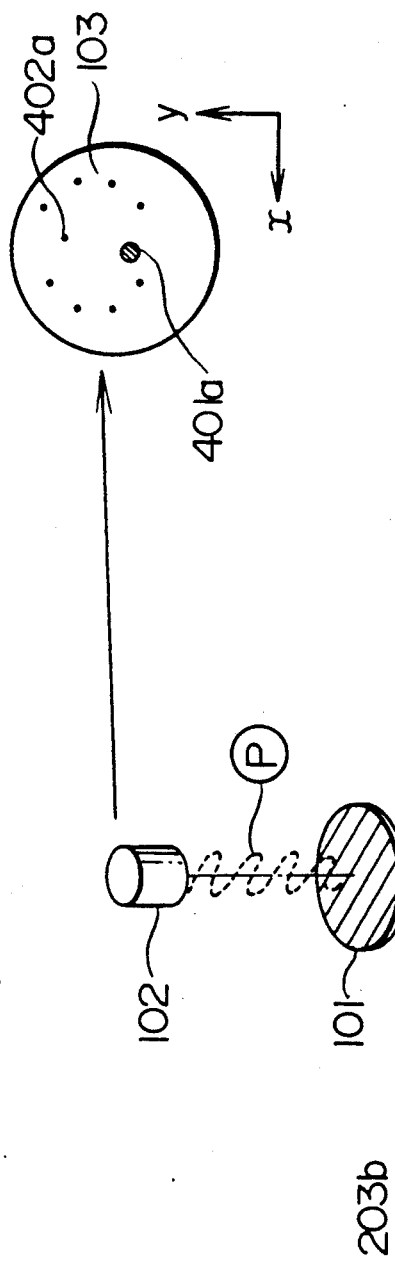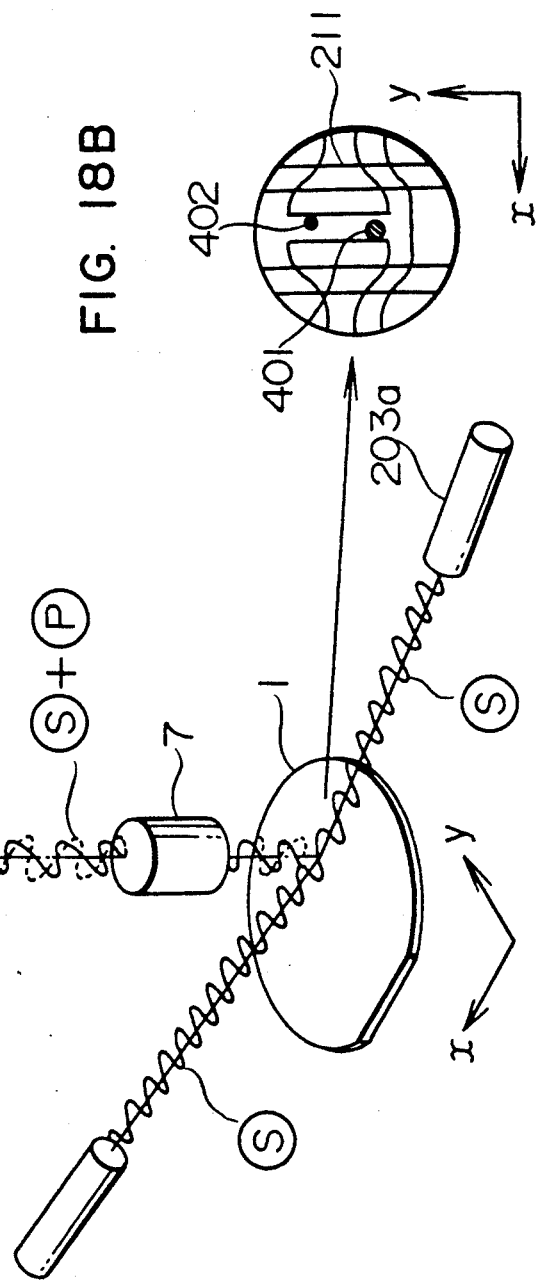

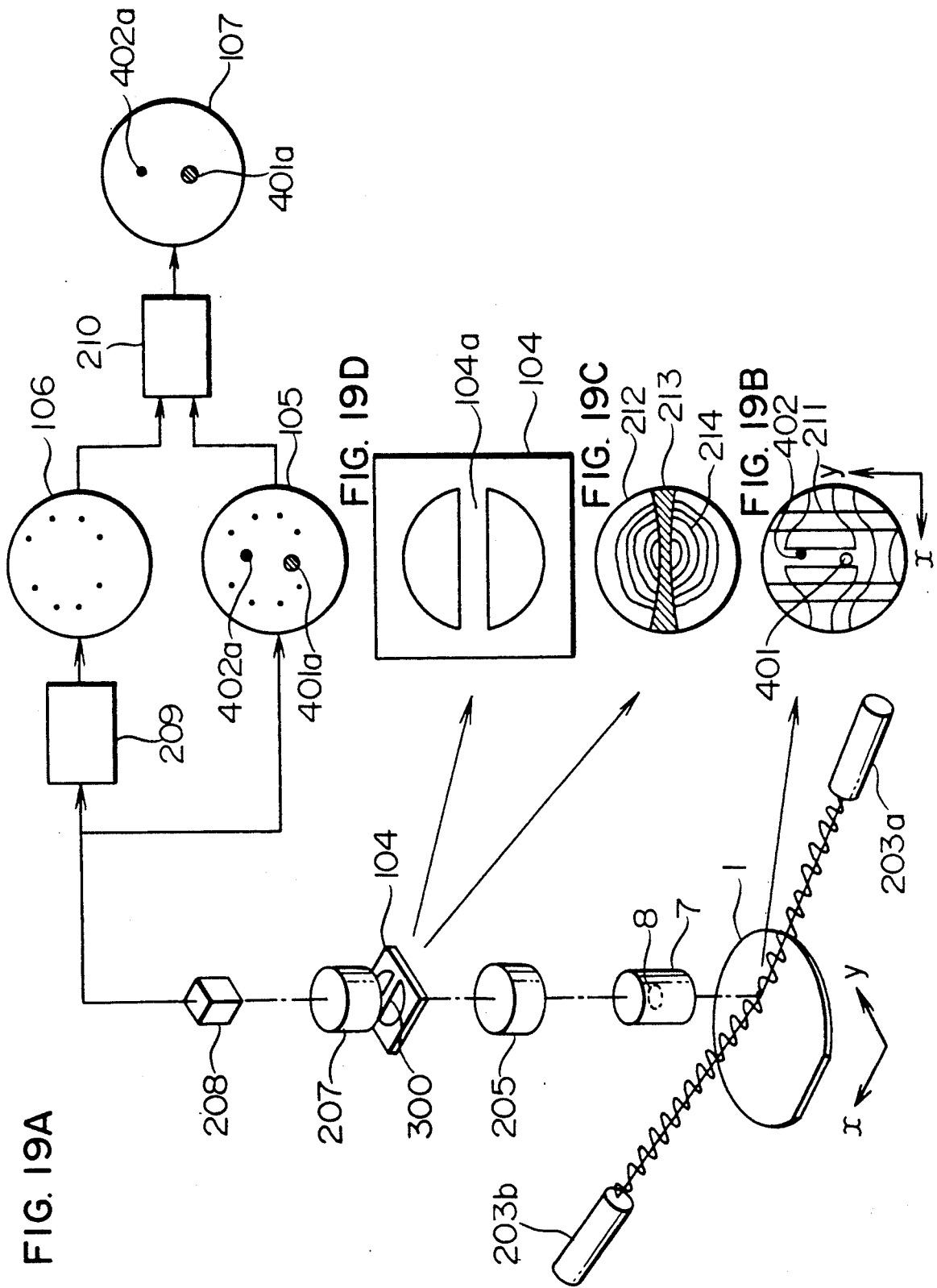

FIG. 22A     FIG. 22B
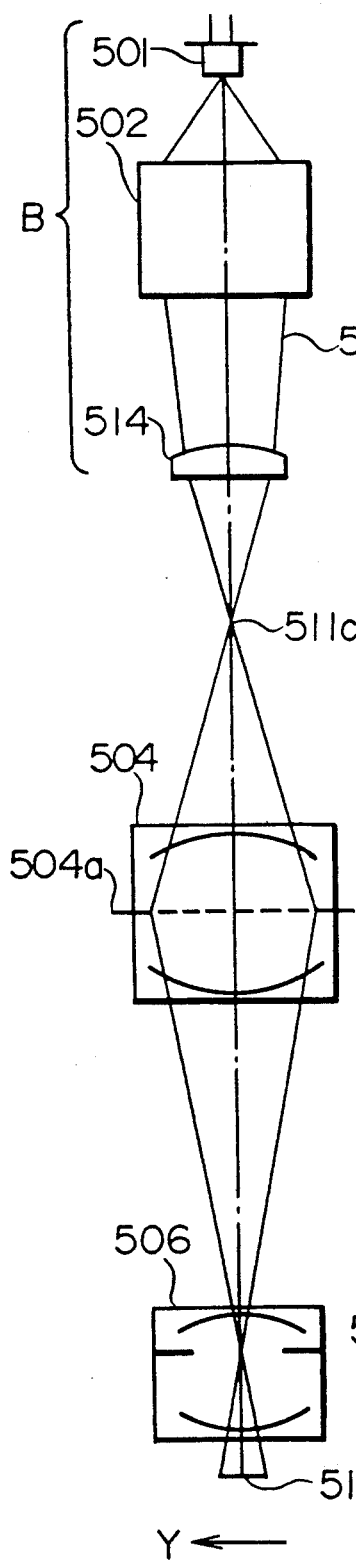
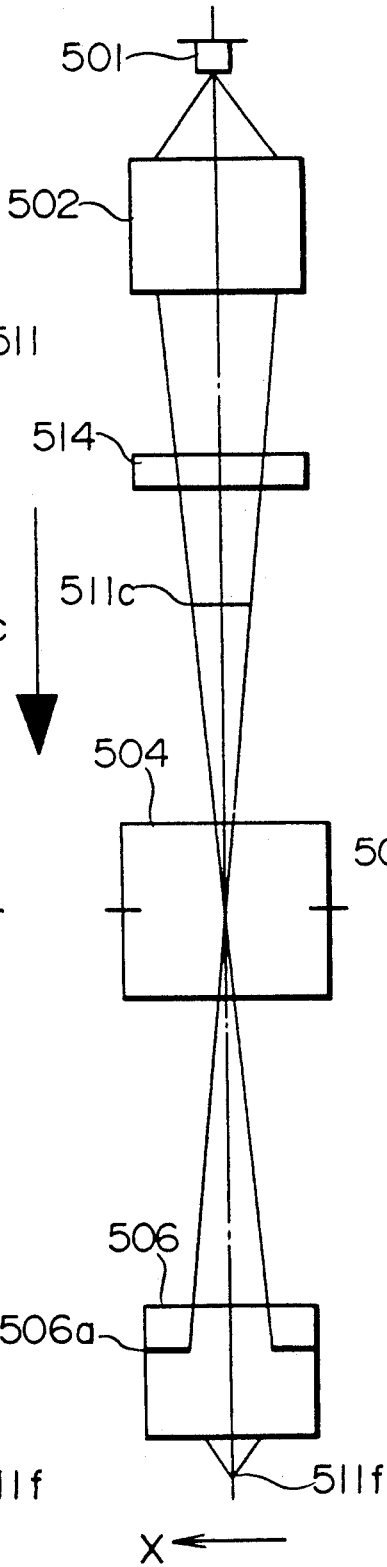
FIG. 22C
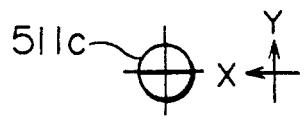
FIG. 22D
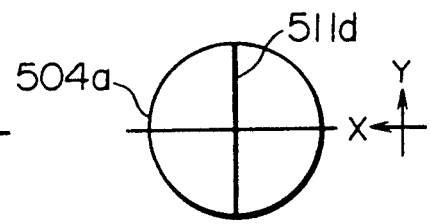
FIG. 22E
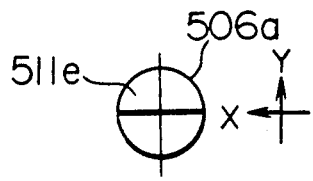
FIG. 22F
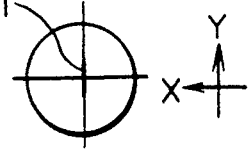

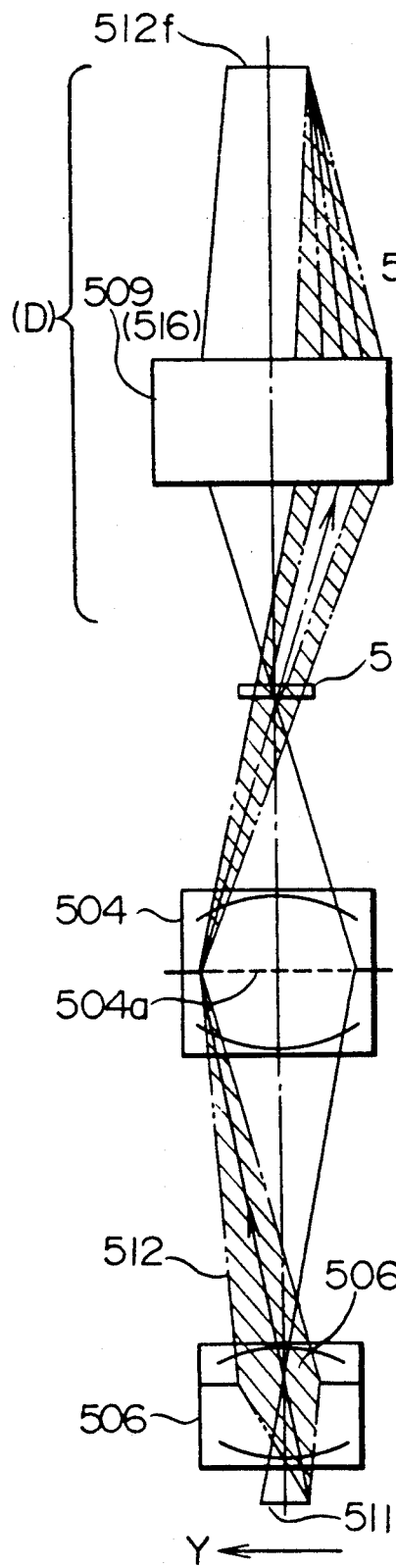
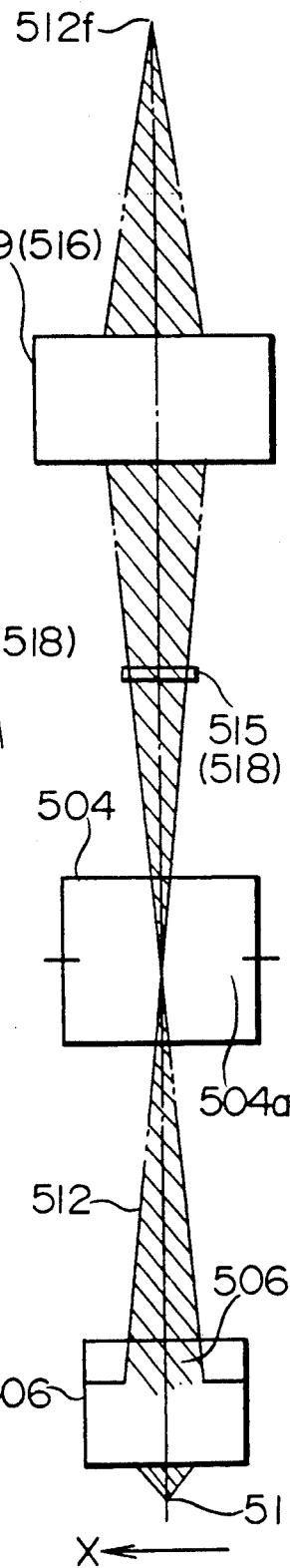
FIG. 23A  FIG. 23B  FIG. 23C
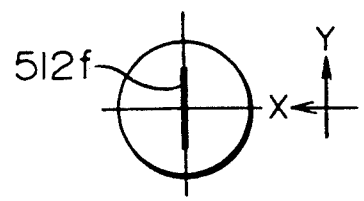
FIG. 23D
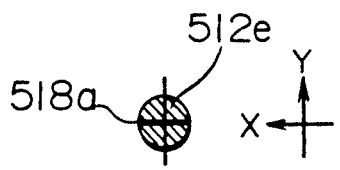
FIG. 23E
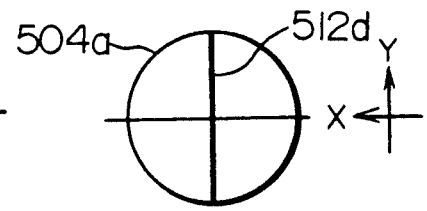
FIG. 23F
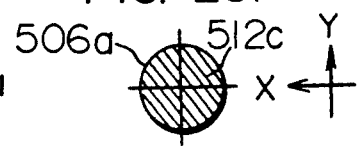
FIG. 23G
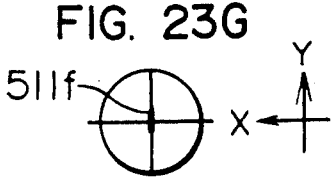

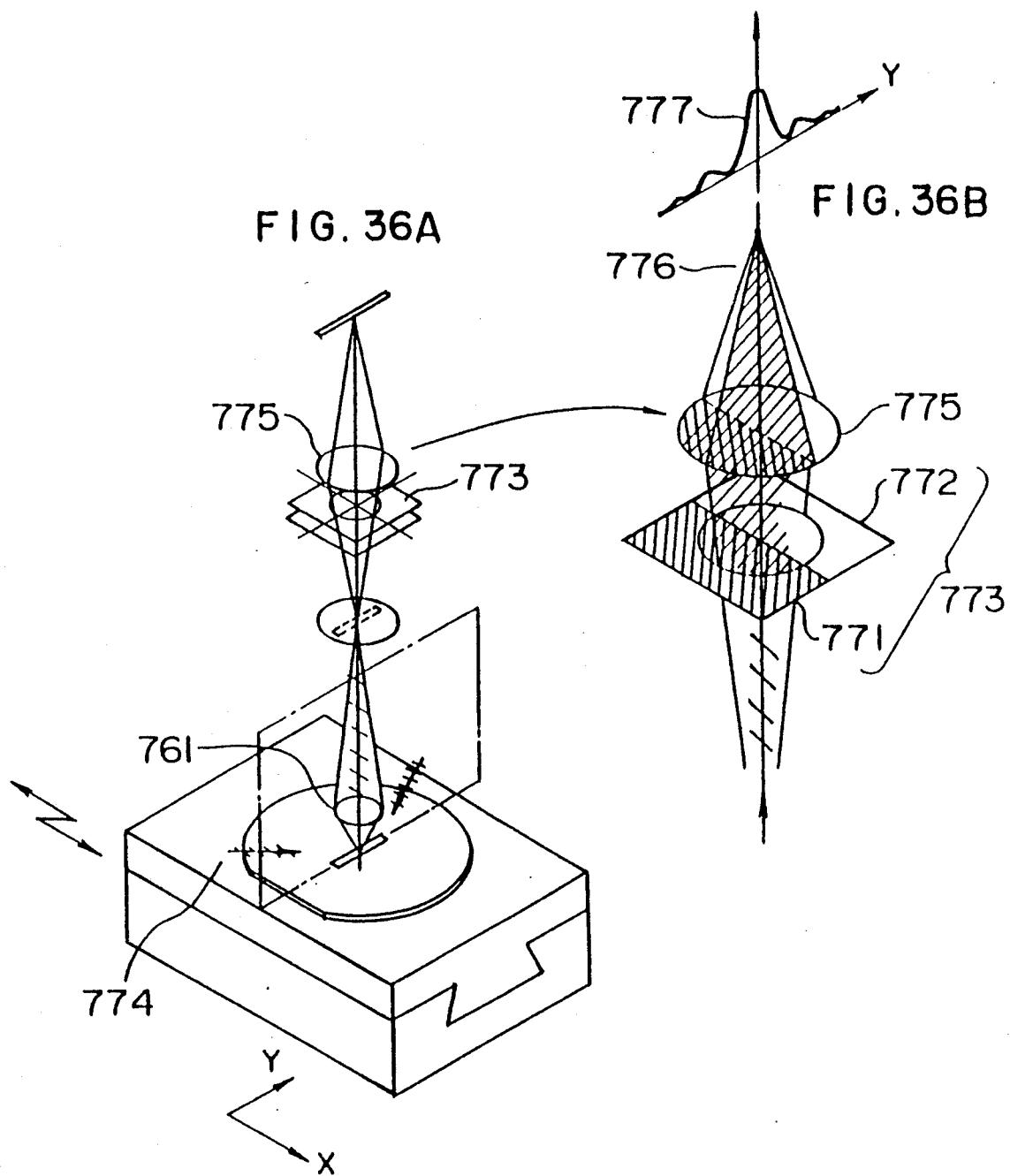

FIG. 40A  FIG. 40B  FIG. 40C  FIG. 40D
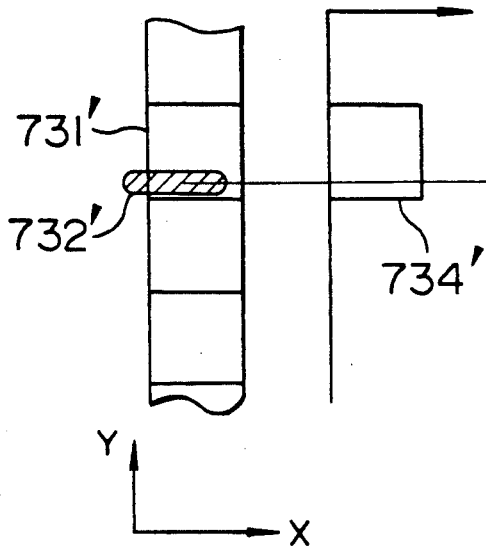
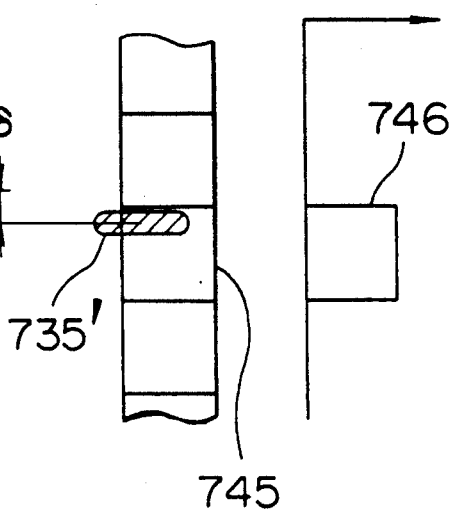
FIG. 40E
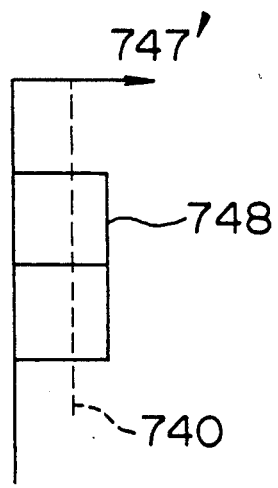

FIG. 41A  FIG. 41B  FIG. 41C  FIG. 41D
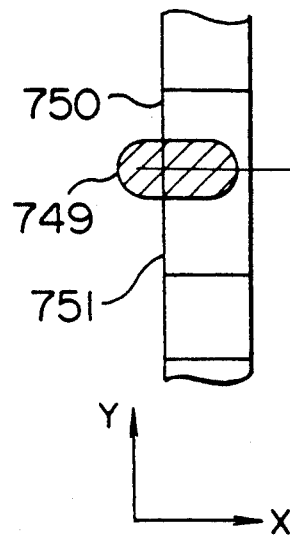
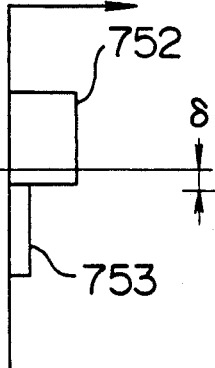
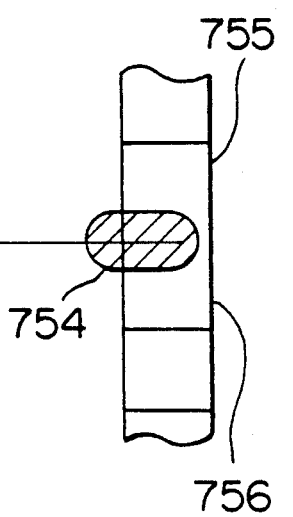
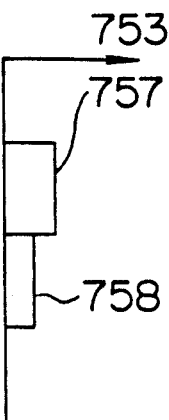
FIG. 41E
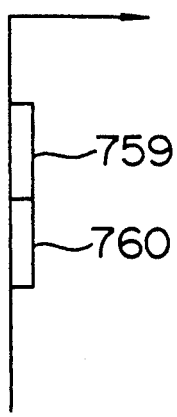

METHOD FOR DETECTING FOREIGN MATTER AND DEVICE FOR REALIZING SAME

BACKGROUND OF THE INVENTION

The present invention relates to a method for detecting considerably small particles of foreign matter on a sample and a device for realizing the same and in particular to a method for detecting considerably small particles of foreign matter, which is suitable for detecting foreign matter on a wafer, which is a (patterned) product, and a device for realizing the same. The present invention can be applied to samples such as semiconductor LSI wafers, glass masks, the surface of magnetic disks, etc.

With the rapid progress of the semiconductor technology the pattern of semiconductor devices has been made finer from the conventional 5 μm level to the 1 μm level. In keeping therewith, in the semiconductor process, a method for detecting considerably small particles of foreign matter corresponding to the 1 μm level and a device for realizing the same have been necessitated.

In view of the circumstances described above the present invention has been done in order to solve the problems of the prior art method and device for detecting foreign matter.

Hereinbelow the prior art technique will be explained.

Taking detection of foreign matter on a patterned wafer as an example, according to the prior art technique, e.g. as represented by that disclosed in JP-A-54-57126, the circuit pattern on the wafer and the foreign matter thereon are irradiated directly with polarized light and attention is paid to differences in the degree of depolarization of the light reflected by each of them. That is, the wafer 1 is irradiated obliquely with S polarized light beams emitted by laser devices 70a and 70b, as indicated in FIG. 5. An "S∞ polarization component, or "Senkrechte" in German, which translates to "vertical or perpendicular line" in English, represents a light component which oscillates in a direction perpendicular to the direction of the plane formed by the illumination light axis. The "P" polarization component, or "Parallele" in German, which translate to "parallel line" in English, represents a light component which oscillates in a direction parallel to the direction of the plane formed by the illumination light axis and perpendicular to the "S" polarization component. In general, since the circuit pattern 71 on the wafer is constructed usually by regular straight line stepwise patterns, the depolarization of the laser light is slight and the S polarization component is conserved in the light 74 reflected by straight line edges in the pattern 71, which are perpendicular to the optical axis of the laser beam 103 as it is. On the other hand, since the shape of the foreign matter is irregular and it can be thought that it is composed of infinitesimal surfaces having various incident angles for the incident laser light, the laser light is scattered. As the result, the scattered light is depolarized and there exist mixedly S and P polarization components in the scattered light 75. Therefore, if a polarizing plate 76 is disposed above the objective lens 7 so as to cut-off the S polarization component (indicated by a full line), only the P polarization component in the light 75 scattered by the foreign matter is detected by a photo-electric converting element 77, as indicated by 79.

FIGS. 6A and 6B show the polarization state of the light scattered by the foreign matter before and after the passage through the polarizing plate respectively, according to the prior art technique. As it is clearly seen from the figures, according to the prior art technique, the P polarization component, which can pass through the polarizing plate, is a considerably small part of the whole light scattered by the foreign matter and the lower limit of the size of detectable particles of foreign matter is about 3 to 5 μm. That is, according to the prior art technique, the polarizing plate is used for removing reflected light coming from the pattern on the sample and this results in that the great part of the light scattered by the foreign matter is also removed. Consequently as indicated in FIG. 7, in the case where the size of the particles of foreign matter 84 is further smaller and it is 1 to 12 μm, it is very difficult to detect them because of decrease in light quantity of the whole scattered light itself and decrease in the light quantity due to the polarizing plate. If the laser light intensity were increased in order to increase the detected light quantity, light scattered by pattern corner portions, which are otherwise not so strongly brilliant, would pass through the polarizing plate, which makes it difficult to discern the foreign matter from the other. Further there are particles of foreign matter, whose depolarization is small, depending on the matter and the shape thereof. In this case almost no P polarization component is contained in the light scattered by the foreign matter which makes it still more difficult to detect them.

An object of the present invention is, in view of the problem of the prior art technique described above, to provide a method for detecting foreign matter and a device for realizing the same capable of detecting light scattered by the foreign matter with a high efficiency independently of the depolarization.

Further there is known another prior art device for detecting foreign matter, as disclosed in an article entitled "A Laser Scan Technique for Electronic Materials Surface Evaluation" by D. R. Oswald J. of Electronics Materials, Vol. 3, No. 1, January 1974, etc.

FIGS. 32 to 34 indicate the prior art principle for detecting foreign matter.

A downward illuminating optical system B consists of a laser light source 501, a focusing lens 502, a polarizing prism 503, a field lens 504, a ¼-wave plate 505 and an objective lens 506.

On the other hand a detecting optical system consists of a light intercepting plate 508, an imaging lens 509 and a detector 510.

A laser light beam 511 outputted by the laser light source 501 is S-polarized. It passes through the polarizing prism 503 and forms a laser spot 511a in a diaphragm 504a in the field lens 504. The laser light beam 511 passing through the field lens 504 passes through the ¼-wave plate 505 and forms a laser spot 511c on the sample 1 owing to the objective lens 506.

In the case where there is no foreign matter on the sample 1, laser light reflected by the surface of the sample (0-th order diffraction light) 511 passes again through the objective lens 506, the ¼-wave plate 505 and the field lens 504. Then it is intercepted by the light intercepting portion 508a of the light intercepting plate after having been reflected totally by the polarizing prism 503. Here the field lens 504 images the extension 511b of the laser light beam 511 at the diaphragm 506a to project it on the light intercepting portion 508a,. The light intercepting portion 508a in the light intercepting plate 508 is obtained by forming an opaque film at the central portion on a transparent glass.

In this case, since S polarized light in the illuminating light 511 is changed into P polarized light in the reflected light 511, when the illuminating laser light 511 passes through the ¼-wave plate 505, and further the reflected laser light 511 passes therethrough, the reflected light 511 is reflected totally by the polarizing prism 503.

In the case where there exists foreign matter 513 on the sample, when the foreign matter 513 is irradiated with the illuminating light 511, light 512 scattered by the foreign matter (high order diffraction light) is produced, which is spread over the whole area of the diaphragm 506a in the objective lens 506 and returns along the same optical path as that of the reflected light 511 described previously.

The surface of the foreign matter 513 presents considerably fine uneven shapes and the scattered light 512 is depolarized, having both S and P.

The P polarized light 512b in the scattered light 512 passes through the transparent portion outside of the light intercepting portion 508a in the light intercepting plate 508, after having been reflected by the polarizing prism 503, and is collected by the imaging lens 509 to be led to the detector 510.

The prior art technique described above had problematical points (1) to (3) as follows:

(1) The S polarized light 512a returns to the laser light source 501 after having passed through the polarizing prism 503 and the focusing lens 502 so as to be collected. This produces noises in the laser light source 501 and has bad influences on the laser oscillation mode. As the result, this causes the shortening of the life of the laser device, unstability (fluctuation phenomena) of the output thereof, etc. and lowers the reliability of the device for detecting foreign matter, etc.

(2) Further, although the P polarized light 512b in the scattered light 512 can be detected, the S polarized light 512a cannot be detected and it is not possible to obtain any satisfactory detection sensitivity.

(3) In addition, since the laser spot 511c is punctual, in order to scan the sample 1 2-dimensionally, it is necessary to dispose means for sweeping the laser beam (not shown in the figure) in the optical path within the downward illuminating optical system, which causes complication of the optical system.

Another object of the present invention is to provide a method for detecting foreign matter and a device for realizing the same capable of improving the performance for detecting foreign matter, in order to solve the problem of the prior art technique.

SUMMARY OF THE INVENTION

The method for detecting considerably small foreign matter and the device for realizing the same according to the present invention irradiates a stripe-shaped domain on a sample with linearly polarized light by means of irradiating means, disposes light intercepting means for intercepting light reflected by a sample, and detects light reflected by the sample, which has passed through the light intercepting means, by means of photo-electric converting means having a detection region corresponding to the stripe-shaped irradiated domain stated above to detect particles of foreign matter, whose size is at a 1 μm level, on the sample.

The object described above is achieved by irradiating obliquely the sample with an irradiating light having a high directivity in the direction forming a desired limited angle in the plane of the sample with respect to the group of principal straight lines constituting the pattern on the sample, intercepting regular scattered light coming from the other groups of straight lines constituting the pattern of the sample in spatial frequency region, and detecting light scattered by the foreign matter on the sample, which has passed through the light intercepting means, through the detecting optical system stated previously by means of a light detector.

The problem of the prior art technique can be solved by removing only the reflected light coming from the pattern without having any influences on the light scattered by the foreign matter and detecting the light scattered by the foreign matter with an efficiency as high as possible. The means therefore utilizes the fact that the diffraction light reflected by the pattern does not enter the detecting optical system, when the angle on the plane of the sample, which is formed by the straight line portion of the pattern and the optical axis of the illuminating light, exceeds a predetermined value. By using the means described above it is possible to remove completely at least two groups of straight lines in the pattern, which are perpendicular to each other on the sample. On the other hand the groups of straight lines, which cannot be removed by the means described above, are removed by intercepting light of an Fourier-transformation image of the remaining groups of straight lines stated above in the spatial frequency region of the detecting optical system, i.e. in a Fourier transformation plane by means of a spatial filter. By using the means described above it is possible to remove the light reflected by the pattern without having any significant influences on the light scattered by the foreign matter and thus to detect the light scattered by the foreign matter with a high efficiency.

BRIEF DESCRIPTION OF THE DRAWINGS

FIG. 5 is a scheme indicating a prior art method for detecting foreign matter;

FIGS. 6A and 6B are schemes indicating the state of the polarization of the light scattered by the foreign matter;

FIG. 7 is a scheme indicating the state of detecting considerably small particles of foreign matter according to the prior art method;

FIGS. 8A to 8D are schemes illustrating a fourth embodiment of the present invention;

FIGS. 9A to 9E are schemes illustrating the Fourier transformation image and the state of the polarization of the pattern and the foreign matter in the spatial frequency region;

FIGS. 10A to 10F are schemes indicating the principle for removing the pattern information by means of a polarizing plate and a spatial filter;

FIGS. 11A to 11D are schemes indicating the principle for removing the pattern information by means of a polarizing spatial filter;

FIGS. 12A to 12E are schemes indicating a fifth embodiment of the present invention;

FIGS. 13A to 13I are schemes indicating a sixth embodiment of the present invention;

FIGS. 18A to 18C are schemes illustrating a method for detecting foreign matter using a polarizing plate;

FIGS. 19A to 19D are schemes illustrating a method for detecting foreign matter using a spatial filter and an adjacent chip comparison;

FIGS. 22A to 22F are side views, plan views and partial cross-sectional views illustrating the optical path in the illuminating optical system B indicated in FIG. 21;

FIGS. 23A to 23G are side views and plan views of the optical path for detecting the light scattered by the foreign matter indicated in FIG. 21, and partial cross-sectional views indicating the spread thereof;

FIG. 36A is a perspective view of the optical system, in the case where a mask is disposed on the image of the Fourier transformation plane indicated in FIG. 8A;

FIG. 36B is an enlarged perspective view of the mask indicated in FIG. 36A;

FIG. 36C is a light intensity distribution of FIG. 36B;

FIGS. 40A to 40E show differential outputs of a pattern corner due to errors in the arrangement of chips; FIG. 40A being an enlarged plan view representing the positional relation between the brilliant part of a pattern corner on one chip and a detecting element of the sensor; FIG 40B being a diagram showing the output of the pattern corner in the case indicated in FIG. 40A; FIG. 40C being an enlarged plan view representing the positional relation between the brilliant part of a pattern corner on the other chip and the detecting element of the sensor; FIG. 40D being a diagram showing the output of the pattern corner in the case indicated in FIG. 40C; FIG. 40E being a diagram representing the differential output between the output indicated in FIG. 40B and that indicated in FIG. 40D; and FIGS. 41A to 41E show outputs of the pattern corner, in the case where the image is smoothed and the width is enlarged in the direction, along which positional deviations are produced; FIG. 41A showing the output in the case where the brilliant part of a pattern corner on one chip is positioned at the joint portion of two sensors; FIG. 41B being a diagram showing the output of the pattern corner in the case indicated in FIG. 41A; FIG. 41C showing the output, in the case where the brilliant part of the corresponding pattern corner on the other chip is positioned at the joint portion of the two sensors; FIG. 41D being a diagram showing the output of the pattern corner in the case indicated in FIG. 41C; FIG. 41E being a diagram representing the differential output between the output indicated in FIG. 41B and that indicated in FIG. 41D.

DESCRIPTION OF THE SPECIFIC EMBODIMENTS

Hereinbelow an embodiment of the present invention will be explained, by referring to FIGS. 1 to 4.

Figure 2:
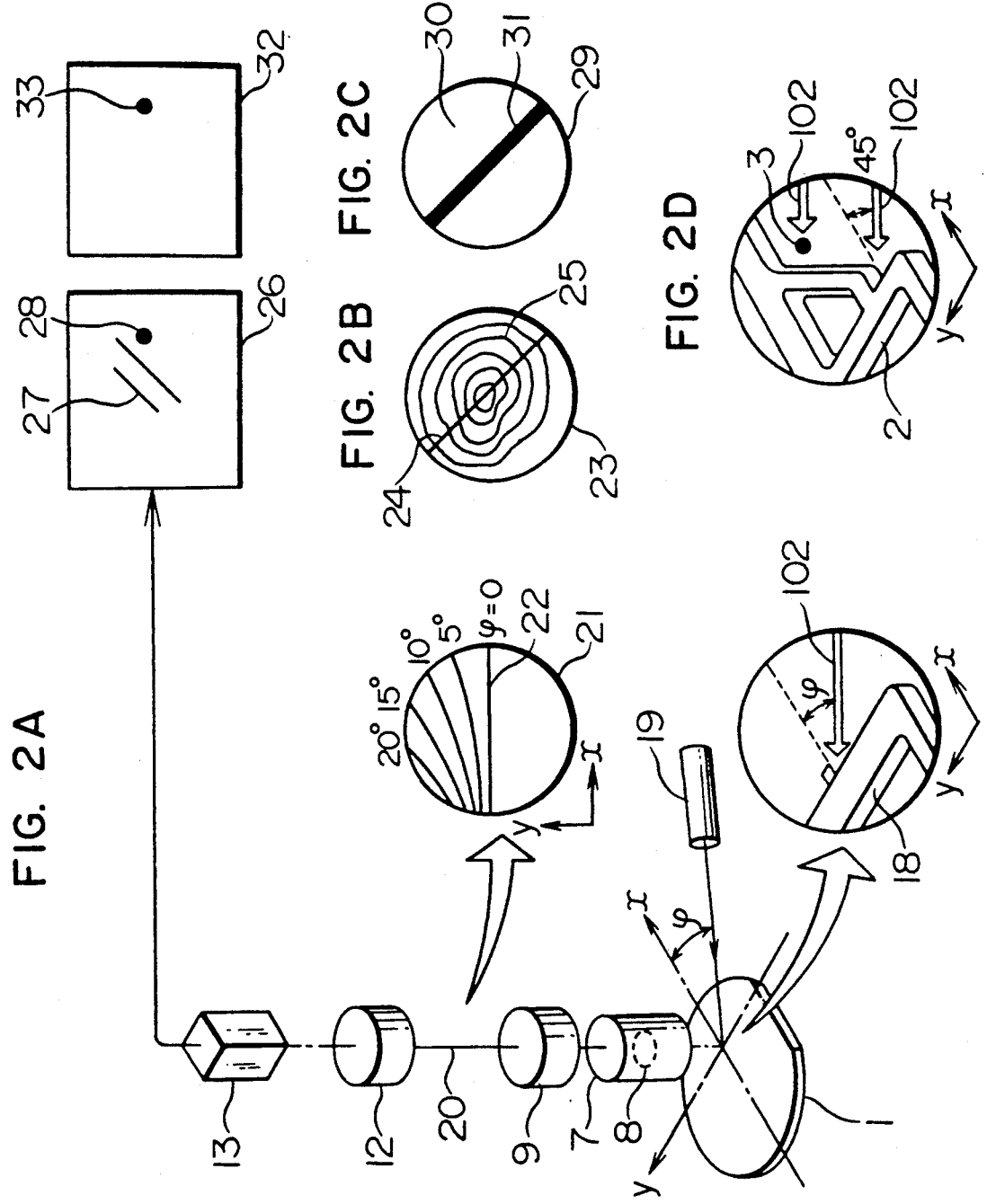
FIGS. 2A to 2D are schemes indicating the principle of the present invention.

At first the fundamental principle of the present invention is explained, taking an examination for detecting foreign matter on a pattered wafer as an example, referring to FIG. 2. FIG. 2A is a scheme indicating the principle of the optical system for detecting the foreign matter, in which a wafer 1 is imaged on a photo-electric converting element 13 through the objective lens 7, relay lenses 9 and 12. On the other hand the spatial frequency region within the objective lens 7, i.e. the Fourier transformation area (corresponding to the emitting pupil) 8 is imaged at a position indicated by 20 by the relay lens 9. According to the present invention attention is paid to the fact that the circuit pattern formed on the wafer is constructed by in total 3 groups of straight lines, i.e. 2 groups of straight lines, which intercept each other approximately perpendicularly to each other and a group of straight lines existing only in a small part and forming an angle of 45° with the groups of straight lines stated above, as indicated in FIG. 2D. Now assume a pattern 18 consisting of straight line edge portions, which are parallel to the x and y plane. The angle formed on the wafer surface by the beam 102 of the laser device 19 illuminating it obliquely and the x axis be $\phi$. Depending on the angle $\phi$, the diffraction light reflected by the straight line edge portions in the direction of the y axis in the pattern 18, i.e. the Fourier-transformation image, varies as indicated by 22, at a position indicated by 20, i.e. the image position of the Fourier transformation area 8 in the objective lens 7 (spatial frequency region =emitting pupil) (32 indicates the image of the emitting pupil). That is, it can be understood that the diffraction light reflected by the straight line edge portions enters no more the objective lens, when the angle $\phi$ exceeds a certain value $\phi_m$. For example, in the case where an objective lens having an NA (Numeral Aperture) of 0.4 is used, $\phi_m = 20°$. Consequently, in the case where an objective lens having an NA of 0.4 is used for the detecting optical system, if the angle $\phi$ of the laser beam for the oblique illumination is set to a value exceeding 20° with respect to the x and y axes, it is possible to remove completely the light reflected by the straight line edge portions, which are parallel to the x and the y axes, respectively. This angle $\phi_m$ varies, depending on the NA of the objective lens and it increases with increasing NA. At this time the light scattered by the foreign matter is not influenced at all. FIG. 2B shows the light reflected by the pattern and the foreign matter, when the angle $\phi$ is set to 45° with a margin. Since the diffraction light reflected by the straight line edge portions in the pattern 2, which are parallel to the x and the y axes, doesn't enter the objective lens 7, this pattern information can be removed completely, as indicated by a detected image 26. On the contrary the diffraction light reflected by the straight line edge portions forming an angle of 45° with the x and y axes in the pattern 2 enters the objective lens 7 is collected in an elongated area at the position indicated by 20, i.e. the Fourier transformation area, so as to form the fourier transformation image, and the pattern information 27 can be obtained also in the detected image 26. Reference numeral 25 represents the Fourier transformation image of the foreign matter, which is extended largely in the Fourier transformation area because of the irregularity of the shape thereof. Paying attention to the difference between the shapes of the two Fourier transformation images, it is possible to intercept the Fourier transformation image due to the straight line edge portion, which is in the direction of 45° by disposing a spatial filter 29 having a light intercepting portion 31 at the position indicated by 20. As the result it is possible to extract only foreign matter information 33, as indicated by the detected image 32. Further, since there exists the pattern in the direction of 45° merely slightly on the wafer and the Fourier transformation image 24 is very narrow, the light intercepting portion 31 of the spatial filter 29 can be also fairly narrow.

Therefore the quantity of the intercepted light in the light scattered by the foreign matter due to this light intercepting portion 31 is very small.

As described above, according to the fundamental principle of the present invention the wafer is irradiated obliquely at an angle, for which no reflected diffraction light in the directions of the x and the y axes enters the objective lens. In this way information for the pattern in the direction of the x and the y axes, which is the most part of the circuit pattern on the wafer, is removed. Patter information concerning the remaining directions is removed by means of a spatial filter disposed in the Fourier transformation area in the objective lens or the detecting optical system. Thus only foreign matter information is extracted without impairing seriously the light scattered by the foreign matter.

Hereinbelow a first embodiment of the present invention will be explained referring to FIG. 1.

Figure 1:
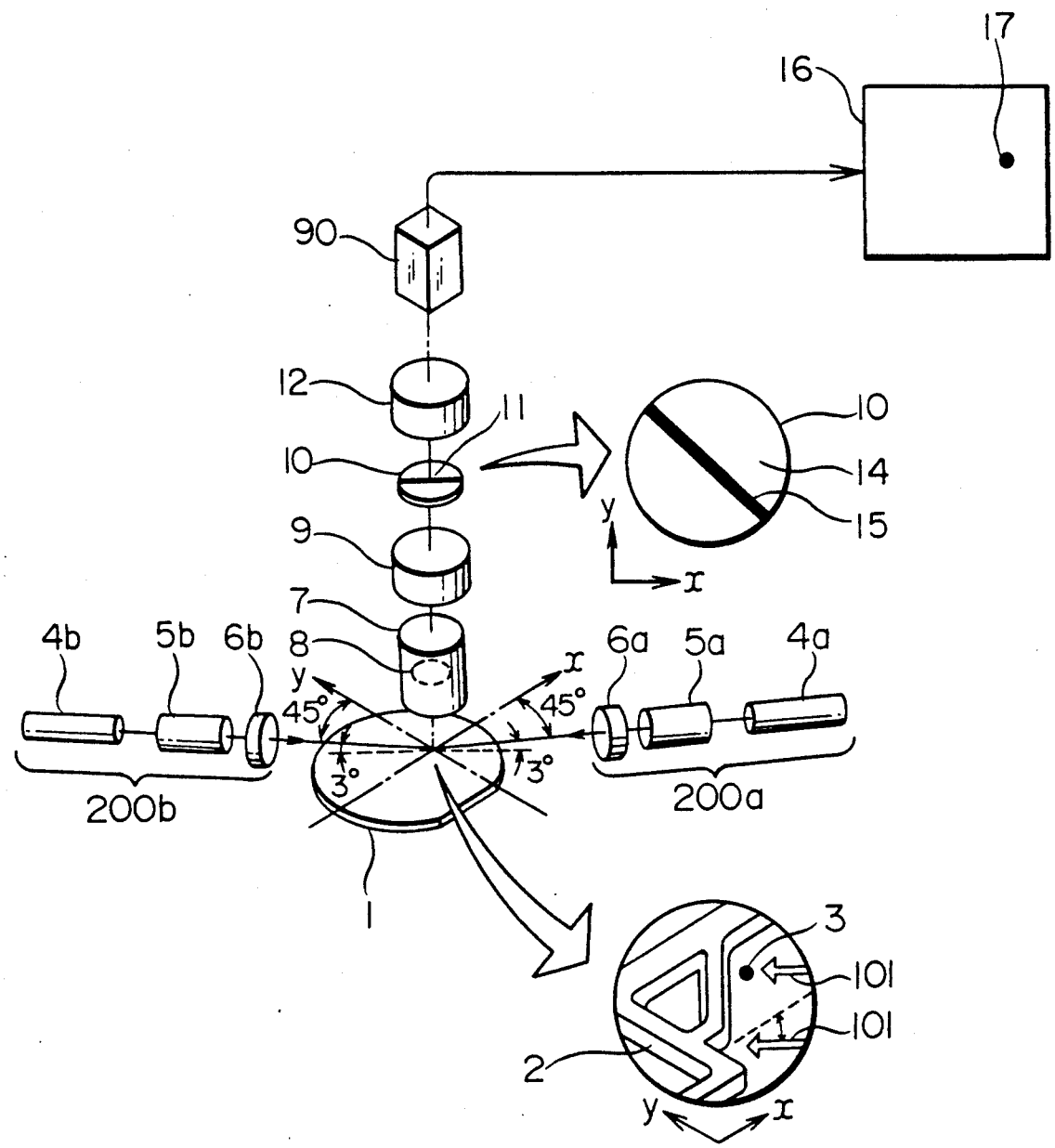
FIG. 1 is a perspective view illustrating the optical system for detecting foreign matter in a first embodiment according to the present invention.

FIG. 1 is a perspective view illustrating a foreign matter detecting optical system, which is a first embodiment of the present invention. This optical system consists of an x-y stage (not shown in the figure), laser oblique illumination optical system 200a and 200b, an objective lens 7, a relay lens 9, a spatial filter 10, a relay lens 12 and a 2-dimensional solid state imaging element 90. In the figure the sample is a product wafer, on which a circuit pattern is formed. Each of the laser oblique illumination optical systems 200a and 200b consists of a semiconductor laser device 4a, 4b, a beam correcting optical system 5a, 5b and a focusing lens 6a, 6b. Beams emitted by the semiconductor devices 4a and 4b, each of which beams has an elliptic cross-section, illuminates the wafer with an angle of inclination of 3° and an azimuthal angle of 45° from the x and the y axes in two directions through the focusing lenses 6a and 6b after having been shaped into circular beams by the beam correcting optical systems 5a and 5b, respectively. As shown in FIG. 1, the laser oblique illuminating optical systems 200a, 200b must be inclined somewhat to enable the laser light to illuminate foreign matter disposed on the sample, but between the raised patterns 2. The wafer 1 is imaged on the 2-dimensional solid state imaging element 90 through the objective lens 7, and the relay lenses 9 and 12. On the other hand the Fourier transformation area (spatial frequency region =emitting pupil) 8 of the objective lens 7 is imaged at a position indicated by 11 by the relay lens 9. In this embodiment the wafer is so arranged that the principal 2 groups of straight line edges constituting the circuit pattern 2 are parallel to the x and the y axes, respectively. Consequently the diffraction light reflected by the groups of straight line edges parallel to the x and the y axes, respectively, don't enter the objective lens owing to the fact that the wafer is irradiated obliquely with an angle of 45° with respect to the x and the y axes. In this way it is possible to remove pattern information concerning them. On the contrary, since groups of straight line edges forming an angle of 45° with the x and the y axes are perpendicular to the laser beam, the diffraction light reflected by them forms a Fourier transformation image by light collected in a narrow region, as indicated in FIG. 2B, on a Fourier transformation plane 11. Consequently this pattern information can be removed by disposing a spatial filter 10 having a light intercepting portion 15 at the position indicated by 11. Further, at this time, the diffraction light reflected in the direction of 45°, which is parallel to the laser beam 102, does not enter the objective lens 7. By the method described above all the information concerning the circuit pattern on the wafer can be removed and as the result it is possible to extract only foreign matter information, as indicated in a detected image 16 on the 2-dimensional solid state imaging element 90.

In this embodiment, as stated already for the explanation of the principle since it is possible to remove information of the pattern in the directions of the x and the y axes, which is the most part of the circuit pattern on the wafer, by the oblique illumination with an azimuthal angle of 45° without having any influences on the light scattered by the foreign matter and further to reduce fairly remarkably the width of the light intercepting portion 15 of the spatial filter 10 for removing pattern information in the remaining directions, it is possible to extract only the foreign matter information without impairing significantly the light scattered by the foreign matter.

Hereinbelow the second embodiment of the present invention will be explained, referring to FIG. 3.

Figure 3:
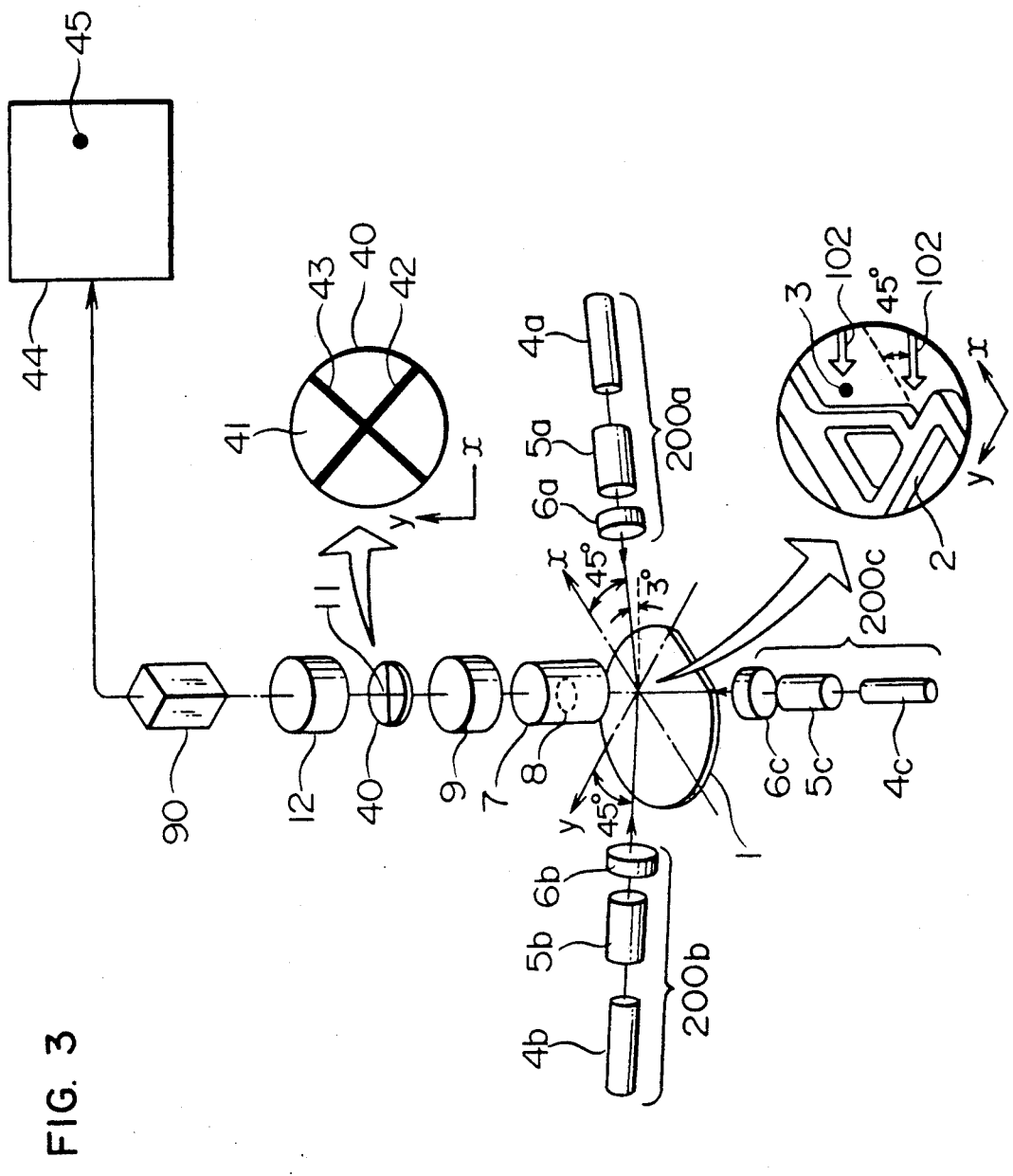
FIG. 3 is a perspective view illustrating the optical system for detecting foreign matter in a second embodiment according to the present invention.

FIG. 3 is a perspective view illustrating a foreign matter detecting optical system, which is the second embodiment of the present invention. This optical system is so constructed that the sample is irradiated obliquely in total 4 directions, adding two laser oblique illumination optical systems 200c and 200d (not shown in the figure) in directions, which are perpendicular to the laser oblique illumination optical systems already existing in the foreign matter detecting optical system, which is the first embodiment indicated in FIG. 1, thereto. In addition, corresponding thereto, a spatial filter 40 having two light intercepting portions 42 and 43 is disposed on the Fourier transformation plane 11. Otherwise it has the construction and function completely identical from all the points of view to those of the foreign matter detecting optical system, which is the first embodiment. Also in the case where the sample is illuminated obliquely in the 4 directions with an azimuthal angle of 45° with respect to the x and the y axes, since the diffraction light reflected by the groups of straight line edges parallel to the x and the y axes in the pattern 2 does not enter the objective lens, it is possible to remove information of them. On the other hand, since the groups of straight line edges forming an angle of 45° with the x and the y axes are perpendicular to the laser beams in the 4 directions, the diffraction light reflected by them forms a cross-shaped Fourier transformation image, for which light is collected in a narrow region on the Fourier transformation plane 11. Therefore this pattern information can be removed by disposing the spatial filter 40 having the two light intercepting portions 42 and 43 at the position indicated by 11. By the method described above all the information of the circuit pattern on the wafer can be removed and as the result it is possible to extract only the foreign matter information 45, as indicated in a detected image 44 on a 2-dimensional solid state imaging element 90.

This embodiment has not only the same effect as the first embodiment but also the following effect. That is, some foreign matters have directivity in the shape thereof. Therefore, in the case where the sample is illuminated in a restricted direction, the directivity of the scattered light is enhanced and at the worst case there can be cases, where no scattered light enters the objective lens. In this embodiment since the sample is illuminated obliquely in 4 directions, even in the above cases it is possible to reduce the directivity of the light scattered by the foreign matter and thus to prevent the decrease in the amount of the foreign matter detecting light. Furthermore, for a particle of foreign matter, which sticks to a stepwise portion of the pattern and is in the shadow of the step, when it is illuminated in 2 directions, so that it is difficult to find it, a satisfactory amount of illuminating light can be obtained by the illumination in 4 directions and thus it is possible to prevent overlooking the foreign matter.

Hereinbelow a third embodiment of the present invention will be explained, referring to FIG. 4.

Figure 4:
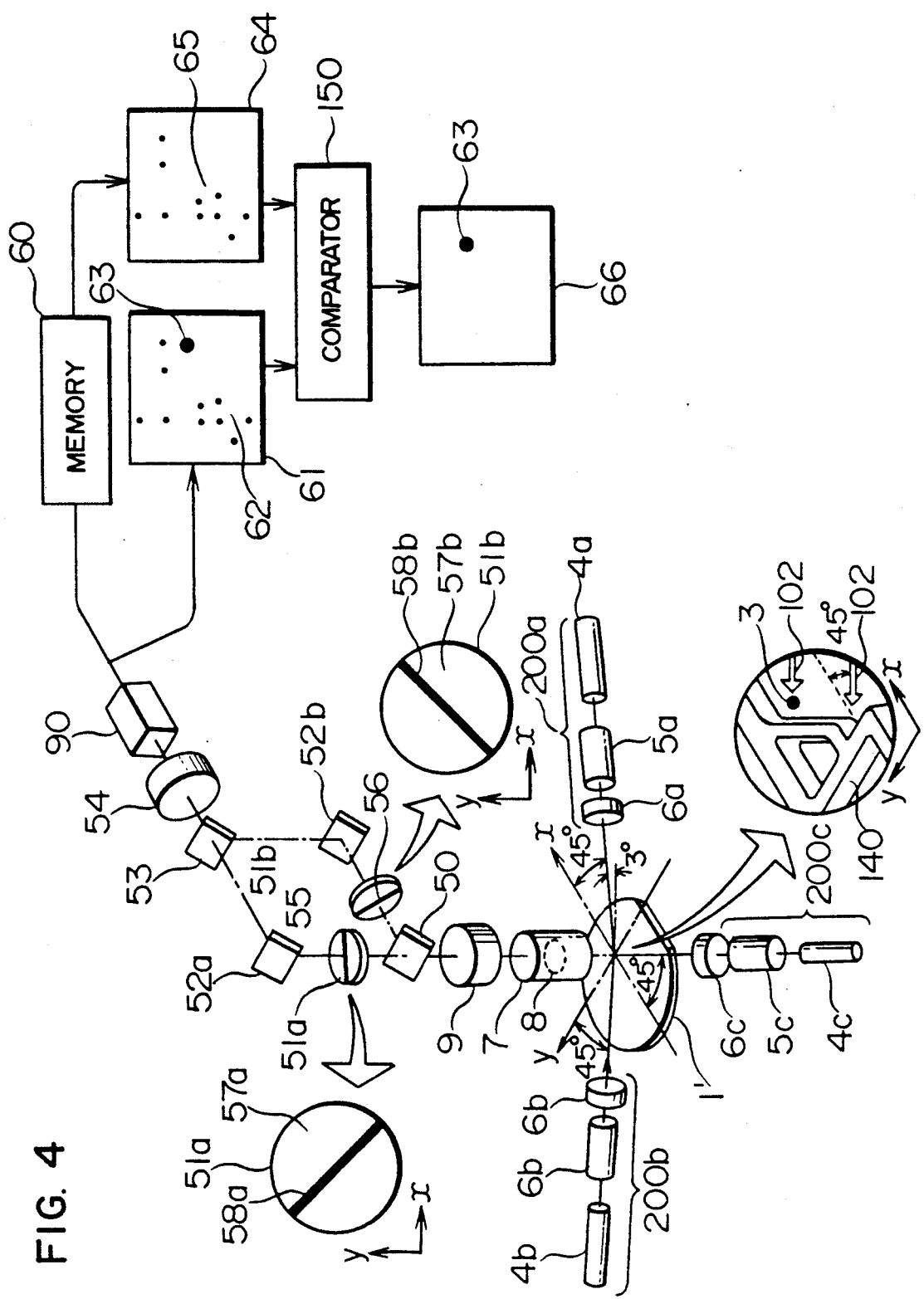
FIG. 4 is a perspective view illustrating the optical system for detecting foreign matter in a third embodiment according to the present invention.

FIG. 4 is a perspective view illustrating a foreign matter detecting optical system in a third embodiment of the present invention. This optical system consists of an x-y stage (not shown in the figure), laser oblique illumination optical systems 200a, 200b, 200c and 200d (not shown in the figure), an objective lens 7, a relay lens 9, a wavelength separating mirror 50, spatial filters 51a and 51b, mirrors 52a and 52b, a wavelength synthesizing mirror 53, a relay lens 54, a 2-dimensional solid state imaging element 90, a memory 60 as a signal processing system, and a comparing circuit 150. In the figure the sample is product wafer, on which a circuit pattern is formed just as in the two preceding embodiments. Although the construction, the arrangement and the function of each of the four laser oblique illumination optical system 200a, 200b, 200c and 200d are completely identical to those in the second embodiment, the semiconductor laser devices 4a and 4b use a wavelength of 840 nm, while the semiconductor laser devices 4c and 4d use a wavelength of 780 nm. A wafer 1' is imaged on the 2-dimensional solid state imaging element 90 through the objective lens 7 and the relay lenses 9 and 54. On the other hand the Fourier transformation area (spatial frequency region=emitting pupil) 8 of the objective lens 7 is imaged at positions indicated by 55 and 56 through the relay lens 9. The wavelength separating mirror 50 and the wavelength synthesizing mirror 53 transmit light having a wavelength of 840 nm and reflect light having a wavelength of 780 nm.

Hereinbelow the function of the foreign matter detecting optical system according to the present invention will be explained. In the case where the sample is illuminated in 4 directions at an angle of 45° with respect to the x and the y axes, just as the second embodiment, since the diffraction light reflected by the groups of straight line edges parallel to the x and the y axes in the pattern 140 don't enter the objective lens, it is possible to remove information thereof. On the other hand the groups of straight line edges forming an angle of 45° with the x and the y axes are perpendicular to the laser beams in the 4 directions. The diffraction light reflected by the group of straight line edges illuminated by the beams emitted by the semiconductor devices 4a and 4b wavelength of 840 nm, which form an angle of 45° with the x and the y axes and are perpendicular to the beams, passes through the wavelength separating mirror 50 and forms a Fourier transformation image, for which light is collected in a narrow region parallel to the beams on the Fourier transformation plane 55, as indicated in FIG. 2B. Consequently this pattern information can be removed by disposing a spatial filter 51a having a light intercepting portion 58a at a position indicated by 55. On the contrary, the diffraction light reflected by the group of straight line edges illuminated by the beams emitted by the semiconductor devices 4c and 4d of wavelength of 780 nm, which form an angle of 45° with the x and the y axes and are perpendicular to the same beams, is reflected by the wavelength separating mirror 50 and forms a Fourier transformation image, for which light is collected in a narrow region parallel to the beams on the Fourier transformation plane 56, as indicted in FIG. 2B. Consequently, in the same way as that described above, this pattern information can be removed by disposing a spatial filter 51b having a light intercepting portion 58b at a position indicated by 56. The light reflected by the wafer 1' and having 2 wavelengths, from which information concerning the circuit pattern is removed in the manner described above, forms an image through a relay lens 54 on a 2-dimensional solid state imaging element 90 after having been synthesized by means of a wavelength synthesizing mirror 53. On the other hand, since the difference in level in the wafer 1' is greater than that in the wafer 1 for the two embodiments described previously (in the semiconductor fabrication process such as the Al wiring process the difference in level produced by a succeeding step is greater than that produced by a preceding step), the scattering state of light at a corner portion in the pattern 140 is close to that of the foreign matter and thus the light scattered by it passes through the spatial filters 51a and 51b. As the result, in the detection image 61 on the 2-dimensional solid state imaging element 90 there exists mixedly information 62 of the corner portion in the pattern together with foreign matter information 63. Therefore it is possible to extract only the foreign matter information 63, as indicated by a difference image 66, by comparing the detected image 61 with a stored image 64 of the same position on an adjacent chip, which is stored previously in the memory 60 and by removing the information of the corner portion in the pattern, which is common to the two images.

As explained above, this embodiment brings about not only the same effects as the first and the second embodiments but also effects stated below. That is, in this embodiment, the Fourier transformation image, which should be otherwise cross-shaped, as indicated in the second embodiment, is separated into 2 separate straight line Fourier transformation images by separating the light reflected by the wafer into 2 wavelength components so that the area of the light intercepting portion of one spatial filter can be reduced. As the result, the amount of the intercepted light in the light scattered by the foreign matter decreases and the amount of light for detecting the foreign matter increases. Further, if the adjacent chip comparison method is used together, the power for detecting the foreign matter is increased for a wafer having great differences in level, for which heretofore the power was lowered.

In addition, although a semiconductor wafer is used as the sample in the above embodiments, the present invention can be applied to the detection of foreign matter on a reticle, a mask or other patterns having some regularity and it can be applied also to the detection of foreign matter on a sample on which no pattern is formed.

Further, although the light reflected by the wafer is separated into two different wavelengths by means of a wavelength separating mirror in the third embodiment, it is possible of course to substitute it by a deflection beam splitter and to separate the light into two polarization components, which are perpendicular to each other. In this case the oblique illumination is effected by using two linearly polarized laser beams, whose polarization planes are perpendicular to each other.

Still further, although the angle of the laser beams is set to 45° in the above embodiments, the azimuthal angle may be set to other values, if it is an angle, for which the diffraction light reflected by the edge portions doesn't enter the objective lens. The angle stated above is determined, depending on the NA of the objective lens.

As explained above, according to the present invention, it is possible to remove information of the pattern in the directions of the x and the y axes, which is the most part of the circuit pattern on the wafer, without impairing the light scattered by the foreign matter by a very simple construction, in which the wafer is illuminated obliquely at an angle for which the reflected diffraction light in the directions of the x and the y axes doesn't enter the objective lens and further the amount of the foreign matter detecting light is increased significantly with respect to that obtained by the prior art method by removing information of the pattern in the remaining directions by means of spatial filters. In addition, since the power of the foreign matter detection doesn't depend on the shape of the pattern or the foreign matter, it is possible to detect still smaller particle of foreign matter together with the increase in the amount of the foreign matter detecting light and thus the present, invention has an effect to contribute to improvement of the reliability and increase of the fabrication yield of semiconductor products.

Although the object of the present invention can be achieved by the embodiments described above, another technique for increasing the power for detecting small particles of foreign matter will be explained below.

The wafer 1 is irradiated obliquely with S polarized beams emitted by laser devices 203a and 203b, as indicated in FIG. 18A. If there exists particles of foreign matter 401 and 402 on a pattern 211 of the wafer, as indicated in FIG. 18B, S and P polarization components exist mixedly in the light scattered by the foreign matters. On the contrary, the S polarization component is conserved, as it is, in the light scattered by straight line edges in the pattern 211 perpendicular to the optical axis of the laser beam. Therefore the pattern information can be removed by disposing a polarizing plate 101 above the objective lens 7 so as to intercept the S polarization component (indicated by a full line) and thus only P polarization component in the light scattered by the particles of foreign matter can be detected by a photoelectric converting element 102. According to this method it is sufficiently possible to detect particles of foreign matter 401 as small as 3 to 5 μm on a wafer, on which a pattern is formed.

However, since the P polarization component is considerably small part of the whole scattered light in the light scattered by the foreign matter in the case where the size of the considerably small particles of foreign matter 402 is as small as 1 to 2 μm, the amount of the detecting light is remarkably reduced by the polarizing plate and there may be cases where it is difficult to distinguish the light scattered by the foreign matter from the light 103 scattered by a pattern corner portion, as indicated in FIG. 18C. The polarizing plate is used in order to remove the light scattered by the pattern, but for this reason a great part of the light scattered by the foreign matter is also removed. Further there are matters, for which scattered light is hardly depolarized, depending on the substance and the shape, and there may be cases where almost no P polarization component is contained in the light scattered by the foreign matter and the detection thereof is difficult.

Figure 20A:
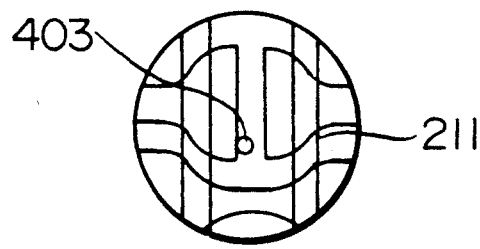
FIGS. 20A to 20H are schemes illustrating aspects impairing information of the foreign matter due to the spatial filter.
Figure 20E:
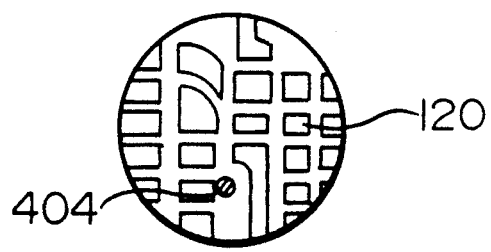
Figure 20B:
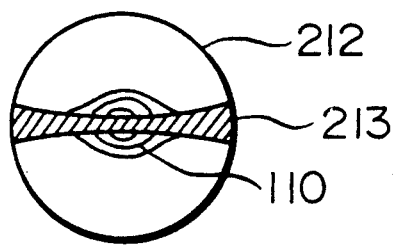
Figure 20F:
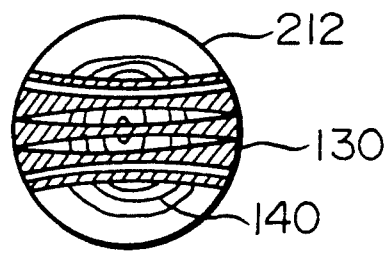
Figure 20C:
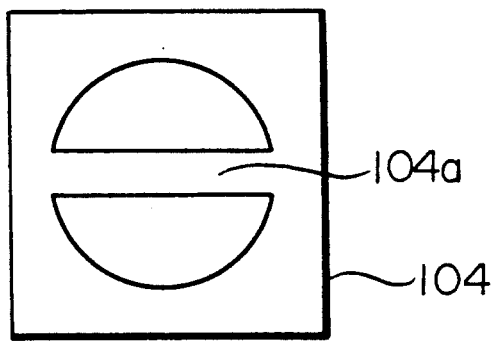
Figure 20G:
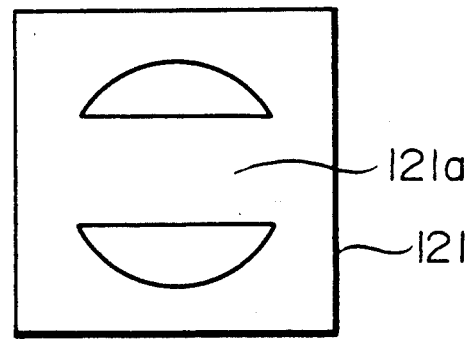
Figure 20D:
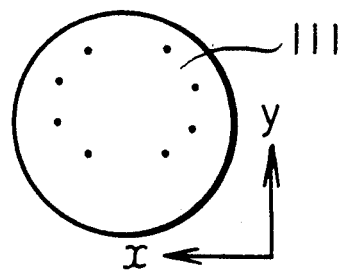
Figure 20H:
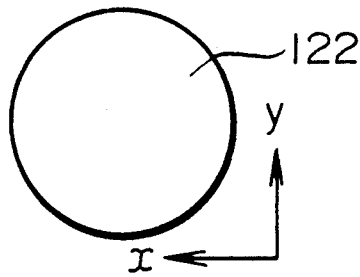

Furthermore, as indicated in FIG. 19A, the emitting pupil, i.e. the spatial frequency region (Fourier transformation area) 8 in the objective lens 7 is imaged at a position indicated by 300 by a field lens 205 and forms a Fourier transformation image 212 of the pattern 211 and the particles of foreign matter 401 and 402 indicated in FIG. 19B (FIG. 19C). Reference numeral 213 indicates a Fourier transformation image of the straight line edge portion in the pattern 211 which is perpendicular to the optical axis of the laser beam, which image exists locally in the spatial frequency region, as indicated in the figure. 214 is a Fourier transformation image of the particles of foreign matters 401 and 402, which exists in general all over the spatial frequency region as indicated in the figure. When a spatial filter 104 having a light intercepting portion 104a indicated in FIG. 19D is disposed at a position indicated by 300 so as to intercept the light of the Fourier transformation image 213 of straight line edges, the image formed on a photoelectric converting element 208 by a field lens 207 consists of a part coming from the particles of foreign matter 401a and 402a and another part coming from the pattern corner portion as indicated by 105 in FIG. 19A. Then this detected image 105 is compared with a stored image 106 of the same place in an adjacent chip which is stored in a memory 209, (image obtained by the laser oblique illumination through the spatial filter 104), in a comparing circuit 210 and the image of the particles of foreign matter 401a and 402a is detected by using a differential image 107. However in such a foreign matter detecting method there is a problem as follows. That is, in the case where the foreign matter 403 on the pattern 211 has some directivity in the shapes, as indicated in FIG. 20A, the Fourier transformation image 110 doesn't sufficiently extend and it may be superposed on the Fourier transformation image 213 of the straight line edges. In this case the Fourier transformation image of the foreign matter is intercepted by the light intercepting portion 104a in the spatial filter 104 and the foreign matter may not be detected, as indicated by 111. On the contrary, as indicated in FIG. 20E, depending on the shape of the circuit pattern 120, there may be a case where the Fourier transformation image 130 of the straight line edges is not collected in a straight-line-shaped area but extends over a large area, and it is superposed on the Fourier transformation image 140 of the foreign matter 404. In this case, if a spatial filter 121 having a large light intercepting portion 121a is used for intercepting the Fourier transformation image 130, the Fourier transformation image 140 of the foreign matter is also intercepted and it is not possible to detect the foreign matter, as indicated by 122.

In this way the method using a polarizing plate has problems that the amount of the light scattered by the foreign matter is reduced and that it is not possible to detect foreign matter depolarizing scarcely and on the other hand the method using a spatial filters has a problem that the power for detecting the foreign matter is reduced due to the shape of the Fourier transformation image of the foreign matter or the pattern.

One of the objects of the present invention is to provide a foreign matter detecting method and a device for realizing the same capable of detecting the light scattered by the foreign matter with a still higher efficiency without depending on the depolarization by the foreign matter and the Fourier transformation image of the foreign matter or the pattern.

The above object can be achieved by illuminating obliquely the sample with a linearly polarized light having a high directivity; disposing a polarizing plate mounted at a desired restricted portion or an optical element varying the polarization state of the light passing through that portion; intercepting selectively only a desired polarization component of the light scattered by the sample in a desired spatial frequency region; and detecting the light scattered by the foreign matter on the sample, which has passed through the light intercepting means stated above, by means of a photodetector through the detecting optical system stated above.

The problems stated previously can be solved by removing only the light reflected by the pattern without having any influences on the light scattered by the foreign matter and detecting the light scattered by the foreign matter with an efficiency as high as possible. The means therefor utilizes differences in the shape and the polarization component between the Fourier transformation image of the pattern and the Fourier transformation image of the foreign matter in the spatial frequency region in the detecting optical system, i.e. the Fourier transformation plane. That is, it is possible to form a Fourier transformation image different from the pattern and to detect the light scattered by the foreign matter and including polarization components of various directions without impairing it seriously by intercepting only a particular polarization component constituting the Fourier transformation image of the pattern in the region corresponding to the Fourier transformation image of the pattern on the Fourier transformation plane.

At the comparison examination the image indicated in FIG. 12A is compared with that indicated in FIG. 12B and disaccording parts are judged as foreign matter. However, since there are positional deviations in chips on the wafer, it is not possible to put the two images completely in accordance with each other. There fore, if they are compared with each other after having gradated more or less the whole images, the comparison is hardly influenced by the positional deviations of the two images.

Hereinbelow means for smoothing the images will be explained using length representations according to common engineering convention wherein image, real image, and light beam widths ($d_1$, $l_1$, and $D_1$, respectively) are in units of $\mu$m and the wavelength of light is in Å units.

Figure 35A:
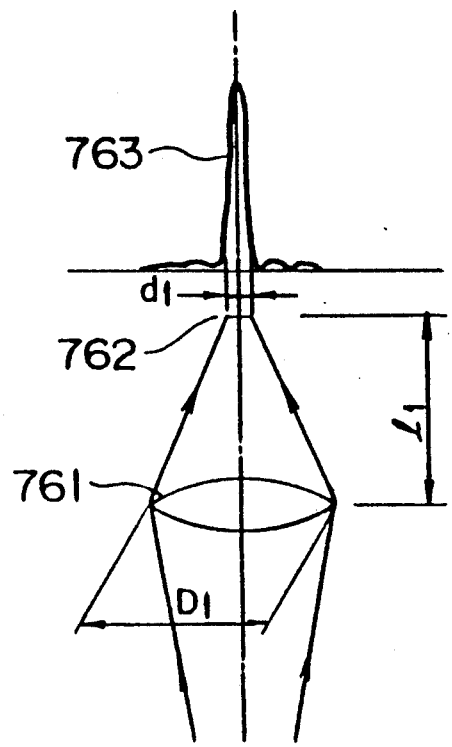
FIG. 35A shows the light intensity distribution, when light is projected upward on the objective lens according to the prior art techniques.

When a light beam, whose width is $D_1$, is projected upward on an objective lens 761, as indicated in FIG. 35A, an image having a width $d_1$ formed at the imaging plane, where an intensity distribution as indicated by 763 is obtained. Denoting the wavelength of the light by $\lambda_1$ and the distance from the lens 761 to the real image by $l_1$, the following Eq. (1) is valid;

$$d_1 = 2.44 \frac{\lambda_1 \cdot l_1}{D_1} \quad (1)$$

Figure 35B:
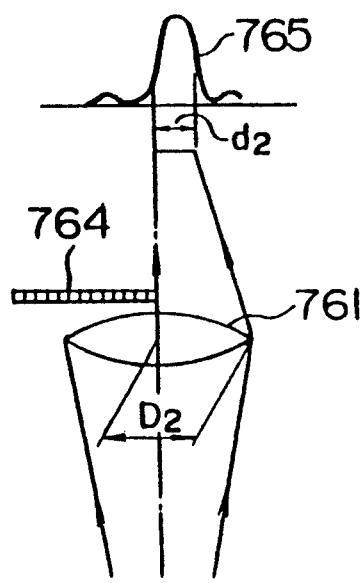
FIG. 35B shows the light intensity distribution, when the light projected upward on the objective lens is intercepted by a ¼ wave plate.

Consequently, when a half of the area of the lens 761 is covered by a light intercepting plate 764, $D_2 = D_1/2$. Using Eq. (1), it is understood that $d_2 = 2d_1$. That is, by intercepting the light beam at a half of the area of the lens 761 it is possible to enlarge the width $d_1$ of the image 763 by a factor 2 to the width d₂ of the image 765, as indicated in FIG. 35B.

However, since the amount of light is reduced to ½, this method cannot be used in practice as it is.

Therefore, according to the present invention, as indicated in FIGS. 36A to 36C, there is disposed a mask 773 on the image 236 of the Fourier transformation plane indicated in FIG. 12A. A half of the mask is constructed by a ½ wave plate 771 and the remaining half is made of a transparent glass plate 772.

Further S polarized light (i.e. light, for which the polarization plane of illumination light 774 is perpendicular to a plane indicated by a dot-dashed line, formed by the optical axis of the illumination light 774 and the optical axis of the objective lens 761, the direction of polarization of the light being indicated by short segments of line in FIG. 36A) is used for the illumination light 774 illuminating obliquely downward the sample 2.

For this reason the light, which has passed through the transparent glass plate 772 remains S polarized, while the light, which has passed through the ½ wave plate 771, is changed into P polarized light (i.e. light, whose polarization plane is perpendicular to the polarization plane of the S polarized light). Since P polarized light and S polarized light does not interfere with each other at the imaging plane 776, it can be thought that the S polarized light and the P polarized light reach independently a point 776 and form an image there.

Figure 37:
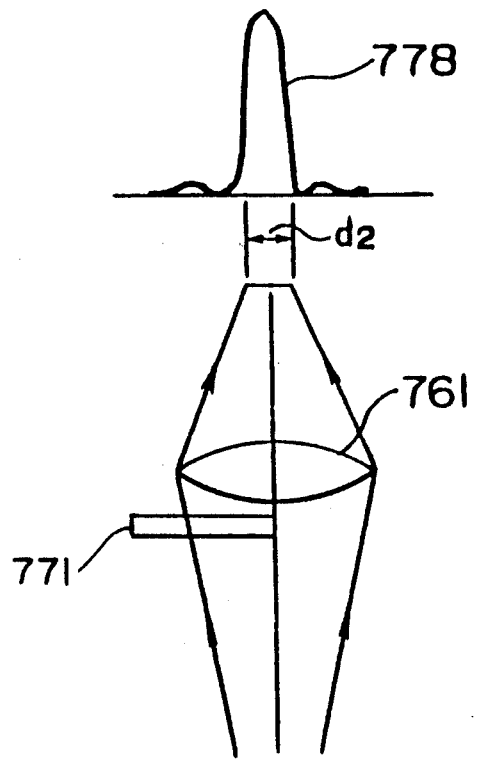
FIG. 37 shows the light intensity distribution obtained by the same method as FIG. 35B, in the case where the image is smoothed so that the image is enlarged in the direction of the width.

Consequently, according to the present invention, the real image is enlarged in one direction (Y direction) so that the image has the same width d₂ as the image 765 indicated in FIG. 35B and the amount of light is doubled so that it is equal to that of the image 763 indicated in FIG. 35A. The light intensity distribution in the image at this time can be represented by a curve 777 indicated in FIG. 36C and a curve 778 indicated in FIG. 37.

Now an embodiment of the device for detecting particles of foreign matter on a patterned wafer according to the present invention will be explained more in detail, referring to FIG. 38.

Figure 38:
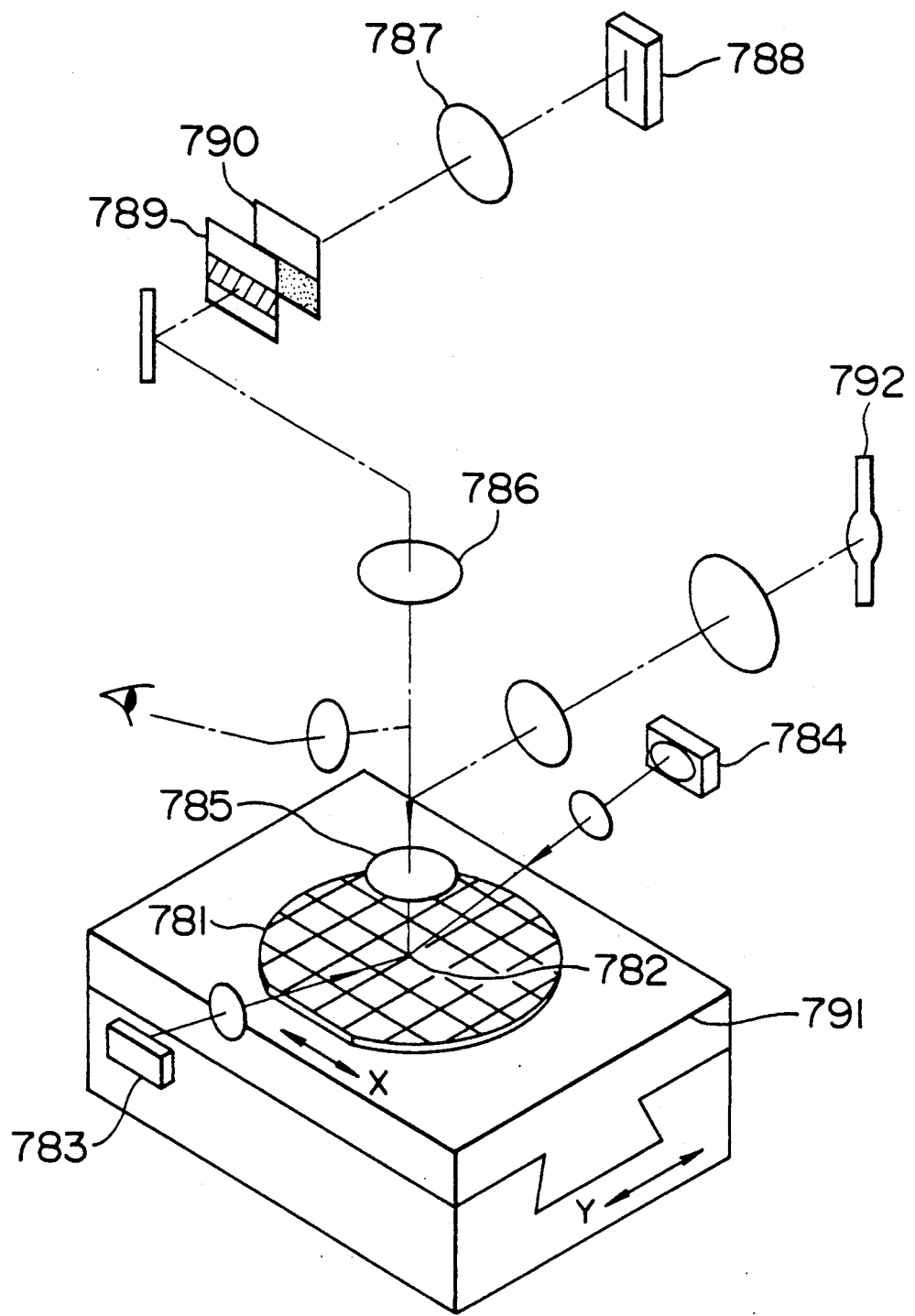
FIG. 38 is a perspective view for explaining a device for detecting particles of foreign matter on a patterned wafer, which is still another embodiment of the present invention.

As indicated in FIG. 38, a small region 782 on a wafer 781 is illuminated obliquely downward by means of S polarized light semiconductor laser devices 783 and 784. The image of this small region 782 is enlarged by an objective lens 785 and detected by a photo-electric converting sensor 788 through a field lens 786 and an enlarging lens 787. There is disposed a light intercepting mask 789 corresponding to the mask 236 described, referring to FIG. 12A, at the position of the real image of the Fourier transformation plane of the objective lens 785. At the same position there is disposed a ½ wave plate 790 intercepting a half of the incident light, corresponding to the mask indicated in FIGS. 36A and 36B. In this state an X-Y stage 791 is moved in th X direction. A lamp 792 is an illuminating device used at observing detected particles of foreign matter with the eye.

Figure 39:
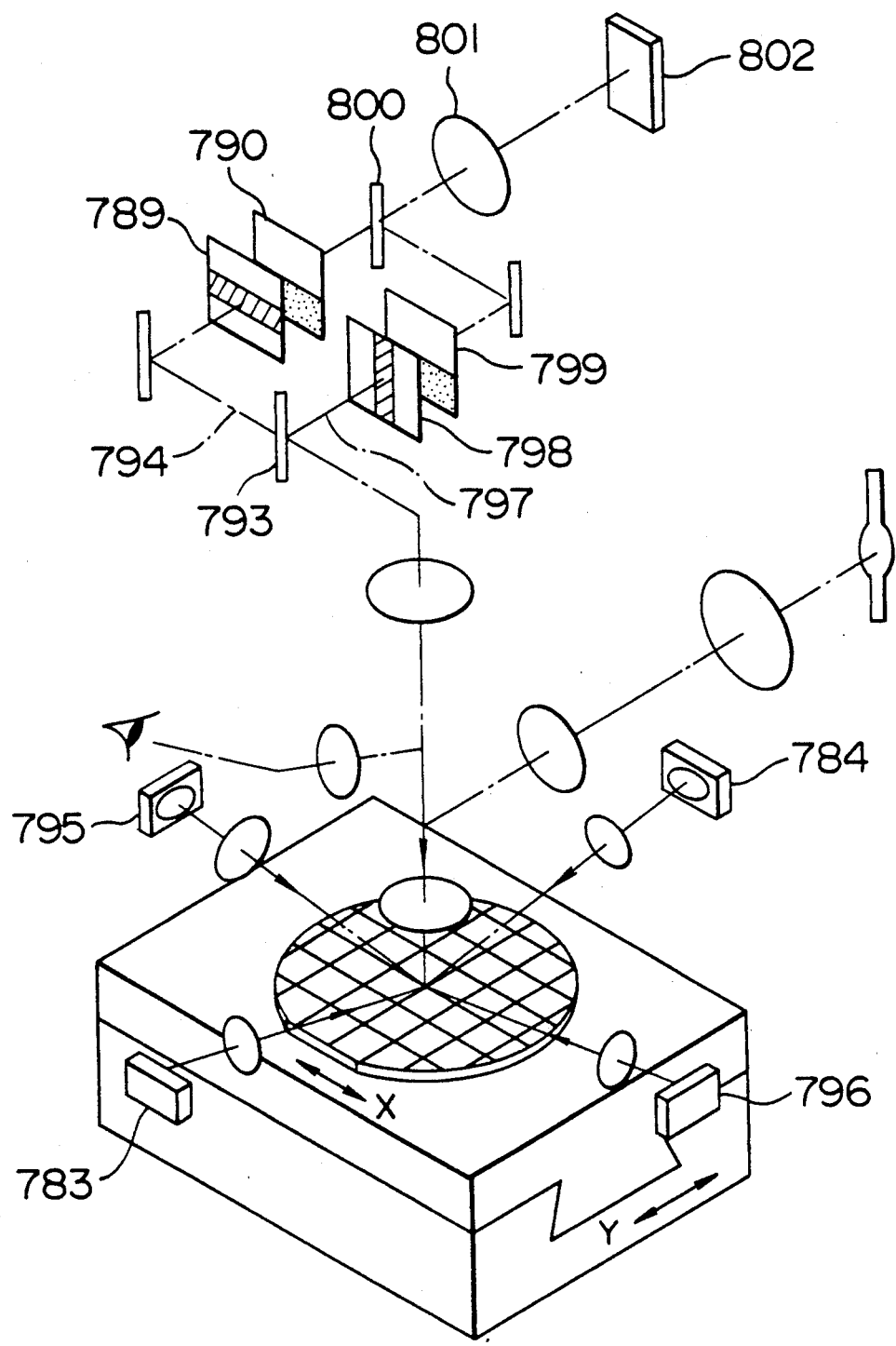
FIG. 39 is a perspective view for explaining a device for detecting particles of foreign matter on a patterned wafer, which is still another embodiment of the present invention.

FIG. 39 shows an embodiment, in which the sample is illuminated in 4 directions around it for the purpose of increasing light scattered by the foreign matter and at the same time reducing the directivity of the scattered light.

In this case S polarized laser light having a wavelength of 780 nm is used for Y direction illuminating semiconductor laser devices 783 and 784. A dichroic mirror 793 transmitting light of 780 nm is disposed in the course, which leads the light to an optical path 794.

Foreign matter signals are extracted through a light intercepting filter 789 and a ½ wave plate 790 covering a half area of the light beam stated, referring to FIG. 38. On the other hand S polarized laser light having a wavelength of 830 nm is used for X direction illuminating semiconductor laser devices 795 and 796. The dichroic mirror 793 reflects the light of this wavelength and the light reaches an optical path 797.

The Fourier transformation images obtained by the Y and the X direction illuminations, respectively, are perpendicular to each other, a light intercepting filter is so disposed that the direction thereof is perpendicular to that of the light intercepting filter 789. A ½ wave plate 799 covering a half area of the light beam for smoothing the real image is inserted in the optical path 797 has the same direction as the ½ wave plate 790. The optical paths 794 and 797 are synthesized by another dichroic mirror 800 into an optical path. After that, light signals are transformed into electric signals by a photo-electric converting sensor 802 through an enlarging lens 801.

In the case where the signal coming from the pattern portion is produced at a position deviated by δ due to errors in the arrangement of the chip, by the prior art method, it is detected by a sensor 745 and an output 746 is taken out, as indicated in FIG. 40D. That is, since the output 746 is produced at a position different from that of an output 734' of a sensor 731' indicated in FIGS. 40A and 40B, a differential electric signal 747' therebetween is taken out as an output 748, as indicated in FIG. 40E. Since this output 748 is higher than a threshold value 740, it is judged that there is foreign matter, which is clearly an erroneous judgment.

According to the present invention, when the real image is enlarged in the Y direction as indicated in FIG. 41A, the image of the brilliant pattern corner portion is enlarged as indicated by 749 and thus output signals 752 and 753 coming from sensors 750 and 751, respectively, are obtained. On the other hand the image of the pattern corners corresponding to each other in two adjacent chips can be represented by 754, as indicated in FIG. 41C, and output signals 757 and 758 coming from sensors 755 and 756, respectively, are obtained. For this reason absolute values 759 and 760 of differential signals therebetween can be represented, as indicated in FIG. 41E. Since they are sufficiently small with respect to those obtained in the case indicated in FIG. 40E, they are not judged as foreign matter signals.

As described above it is an important point for detecting pattern corners and foreign matter that the real image is enlarged in one direction (Y direction in this case).

Further embodiments of the present invention will be explained below, referring to FIGS. 8 to 17.

At first the fundamental principle of the present invention will be explained. Again the behavior of the light scattered by the pattern 211 and the particles of foreign matter 401 and 402 on the wafer 1 illuminated by the S polarized laser beam will be described, referring to FIGS. 9A to 9E. In FIG. 9A, the spatial frequency region in the objective lens 7, i.e. Fourier transformation plane (corresponding to an emitting pupil), is imaged by the field lens 9 at the position indicated by 300. Consequently the Fourier transformation image 213 of the straight line edge portion in the pattern 211 indicated in FIG. 9B, which is perpendicular to the optical axis of the laser beam, and the Fourier transformation image 214 of the foreign matter are obtained at the position indicated by 300 (FIG. 9C). Now attention is paid not only to the difference in the shape between the two Fourier transformation images but also to the polarization state. As indicated in FIG. 9D, the Fourier transformation image 213 of the straight line edge portion is composed approximately only of the S polarization component 218, which is the same as the incident laser beam. On the other hand, as indicated in FIG. 9E, the Fourier transformation image 214 of the particles of foreign matter 401 and 402 is composed of polarization components of various directions.

In this case, if the polarizing plate 220 indicated in FIG. 10A is disposed at the position indicated by 300 to intercept the light of the S polarization component, all the light passing through the polarizing plate 220 is composed of the P polarization component, as indicated in FIG. 10B, and the Fourier transformation image 213 of the straight line edge portion in the pattern 211 composed of the S polarization component is completely removed. In this way it is possible to obtain only the P polarization component in the Fourier transformation image 214 of the particles of foreign matter 401 and 402. However, comparing 219 in FIG. 9A with 230 in FIG. 10B, it can be clearly seen that the amount of the light coming from the particles of foreign matter 401 and 402 is remarkably reduced.

On the other hand, in the case where the spatial filter 221 indicated in FIG. 10C is disposed similarly at the position indirected by 300 in FIG. 9A, although the Fourier transformation image 213 of the straight line edge portion can be removed, as indicated in FIG. 10D, a part of the Fourier transformation image 214 of the particles of foreign matter 401 and 402 is also removed at the same time. Further, in the case where the light intercepting portion 222a of the spatial filter 222 is great, as indicated in FIG. 10E, the Fourier transformation image 214 of the particles of foreign matter 401 and 402 is also significantly impaired, as indicated in FIG. 10F.

Paying attention to the difference in the shape between the Fourier transformation image of the straight line edge portion in the pattern and the Fourier transformation image of the particles of foreign matter in the spatial frequency region and the difference in the polarization state therebetween, the present invention makes the most of the merits of the two methods by combining the foreign matter detecting method using the polarizing plate with that using the spatial filter. That is, as indicated in FIG. 11A, a spatial filter 233, in which the part (223a indicates the light intercepting portion) corresponding to the Fourier transformation image 213 of the straight line edge portion in the pattern 211 is made of a polarizing plate disposed so as to intercept the light composed of the S polarization component or an optical material 223C varying the polarization state of the incident light and the other part is made of another optical material 223b, which makes the incident light pass through while conserving the polarization state thereof, is disposed at the position indicated by 300 in FIG. 9A. As the result, as indicated in FIG. 11B the light composed of S polarization component is intercepted only at the region corresponding to the Fourier transformation image 213 of the straight line edge portion and all the polarization components can pass through the other region. Consequently only the Fourier transformation image 213 of the straight line edge portion composed of the S polarization component and the S polarization component in the region of the polarizing plate 223C in the Fourier transformation image 214 of the particles of foreign matter 401 and 402 are intercepted and the amount of the foreign matter detecting light is remarkably increased with respect to the method indicated in FIGS. 10A to 10F. Also in the case where the region corresponding to the Fourier transformation image 213 of the straight line edge portion is great, as indicated in FIG. 11D, the amount of the foreign matter detecting light is increased with respect to that obtained by the method indicated in FIG. 10F. In order to distinguish the spatial filter described above from the conventional spatial filter, hereinbelow it is called polarizing spatial filter.

Hereinbelow a fourth embodiment of the present invention will be explained, referring to FIGS. 8A to 8D. In order to have a universality the terminologies, S polarization and P polarization, are not used, but they are called uniformly x direction polarization and y direction polarization instead thereof, referring to x and y axes in the coordinates in the figure.

FIG. 8A is a perspective view of the foreign matter detecting optical system in a fourth embodiment of the present invention. This optical system consists of an x-y stage 202, laser devices 203a and 203b, an objective lens 7, a relay lens 9, a polarizing spatial filter 206 a relay lens 12 and a 2-dimensional solid state imaging element 208. In the figure the sample is a product wafer, on which a circuit pattern is formed. This wafer 1 on the x-y stage 2 is imaged on the 2-dimensional solid state imaging element 208 through the objective lens 7 and the relay lenses 9 and 12. On the other hand the Fourier transformation plane (spatial frequency region) 8 in the objective lens 7 is imaged by the relay lens 9 at a position indicated by 300. The wafer 1 is illuminated obliquely in 2 directions by y direction polarization (S polarization) beams emitted by the laser devices 203a and 203b, which are opposite to each other. FIG. 8B shows an example of the circuit pattern 211 and two particles of foreign matter 601 and 602. As the result of the laser oblique illumination, at the position indicated by 300, i.e. at the position, where the Fourier transformation plane 8 in the objective lens 7 is imaged, a Fourier transformation image 212 of the circuit pattern 211 and the particles of foreign matter 601 and 602 is obtained, as indicated in FIG. 8C. 213 indicates a Fourier transformation image of the straight line edge portion in the circuit pattern 211, which is perpendicular to the optical axis of the laser beams in 2 directions, and it is composed approximately completely of the same y direction polarization component at the incident laser beam. 214 indicates a Fourier transformation image of the particles of foreign matter 601 and 602, which is composed of polarization components in various directions. Therefore a polarizing spatial filter 206 indicated in FIG. 8D is disposed at the position indicated by 300. This polarizing spatial filter 206 has a following construction. That is, the part corresponding to the Fourier transformation image 213 of the straight line edge portion in the pattern is made of a polarizing plate 206C disposed so as to intercept the y direction polarization component and the other part is made of a usual glass plate 206b, which makes the incident light pass through while conserving the polarization state thereof. 206a is a light intercepting portion made of a chromium film for intercepting stray light, etc. Only the y direction polarization component existing in the region of the polarizing plate 206C in the Fourier transformation image 213 of the straight line edge portion composed of the y direction polarization component and the Fourier transformation image 214 of the particles of foreign matter 601 and 602 is intercepted, as indicated in FIG. 11B. As the result, as indicated in a detected image 215 in FIG. 8A, the light scattered by the particles of foreign matter can be detected by the 2-dimensional solid state imaging element 208, almost not impaired. On the other hand, since the light scattered by the pattern corner portion has scattering and polarization characteristics similar to those of the light scattered by the foreign matter, it passes through the polarizing spatial filter 206 and is detected as indicated by 351. With this respect the detected image 215 is compared with a stored image 216 of the same place in an adjacent chip, which is stored in a memory 209 (image obtained by the laser oblique illumination through the spatial filter 206), in the comparing circuit 210 and only the information 601a and 602a of the foreign matter can be extracted by removing the information 351 of the pattern corner portion while obtaining a differential image 217.

As described above, according to the present invention, it is only the y direction component existing in the region in the polarizing plate 206C, which is a considerably small portion of the whole light scattered by the foreign matter, that is intercepted by the polarizing spatial filter. Therefore it is possible to detect still smaller particles of foreign matter, because the amount of the foreign matter detecting light increases and the power of the foreign matter detection doesn't depend on the shape of the pattern and the foreign matter. With respect to the method, by which a conventional polarizing plate is used and all the y direction component is intercepted and to the method, by which all the light scattered by the foreign matter, which exists at the light intercepting portion, is intercepted.

A fifth embodiment of the present invention will be explained below, referring to FIGS. 12A to 12D. Hereinbelow, just as in the fourth embodiment, concerning the polarization direction of the light the terminologies "x direction polarization" and "y direction polarization" are used, referring to the x and y axes in the coordinates in the figure.

FIG. 12A is a scheme illustrating the foreign matter detecting optical system in the fifth embodiment of the present invention. While in the foreign matter detecting optical system in the fourth embodiment indicated in FIG. 8A two laser devices 203a and 203b, which are opposite to each other, are used and the sample is illuminated obliquely in 2 directions, in this embodiment 2 pairs of, i.e. in total four laser devices 203a, 203b, 203c and 203d, two of which are opposite to each other, are used and the sample is illuminated obliquely in 4 directions and corresponding thereto the construction of the polarizing spatial filter is modified. All the construction and the function of the remaining part are identical to those of the fourth embodiment. At first the wafer 1 is illuminated obliquely in 4 directions with linearly polarized beams emitted by the laser devices 203a, 203b, 203c and 203d (the laser devices 203a and 203b emit y direction polarized beams and the laser devices 203c and 203d emit x direction polarized beams). FIG. 12B shows an example of the circuit pattern 211 and particles of foreign matter 601 and 602. As the result, at a position indicated by 300, i.e. at the position, where the Fourier transformation plane 8 in the objective lens 7 is imaged, a Fourier transformation image 350 of the circuit pattern 211 and the particles of foreign matter 601 and 602 is obtained, as indicated in FIG. 12C. 237a represents a Fourier transformation image of the straight line edge portion in the circuit pattern 211, which is perpendicular to the optical axis of the laser beams emitted by the laser devices 203a and 203b, which image is composed principally of the y direction polarization component just as the incident laser beams. 237b represents a Fourier transformation image of the straight lines edge portion in the circuit pattern 211, which is perpendicular to the optical axis of the laser beams emitted by the laser devices 203c and 203d, which image is composed principally of the x direction polarization component just as the incident laser beams. On the other hand, 238 represents a Fourier transformation image of the particles of foreign matter 601 and 602, which image is composed of polarization components of various directions. Then a polarizing spatial filter 236 indicated in FIG. 12D is disposed at the position 300. This polarizing spatial filter 236 has a following construction. That is, the portion corresponding to the Fourier transformation image 237a of the straight line edge portion indicated in FIG. 12C is constituted by a polarizing plate 236c disposed so as to intercept the y direction polarization component, while the portion corresponding to the Fourier transformation image 237b of the straight line edge portion, which is perpendicular to the straight line edge portion stated previously, is constituted by a polarizing plate 236d disposed so as to intercept the x direction polarization component. In the portion, where the 2 polarizing plates 236c and 236d intersect each other, both the x and the y direction polarization components are intercepted. On the contrary, the remaining portion is constituted by a usual glass plate 236b, which makes the incident light pass through them while conserving the polarization state. 236a is a light intercepting portion made of a chromium film for intercepting stray light, etc. Just as for the fourth embodiment, by disposing the polarizing spatial filter 236 at the position 300 it is possible to intercept only the y direction polarization component in the Fourier transformation images 237a and 236b of the straight line edge portions, which are perpendicular to each other, and the Fourier transformation image 238 of the particles of foreign matter 601 and 602 at the region of the polarizing plate 236c and the x direction polarization component therein at the region of the polarizing plate 236d. As the result, as indicated in the detected image 240 in FIG. 12E, the light scattered by the foreign matter can be detected by the 2-dimensional solid state imaging element 208, almost not impaired. Information 351 of the pattern corner portion can be removed alone by comparing the detected image 240 with a stored image 241 of an adjacent chip in the comparing circuit 210 and obtaining a differential image 242 just as for the fourth embodiment. In this way only the foreign matter information 601a and 602a can be extracted.

As described above, according to this embodiment not only the effects identical to those obtained in the fourth embodiment but also following effects can be newly obtained. That is, some foreign matters have directivity in the shape thereof. Therefore, in the case where the sample is illuminated in a restricted direction, the directivity of the scattered light is enhanced and at the worst case there can be cases, where no scattered light enters the objective lens. In this embodiment, since the sample is illuminated obliquely in 4 directions, even in the above cases it is possible to reduce the directivity of the light scattered by the foreign matter and thus to prevent the decrease in the amount of the foreign matter detecting light. Furthermore, for a particle of foreign matter, which sticks to a stepwise portion of the pattern and is in the shadow of the step, when it is illuminated in 2 direction, so that it is difficult to find it, a satisfactory amount of illuminating light can be obtained by the illumination in 4 directions and thus it is possible to prevent overlooking of the foreign matter.

Now a sixth embodiment of the present invention will be explained, referring to FIGS. 13 to 17. The fourth and the fifth embodiments described above are characterized in that information of the circuit pattern is removed by using a polarizing spatial filter constituted by a polarizing plate and a glass plate. The sixth embodiment is characterized in that the above object is achieved by using a polarizing spatial filter formed by using a liquid crystal element. Before explaining concretely this embodiment, the function of this liquid crystal element will be explained more in detail, referring to FIGS. 14 to 16.

Figure 14:
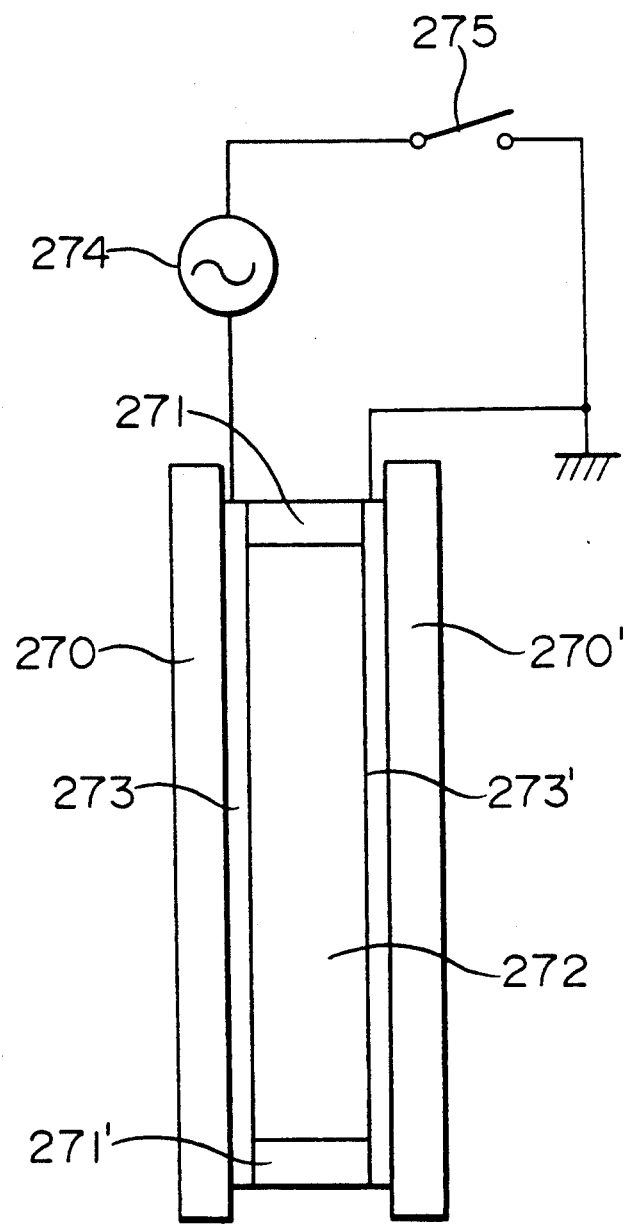
FIGS. 14, 15 and 16 are schemes indicating the construction of a liquid crystal element and the working principle of the element.
Figure 15:
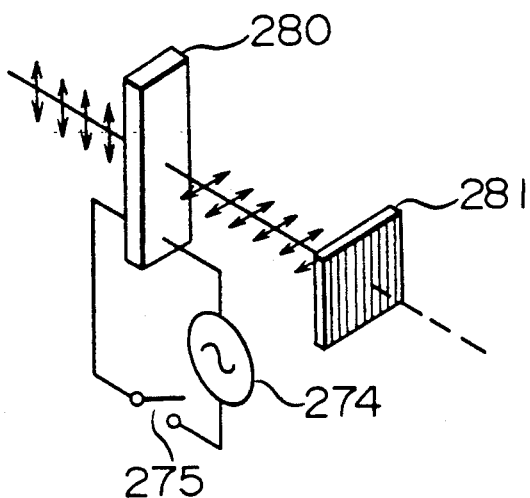
Figure 16:
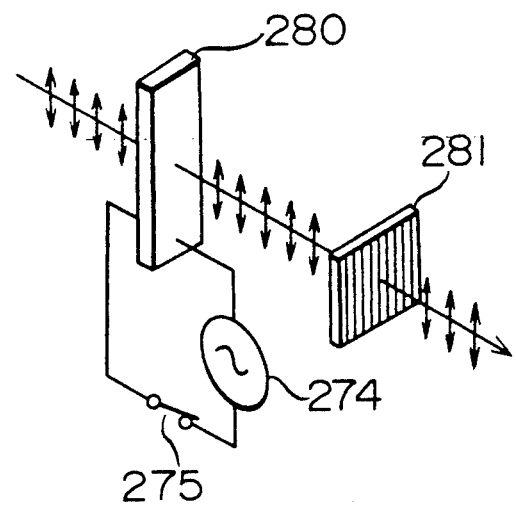

A liquid crystal element is constructed by filling liquid crystal 272 between 2 parallel glass plates 270 and 270', on which transparent electrodes 273 and 273' are printed, and between seals 271 and 271', an AC voltage generated by an AC power source 274 being applied to the transparent electrodes 273 and 273' through a switch 275, as indicated in FIG. 14. When a linearly polarized light beam is injected into this liquid crystal element 280, as indicated in FIG. 15, in the state where the AC power source 274 is turned off by the switch 275, the liquid crystal element 280 acts as an optical rotator, which rotates the polarization direction of the incident light by 90°. On the contrary, on the ON state, as indicated in FIG. 16, the linearly polarized light passes therethrough, as it is. Consequently by disposing a polarizing plate after the liquid crystal element 280 it is possible to intercept and transmit an arbitrary linearly polarized light by turning on and off the switch 275. By disposing a plurality of such liquid crystal elements and combining them with polarizing plates it is possible to construct a flexible polarizing spatial filter capable of intercepting and transmitting an arbitrary linearly polarizing light at an arbitrary region.

Hereinbelow this embodiment, in which a polarizing spatial filter using this liquid crystal element is adopted, will be concretely explained. Further hereinbelow, just as in the fourth and the fifth embodiments, concerning the polarization direction of the light, the terminology "x direction polarization" and "y direction polarization" are used, referring to the x and y axes in the coordinates in the figure.

Figure 17:
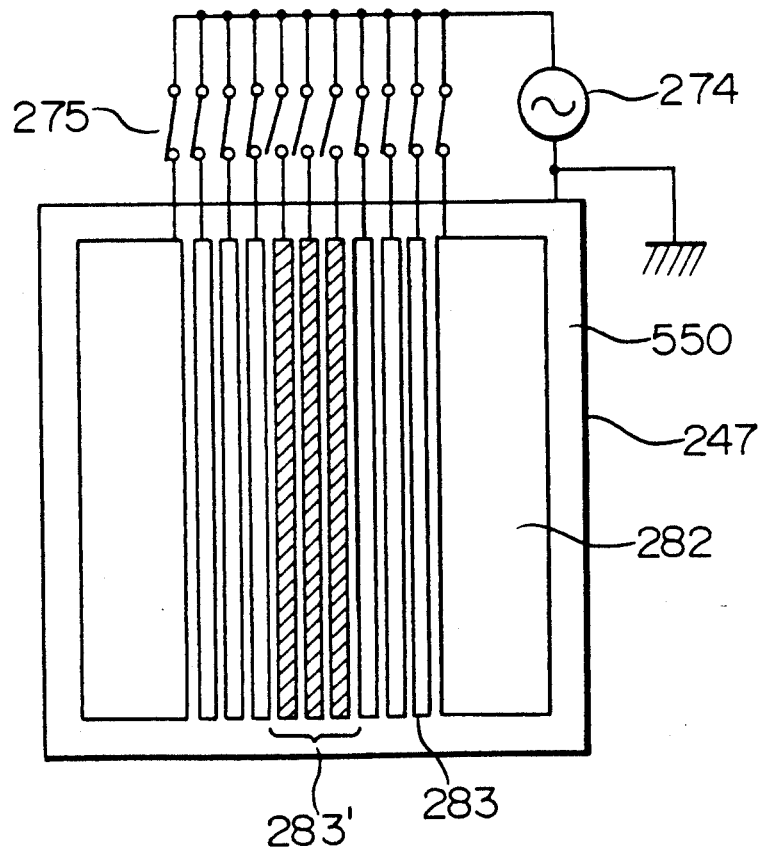
FIG. 17 is an enlarged plan view of a polarizing spatial filter constituted by using the liquid crystal element.

FIG. 13A is a scheme illustrating the foreign matter detecting optical system in this embodiment. This optical system consists of an x-y stage 2, laser devices 203a, 203b, 203c and 203d, an objective lens 7, a relay lens 245, a polarizing beam splitter 246, polarization spatial filters 247 and 247' using liquid crystal elements, polarizing plates 248 and 248', a polarization beam splitter 250, a relay lens 252 and a 2-dimensional solid state imaging element 208. The wafer 1 on the x-y stage 2 is imaged on the 2-dimensional solid state imaging element through the objective lens 7 and the relay lenses 245 and 252. The Fourier transformation plane (spatial frequency region) 208 in the objective lens 207 is imaged at positions 301 and 032 by the relay lens 245. The polarization beam splitter 246 has a function to reflect the y direction polarization component and to transmit the x direction polarization component as it is. On the contrary the polarization beam splitter 350 has a function to reflect the x direction polarization component and to transmit the y direction polarization component as it is. Consequently, as indicated in FIG. 13A, it is possible to synthesize again the light, which has been once separated into the x and the y direction polarization components. At first the wafer 1 is illuminated obliquely in 4 directions by linearly polarized beams emitted by 2 pairs of laser devices 203a, 203b, 203c and 203d, two of which are opposite to each other (the laser devices 203a and 203b emit y direction polarized beams and the laser devices 203c and 203d x direction polarized beams). FIG. 13B shows an example of the circuit pattern 211 and particles of foreign matter 601 and 602. By the laser oblique illumination, at the position indicated by 301, i.e. at the position where the Fourier transformation plane 8 in the objective lens 7 is imaged, a Fourier transformation image 255 of the circuit pattern 211 and the particles of foreign matter 601 and 602 is obtained, as indicated in FIG. 13C. 256 represents a Fourier transformation image of the straight line edge portion in the circuit pattern 211, which is perpendicular to the optical axis of the laser beams emitted by the laser devices 203a and 203b, which image is composed principally of the y direction polarization component 253 just as the incident laser beams. 257 represents a Fourier transformation image of the particles of foreign matter 601 and 602 which is composed originally of polarization components in various directions, but in reality for which only y direction polarization component is obtained by separating it from the composite beam by means of the polarization beam splitter 246. The polarization spatial filter 247 using the liquid crystal element indicated in FIG. 14 is disposed at this position 301. FIG. 17 shows an enlarged plan view of this polarization spatial filter 247. As indicated in the figure, a plurality of transparent electrodes 282, 283 are formed on parallel glass plates 550 and the application of AC voltages 274 thereto is effected selectively by switches 275 corresponding to respective transparent electrodes 282, 283. In this embodiment it is possible to rotate the polarization direction of the Fourier transformation image 256 of the straight line edge portion consisting of the y direction polarization component 253 and the y direction polarization component of the Fourier transformation image 257 of the particles of foreign matter 601 and 602 in the region of the transformation electrode 283', as indicated in FIG. 13C, by 90° and to change it into the x direction polarization component, as indicated by 258 and 259 in FIG. 13D, by turning off only the switches 275 for the transparent electrodes 283' corresponding to the Fourier transformation image 256 of the straight line edge portion. Consequently, if a polarizing plate 248 is disposed behind the polarizing spatial filter 247 so as to intercept the x direction polarization component, the Fourier transformation image 256 of the straight line edge portion changed into the x direction polarization component and the part changed into the x direction polarization component in the Fourier transformation image 257 of the particles of foreign matter 601 and 602 are removed, as indicated by 260 and 261 in FIG. 13E.

On the other hand, at another imaging position 302 of the Fourier transformation plane 8 in the objective lens 7 a Fourier transformation image 292 is obtained in a similar manner as indicated in FIG. 13F. 293 represents a Fourier transformation image of the straight line edge portion in the circuit pattern 211, which is perpendicular to the optical axis of the laser beam emitted by the laser devices 203c and 203d, which image is composed principally of the same x direction polarization component as the incident laser beam. 294 represents a Fourier transformation image of the particles of foreign matter 601 and 602, which is composed originally of polarization components in various directions, but from which only the x direction component 291 is separated to be obtained by a polarization beam splitter. At this position indicated by 302 there is disposed a polarization spatial filter 247', which is the same as the polarization spatial filter 247 disposed at the position indicated by 301, but rotated by 90° with respect to the latter. Polarization plate 248' is disposed similarly rotated by 90° behind the polarization spatial filter 247. The function of the two filters is completely identical to that disposed at the position indicated by 301. At first the Fourier transformation image 293 of the straight line edge portion which is composed of the x direction polarization component 290, and the x direction polarization component existing in the region of the transparent electrode 283' in the Fourier transformation image 294 of the particles of foreign matter 601 and 602 are rotated by 90° by means of the polarization spatial filter 247' so as to be the y direction polarization component, as indicated by 295 and 296 in FIG. 13G. Then the Fourier transformation image 293 of the straight line edge portion, which is changed into the y direction polarization component, and the part of the Fourier transformation image 294 of the particles of foreign matter 601 and 602, which is changed into the y direction polarization component, are removed by the polarizing plate 248', as indicated by 297 and 298 in FIG. 13H. The y direction polarization component 261 (FIG. 13E) and the x direction polarization component 298 (FIG. 13H) thus obtained in the light scattered by the foreign matter are synthesized by the polarization beam splitter 250. In this way only the light scattered by the foreign matter can be detected, as indicated by 299 and 399 in FIG. 13I, with the polarization components, which are not so seriously impaired. Since the removal of the remaining information of the pattern corner portion is completely identical to that described in the preceding two embodiment, explanation thereof is omitted. This embodiment is characterized in that it is prevented to impair seriously the light scattered by the foreign matter owing to the fact that the scattered light coming from the pattern 211 and the particles of foreign matter 601 and 602 is separated into two polarization components, which are synthesized again after having removed the pattern information from each of them by means of the polarization spatial filters 247 and 247' and the polarizing plates 248 and 248'. According to the present invention not only the same effects as those of the preceding two embodiments are obtained as a matter of fact, but also, since a polarization spatial filter using a liquid crystal element indicated in FIG. 17 is adopted, even if the size of the Fourier transformation images 256 and 293 is changed, the pattern information in an arbitrary region can be surely removed by changing the region, for which the switches 275 are turned off, corresponding thereto and thus it is possible to maintain a high power for detecting the foreign matter. Furthermore the same effects as those of the first and the second embodiments can be obtained also by using a polarization spatial filter constituted by a ½-wave plate instead of the liquid crystal element.

Although a semiconductor wafer is used as the sample in the above described embodiment the present invention can be applied satisfactorily well to foreign matter detection on a reticle, a mask or another semiconductor element or substrate.

As explained above, according to the present invention, the light scattered by the foreign matter, which is impaired at the removal of the pattern information, is only considerably small part of the polarization components and the amount of the foreign matter detecting light is therefore remarkably increased. In addition, since the power for detecting the foreign matter doesn't depend on the shape of the pattern and the foreign matter, together with the increase in the amount of the foreign matter detecting light, it becomes possible to detect still smaller particles of foreign matter and thus an effect to increase the reliability and the fabrication yield of semiconductor devices can be obtained.

The embodiments of the present invention include the following features for detecting still smaller particles of foreign matter.

The first feature consists in that there is disposed an optical system focusing light one-dimensionally such as a cylindrical lens, etc. in the downward illuminating system and stripe-shaped downward illumination is effected on the sample.

Another feature consists in that laser scattered light is reflected by a reflecting mirror so that it doesn't return to the laser light source.

Still another feature consists in a foreign matter detecting device characterized in that it is provided with an illuminating optical system for illuminating the sample with light; a focusing lens system for focusing light reflected by the sample; a plurality of detecting optical systems separating the light obtained by the focusing lens system into partial light beams having different characteristics, each of which includes a one-dimensional solid state imaging element, which makes separated light correspond to pixels and transforms it into electric signals; driving means for driving the one-dimensional solid state imaging element in each of the detecting optical systems so as to output synchronous signals, corresponding to the pixels; adding means for adding the signals outputted synchronously by the driving means; quantizing means for quantizing an output signal obtained by the adding operation by means of the adding means; and detecting means for detecting the foreign matter on the basis of the signal quantized by the quantizing means.

A feature of the present embodiments consists in that mechanical scanning means is made unnecessary so that the whole device is simplified by effecting stripe-shaped downward illumination on the sample by means of a downward illuminating system.

Further, since the device for detecting foreign matter according to an embodiments of the present invention is provided with a plurality of detecting optical systems separating the light reflected by the sample into partial light beams having different characteristics, each of which includes a one-dimensional solid state imaging element, which makes separated light correspond to pixels and transforms it into electric signals; driving means for driving the one-dimensional solid state imaging element in each of the detecting optical systems so as to output synchronously signals, corresponding to the pixels; and adding means for adding the signals outputted synchronously by the driving means, it is possible to increase remarkably the sensitivity of the foreign matter detection.

Hereinbelow the present invention will be explained on the basis of an embodiment indicated in FIGS. 21 to 28B. A downward illuminating system B effecting stripe-shaped downward illumination on the substrate 1 consists of a laser light source 501, a focusing lens 502, a polarizing prism 503, a field lens 504, a ¼ wave plate 505, an objective lens 506, a cylindrical lens 514 and a reflecting mirror having a slit at its central portion. The obliquely illuminating optical system A illuminating obliquely the substrate 1 consists of a laser light source 520 and a focusing lens 519. A detecting system C consists of a light intercepting plate 518 having a light interception portion 518a intercepting the 0-th order diffraction light, an imaging lens 509 and a one-dimensional solid state imaging element 510a. A detecting system D is so constructed that the scattered light reflected by the reflecting mirror 515 is collected by the imaging lens 516 and imaged by the one-dimensional solid state imaging element 517.

By the construction described above the scattered laser light 512a is reflected by the reflecting mirror 515 so that it doesn't enter the laser light source 501, which makes the laser output stable. On the other hand the scattered light 512a reflected by the reflecting mirror 515 is detected by the detector 517 consisting of the one-dimensional solid state imaging element, which increases the sensitivity of the foreign matter detection.

Further, since there is disposed a cylindrical lens 514, which is an optical element focusing one-dimensionally, in the downward illuminating system B and the laser illumination light 511 is focused in a straight-line-shaped spot 511f on the sample 1, no means for sweeping the beam in the Y-direction is necessary.

Furthermore, owing to the fact that there is disposed the obliquely illuminating optical system A and in this way the light scattered by the foreign matter is detected simultaneously by the detectors 510a and 517, it is possible to detect stably considerably small particles of foreign matter, which would produce slightly scattered light, if the were illuminated only by the downward illuminating system B.

As described above, in the downward illuminating system B, when the laser light beam 511 produced by the laser light source 501 and the focusing lens 502 passes through the cylindrical lens 514, it forms a straight-line-shaped laser spot 511c at the gap portion in the reflecting mirror 515. Here the gap portion is slightly wider than the spot 511c. Further the laser light beam 511 forms a straight-line-shaped spot 511d within a diaphragm 504a in the field lens 504 and a straight-line-shaped spot 511e within a diaphragm 506a in the objective lens 506. It is focused into a straight-line-shaped spot 511f on the sample after having passed through the objective lens 506.

This impact is indicated in FIGS. 22A to 22F.

In the case where no foreign matter exists on the sample 1, the reflected light 511 returns to the polarizing prism 503 along the optical path completely identical to that of the illumination light 11. Here for the reason described above the reflected light 511 reflected by the polarizing prism 503 is intercepted by the straight-line-shaped portion 518 in the light intercepting plate 518 disposed in the optical path C.

In the case where the image of a particle of foreign matter on the sample exists at an end portion of the straight-line-shaped spot, the imaging of the light 512 scattered by this particle will be explained, referring to FIGS. 23A to 23G.

The scattered light 512 is extended all over the diaphragm 506a and forms an image 512d in the diagram 504a after having passed through the objective lens 506.

A part 512b of the scattered light 512 reflected by the polarizing prism 503 forms an image 512f on the detector 510a through the focusing lens 509 after having passed through the light intercepting plate 518. In this case all the scattered light 512b passes through the transparent portion outside of the straight-line-shaped portion 518a in the light intercepting plate 518. This is because the scattered light 512b is diffraction light, whose order is higher that 1, and the extent thereof is distributed outside of the distribution 518a of the O-th order diffraction light (reflected light 511 coming from the surface of the sample).

A part 512a of the scattered light 512, which passes through the polarizing prism 503 is reflected by the reflecting mirror 515 and forms an image 512f on the detector 517 through the imaging lens 516 disposed in the optical path D. Here, since all the scattered light 512a is reflected by the reflecting mirror 515, there exists no laser light returning to the light source 501.

Figure 24:
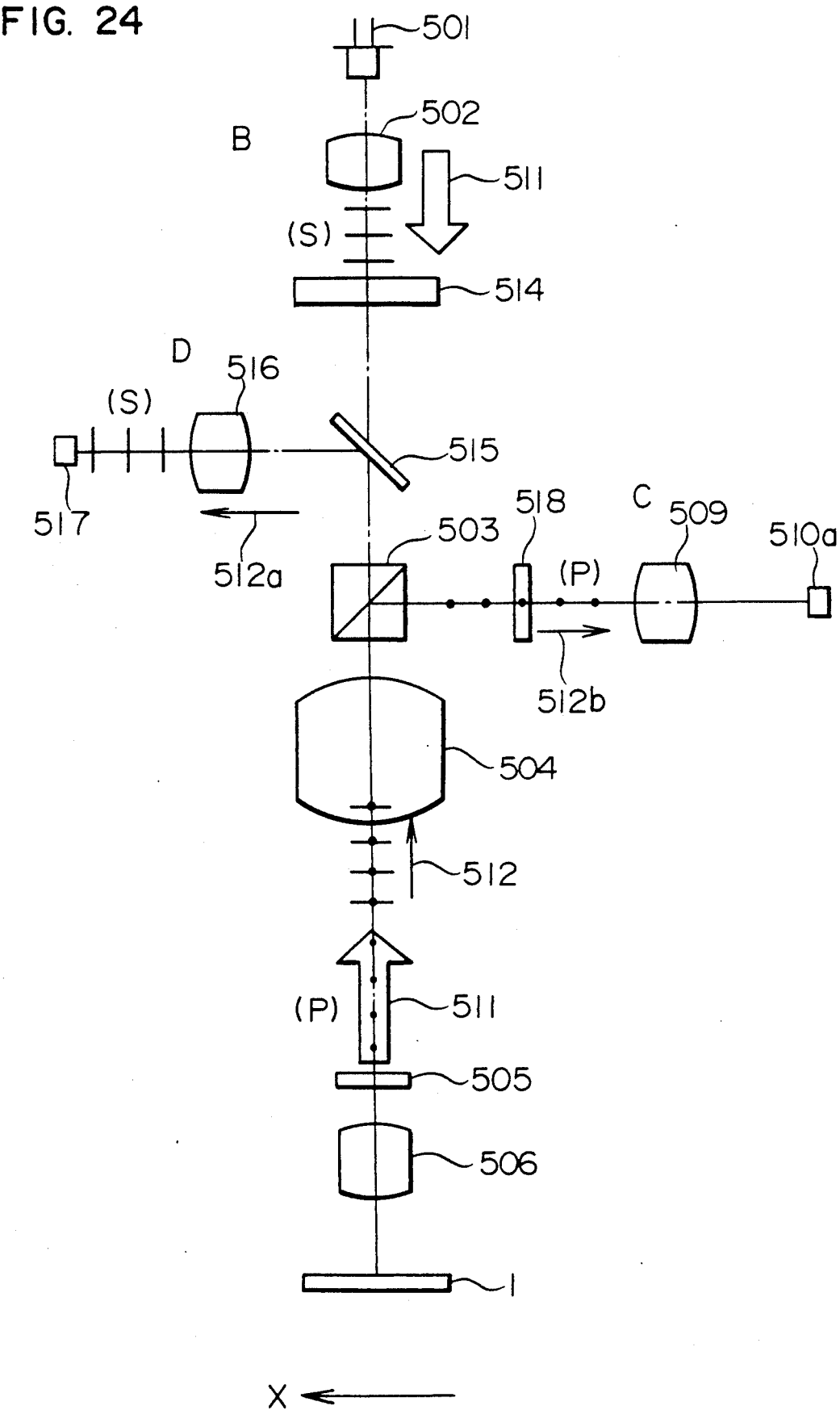
FIGS. 24 is a scheme of the optical path indicating the state of the polarization in the light paths indicated in FIGS. 22 and 23.

The polarization state of the illuminating light 511, the reflected light 511 and the scattered light 512 indicated in FIGS. 21 to 23G are summarized in FIG. 24.

The downward illuminating light 511 is S polarized light (light linearly polarized in the X direction) and the light 511 reflected by the surface of the sample 1 is P polarized light (light linearly polarized in the Y direction). The operation of the ¼-wave plat at this time has been described previously. The light 512 scattered by the foreign matter is composite light of S polarized light and P polarized light. Thus the scattered light 512b reflected by the polarizing prism 503 and the scattered light 512a reflected by the reflecting mirror 515 reach the detectors 510a and 517, respectively.

Figure 21:
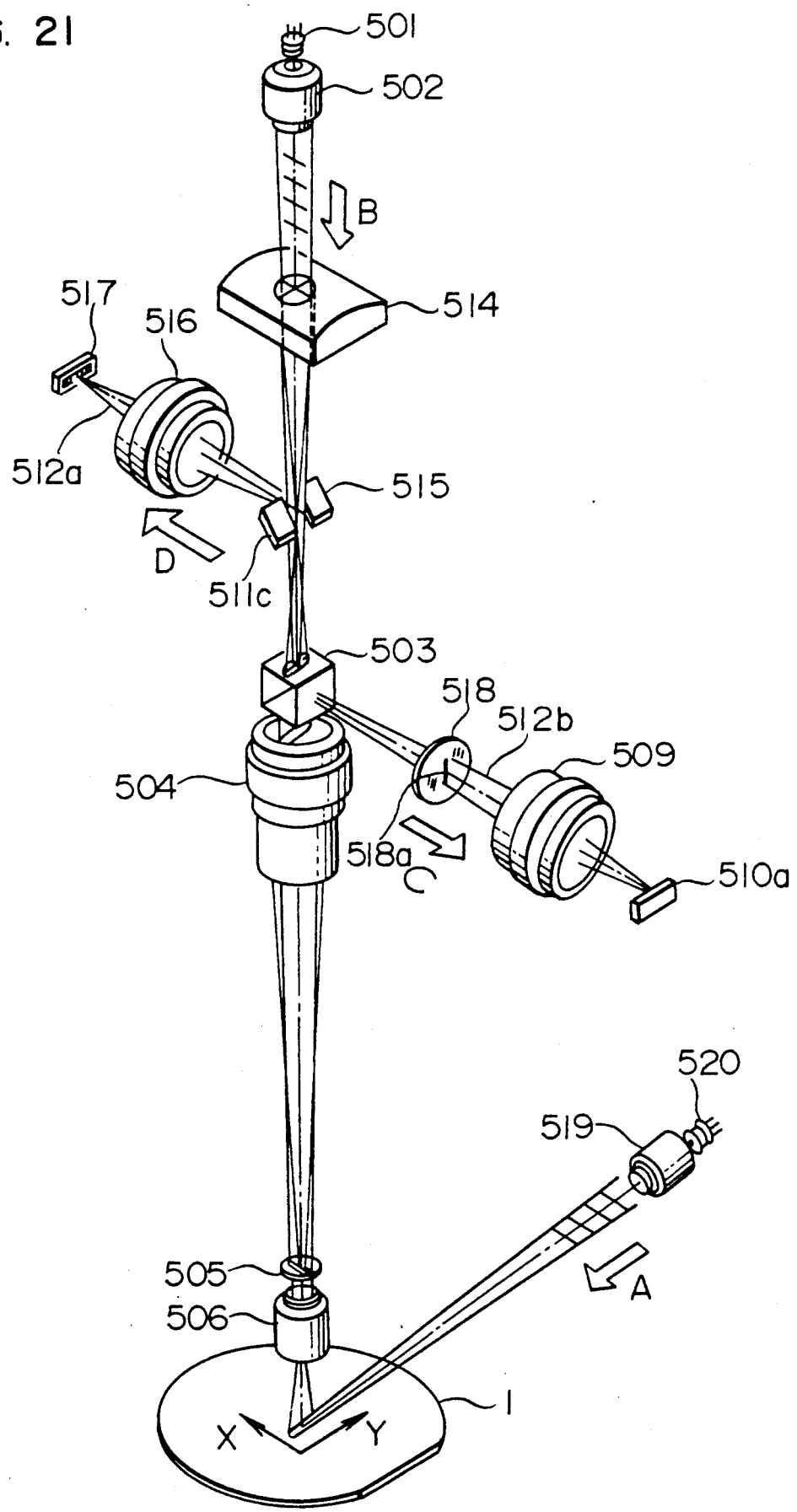
FIG. 21 is a perspective view illustrating an embodiment of the device for detecting foreign matter according to the present invention.
Figure 25A:
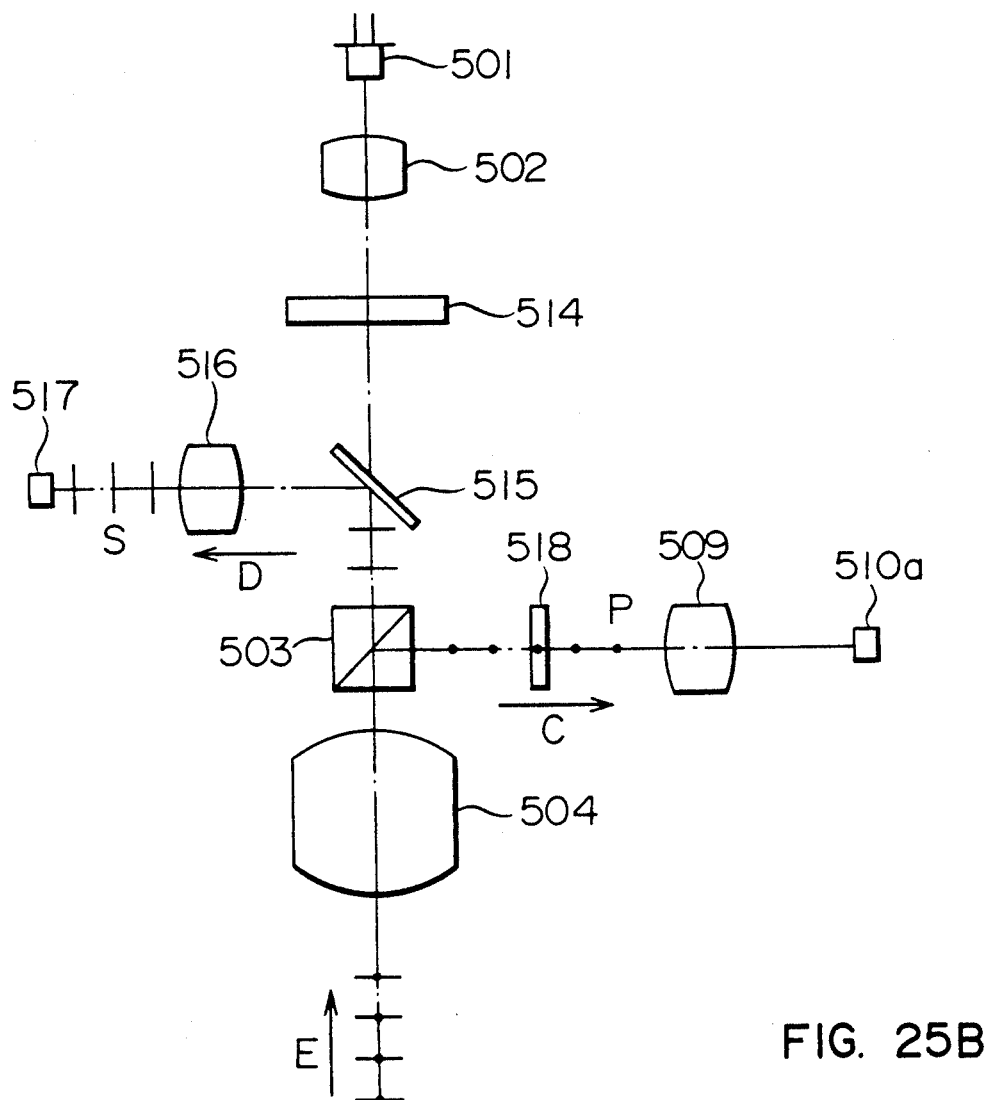
FIGS. 25A and 25B are schemes of the optical path indicating the state of the polarization for detecting the light scattered by the foreign matter by means of the oblique illumination system A indicated in FIG. 21.
Figure 25B:
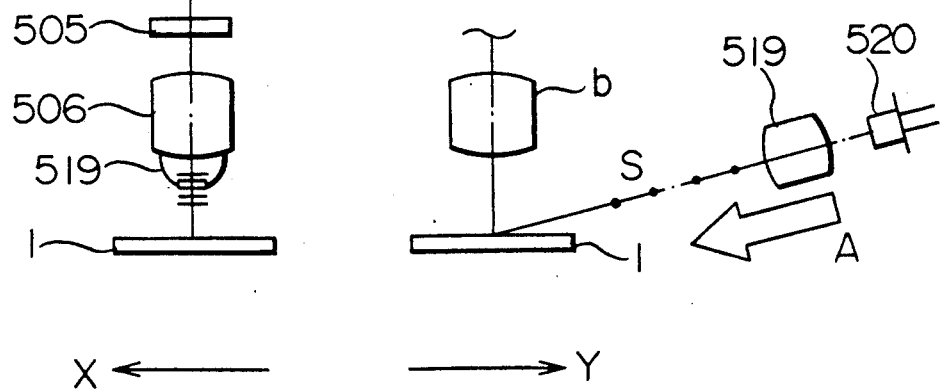

Now the effect of the obliquely illuminating optical system A will be explained, referring to FIGS. 21, 25A and 25B. FIG. 25A is a plan view of a foreign matter detecting device and FIG. 25B is a side view thereof.

The downward illumination B alone is not sufficient for obtaining stably the light 512 scattered considerably small particles of foreign matter having various shapes, whose size is about 1 μm. Therefore it is necessary that the oblique illumination A is added thereto so that a second straight-line-shaped laser light spot is formed at the same position on the sample 1 as the straight-line-shaped laser light spot 511f and that the light 512 scattered by the foreign matter is detected simultaneously by the detecting systems C and D.

As described above, it is possible to reduce overlook of the foreign matter by illuminating the same position on the sample 1 simultaneously with the downward illumination B and the oblique illumination A and detecting the light 512 scattered by the surface of the sample with a high efficiency by means of the detecting systems C and D.

Figure 26:
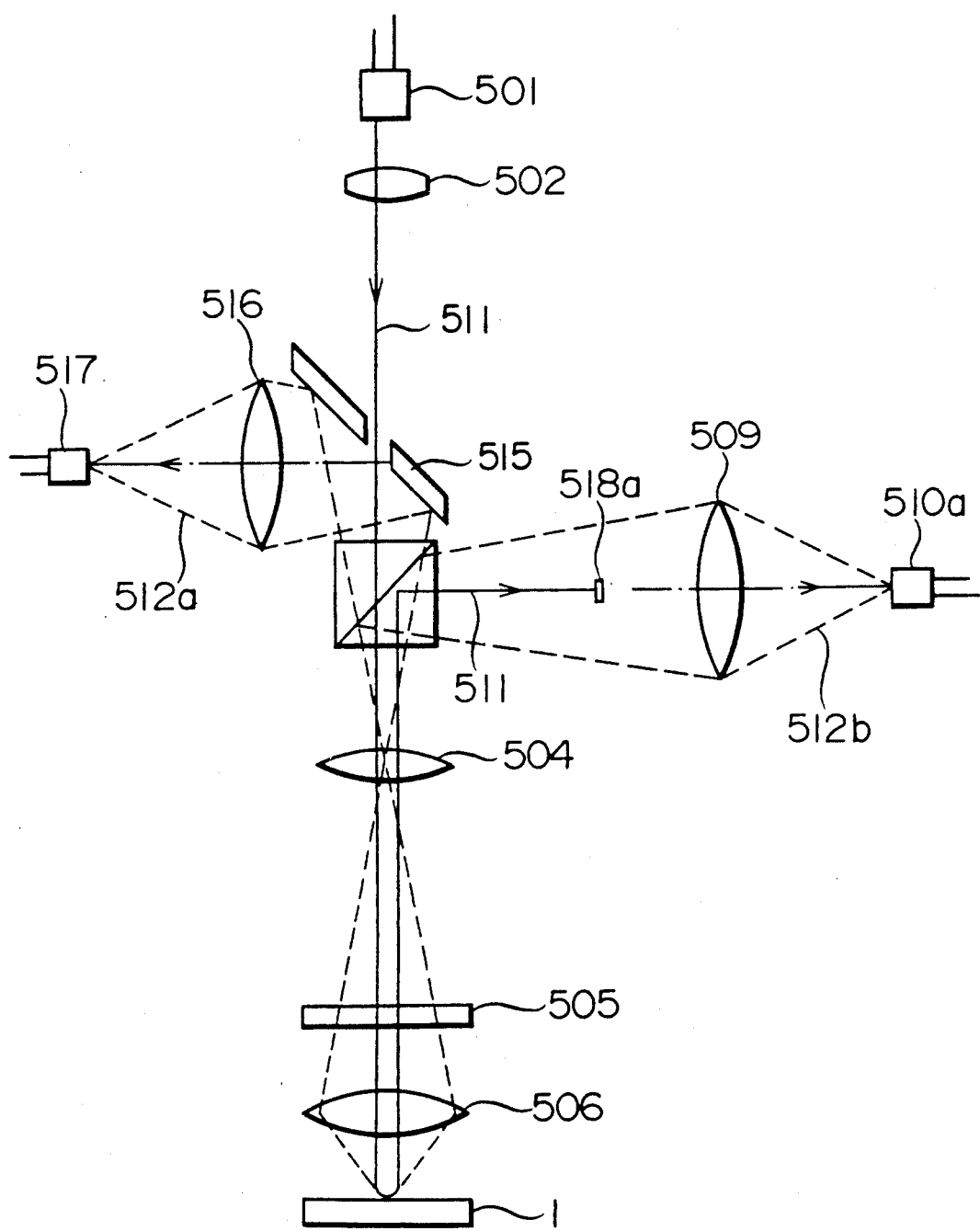
FIGS. 26 and 27 are schemes for explaining the merit, in the case where the light scattered by the foreign matter is detected by means of two different detectors.
Figure 27:
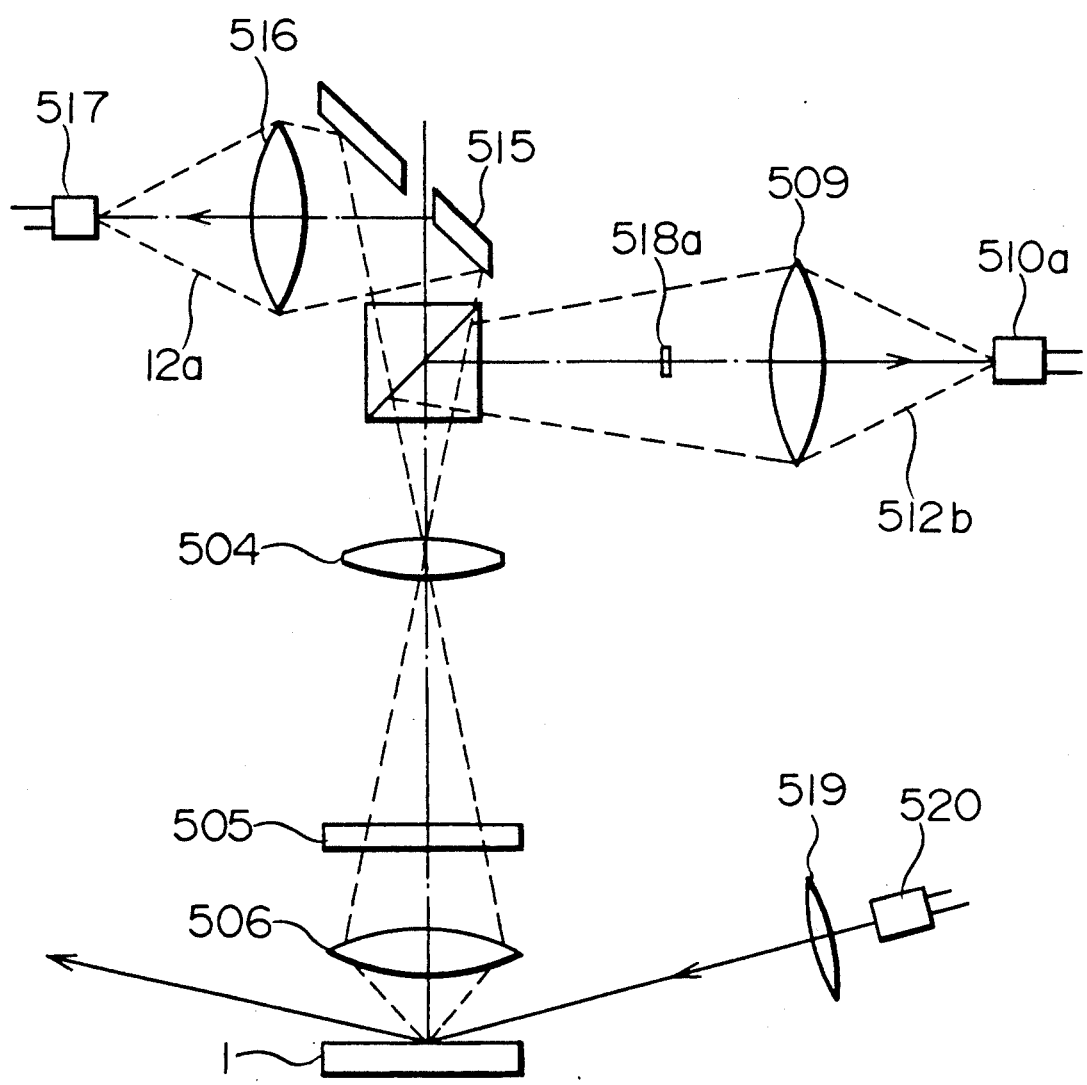

The principal points described above will be summarized as follows, referring to FIGS. 26 and 27. In FIG. 26 the light 511 reflected by the sample 1 coming from the downward illumination light 511 is indicated by a full line and the light 512 reflected by the foreign matter 513 is indicated by a broken line. The reflected light 511 is completely intercepted by the light intercepting plate 518 and all the scattered light 512 reaches the detectors 510a and 517. In the same way FIG. 27 indicated how the light 512 scattered by the foreign matter coming from the oblique illumination A reaches the detectors 510a and 517.

As described above, according to the present invention, since it is possible to detect the light scattered by the foreign matter 513 coming from the downward illumination B and the oblique illumination A and to intercept completely the light reflected by the surface of the sample, the sensitivity of the foreign matter detection is remarkably increased with respect to the prior art techniques.

Now the reason why the downward illumination B and the oblique illumination could be used simultaneously for the foreign matter detection according to the prior art techniques will be explained below. In a prior art device since the laser light spot 511c on the sample is punctual, means for sweeping the laser light beam is disposed on the illumination optical path B or A. However, in order to use the illuminations B and A at the same time, it is necessary to synchronize the sweeping in the optical path B and the sweeping in the optical path A so that no deviation between the two laser light spots 511c on the sample should be produced. This is difficult by the prior art method described above.

According to the present invention there is disposed one-dimensional solid state imaging elements 510a and 517, which are photo-detectors at imaging positions of the straight-line-shaped laser spot 511f, which elements are scanned in synchronism with each other. The problem stated above has been solved in this way. This can be simply realized by scanning the two elements in the Y direction by means of a common driving circuit.

Furthermore it is possible to scan the sample two-dimensionally by combining the the straight-line-shaped laser light spot with the translation of the stage on which the sample 1 is mounted, in the X direction.

Figure 28B:
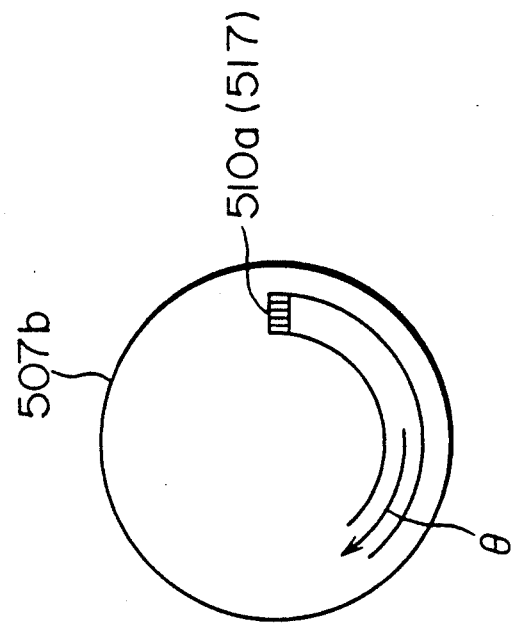
FIGS. 28A and 28B are schemes illustrating a method, by which the sample is transferred in the device indicated in FIG. 21.
Figure 28A:
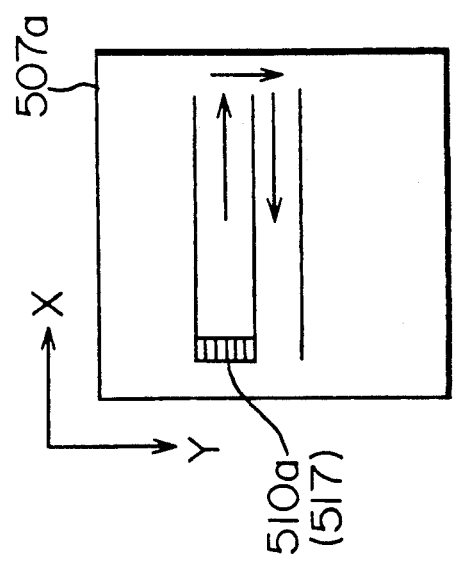

In the case where the sample 507a is rectangular, as indicated in FIG. 28A, the sample 507a is forwarded in zigzags in the X and Y directions. In the case where the sample 507b is circular, as indicated in FIG. 28B, the longitudinal direction of the straight-line-shaped laser spot 511f is set to be in accordance with the radial direction of the sample 507b and the sample 507b is moved helically in the $\theta$ direction.

As described above, since it is possible to reduce the number of scans in the $X(\theta)$ direction with respect to the number required in the case where the sample is scanned with the conventional point-shaped laser light spot 511c, by forming the laser light spot 511f in a straight line shape, the scanning speed in the $X(\theta)$ direction can be reduced. In this way another advantage can be obtained that the response speed required for the automatic focusing function (not shown in the figure) is reduced.

Now the advantage of the use of the two detectors (one-dimensional solid state elements) 510a and 517 will be explained, referring to FIGS. 29A to 29C and 30.

Figure 29A:
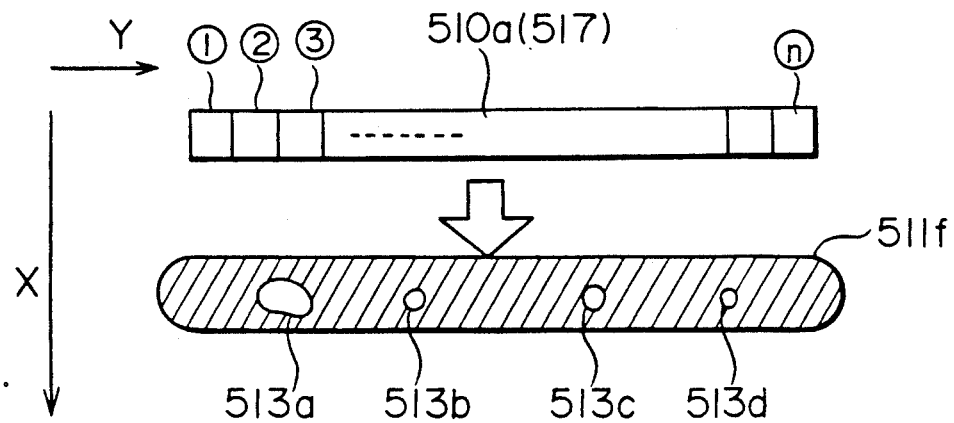
FIG. 29A is a scheme illustrating the relation between the foreign matter and the detector in the device indicated in FIG. 21.
Figure 29B:
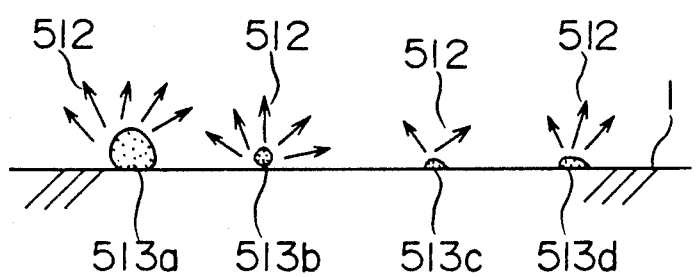
FIG. 29B is a side view indicating the light scattered by the foreign matter.
Figure 29C:
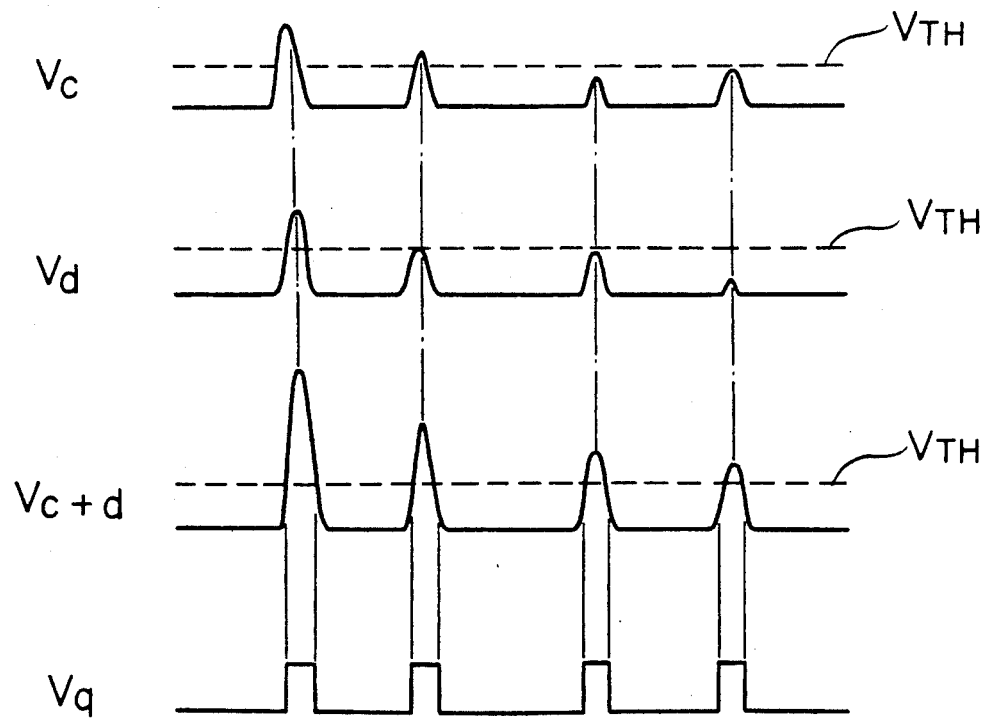
FIGS. 29C is a scheme indicating image signal waveforms obtained by the detector, an added image signal waveform thereof and a two-valued signal waveform, for which the last is transformed into 2 values by a predetermined threshold value.

In the case where there exist particles of foreign matter 513a to 513d on one line in the Y direction, as indicated in FIG. 29A, when the sample 1 is forwarded in the X direction, the scattered light 512 coming from the particles 513a to 513d is produced by the laser spot 511f, as indicated in FIG. 29B. Since the scattered light is focused on pixels ①  to  ⓝ  in the detector 510a, as indicated in FIG. 29A, the output $V_c$ from the detector 510a indicated in FIG. 29C and the output $V_d$ from the detector 517 indicated in FIG. 29C are obtained by scanning the pixels ①  to  ⓝ . However, in the case where the outputs $V_c$ and $V_d$ are quantized independently, outputs due to considerably small particles of foreign matter 513c and 513d are lower than the threshold value $V_{TH}$ and therefore not detected.

Consequently, if the output $V_c$ and $V_d$ are added to each other to form an output $V_{c+d}$, as indicated in FIG. 29C, and the sum thus obtained is quantized by using the threshold value $V_{TH}$, overlook of the particles of foreign matter 513c and 513d by using a quantization signal $V_q$ doesn't occur.

Figure 30:
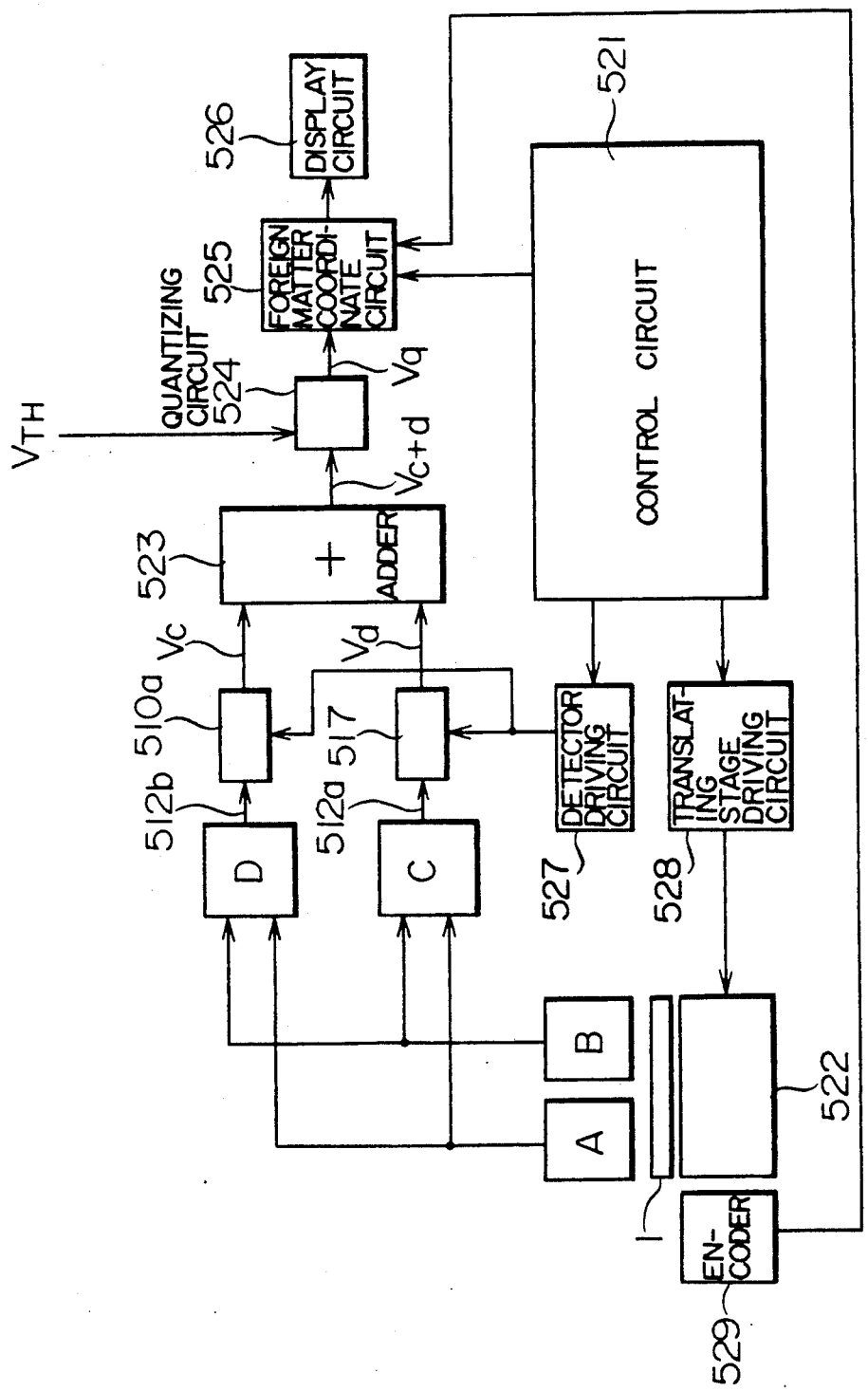
FIG. 30 is a scheme of construction illustrating an embodiment of the signal processing device connected with the device indicated in FIG. 21.

FIG. 30 indicates an embodiment, in which characteristics of the present invention stated above are utilized.

A control circuit 521 sends instructions to a detector driving circuit 527 and a translating stage driving circuit 528. An encoder 529 is mounted on the translating stage 522 and sends coordinates representing the position of the sample 1 to a foreign matter coordinate memory circuit 525.

The outputs $V_c$ and $T_d$ of the detectors 510a and 517 are subjected to an addition operation in an adding circuit 523 to obtain the signal $V_{c+d}$.

The signal $V_{c+d}$ is transformed into a binary value in a quantizing circuit 524 to obtain a quantized signal $V_q$.

When the signal $V_q$ is generated, the coordinate outputs of the encoder 529 are stored in a memory circuit 525. When examination is terminated, the coordinates of the particles of foreign matter are transmitted to a displaying circuit 526 and a foreign matter map is displayed.

As explained above, according to the present invention it is possible to detect stably the considerably small particles of foreign matter on the surface of LSI mirror-polished wafers, row material of the face plate for magnetic disks, etc.

In the above explanation has been made by using series output type elements such as CCD (Charge Coupled Device) for the one-dimensional solid state imaging elements 510a and 517.

Further, if parallel output type elements as disclosed in JP-A-61-104242, JP-A-61-104659, and JP-A-61-104658 are used, it is possible to try to increase further the sensitivity of the foreign matter detection and the reliability. In this case, it is necessary to effect wiring from each of the pixels in the elements 510a and 517 to adding circuits 523-l to 523-n and to dispose n quantizing circuits 524-l to 524-n.

Figure 31:
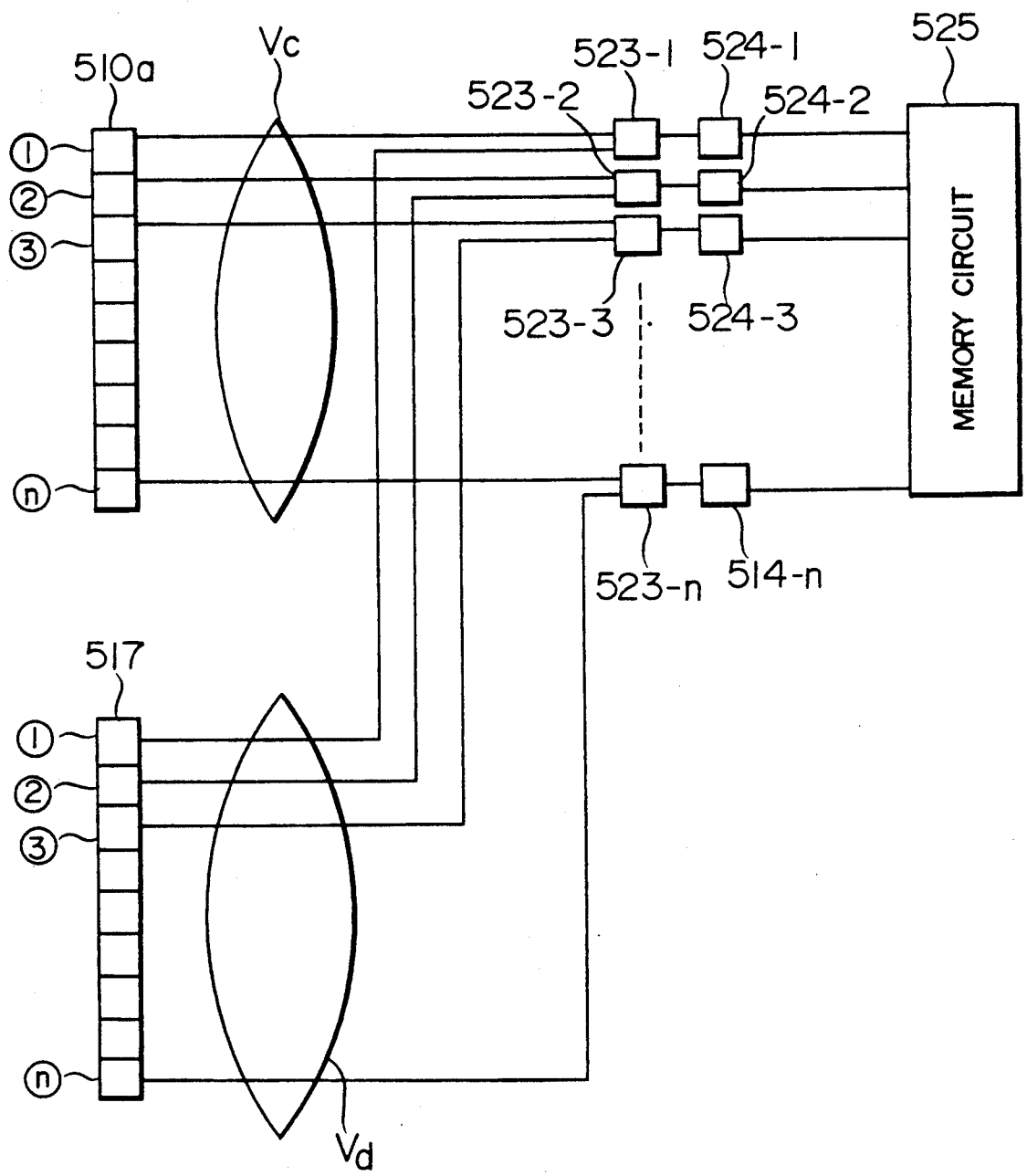
FIG. 31 is a scheme of construction illustrating another embodiment of the device indicated in FIG. 30.
Figure 32:
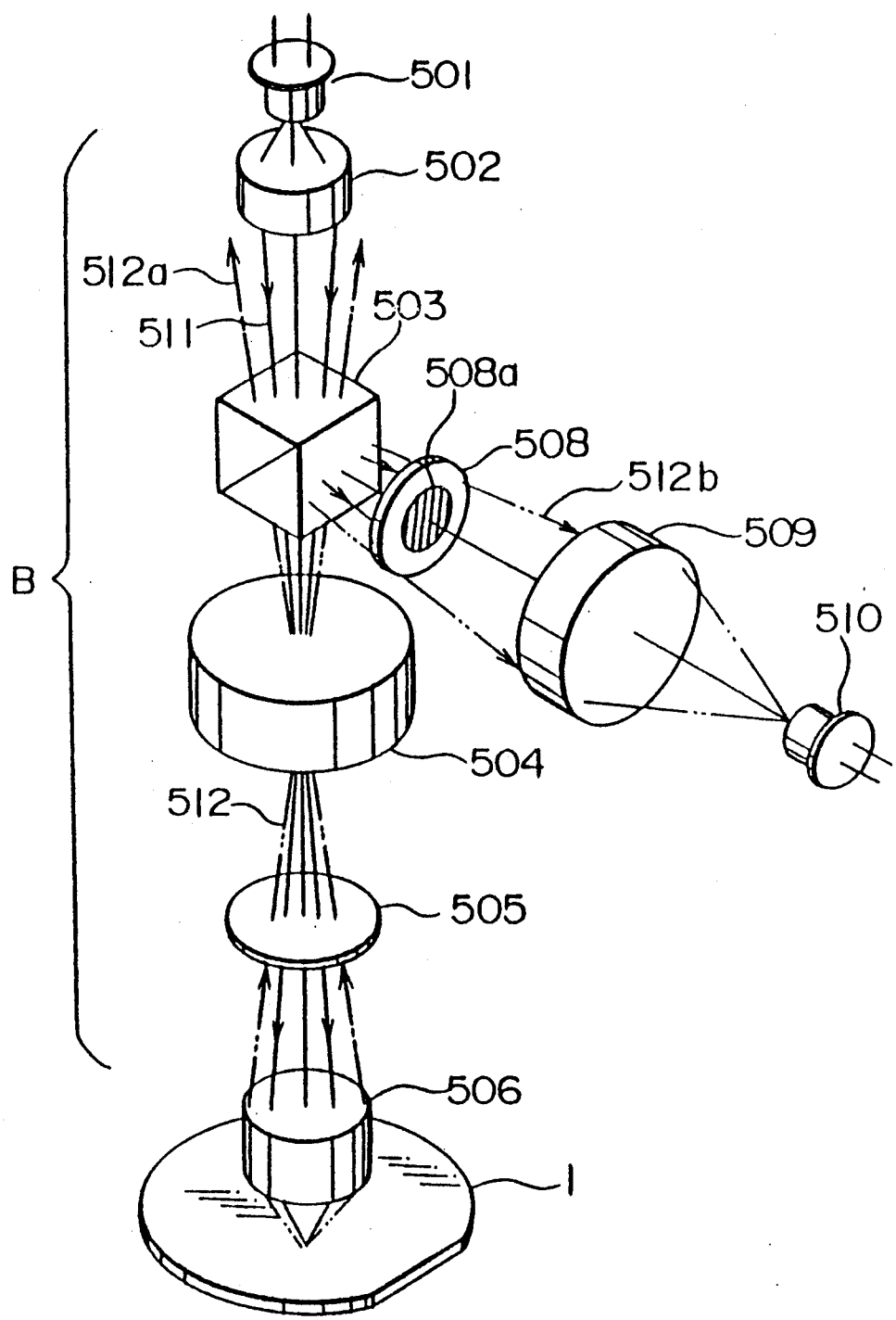
FIG. 32 is a perspective view illustrating a device for detecting foreign matter according to the prior art technique.
Figure 33:
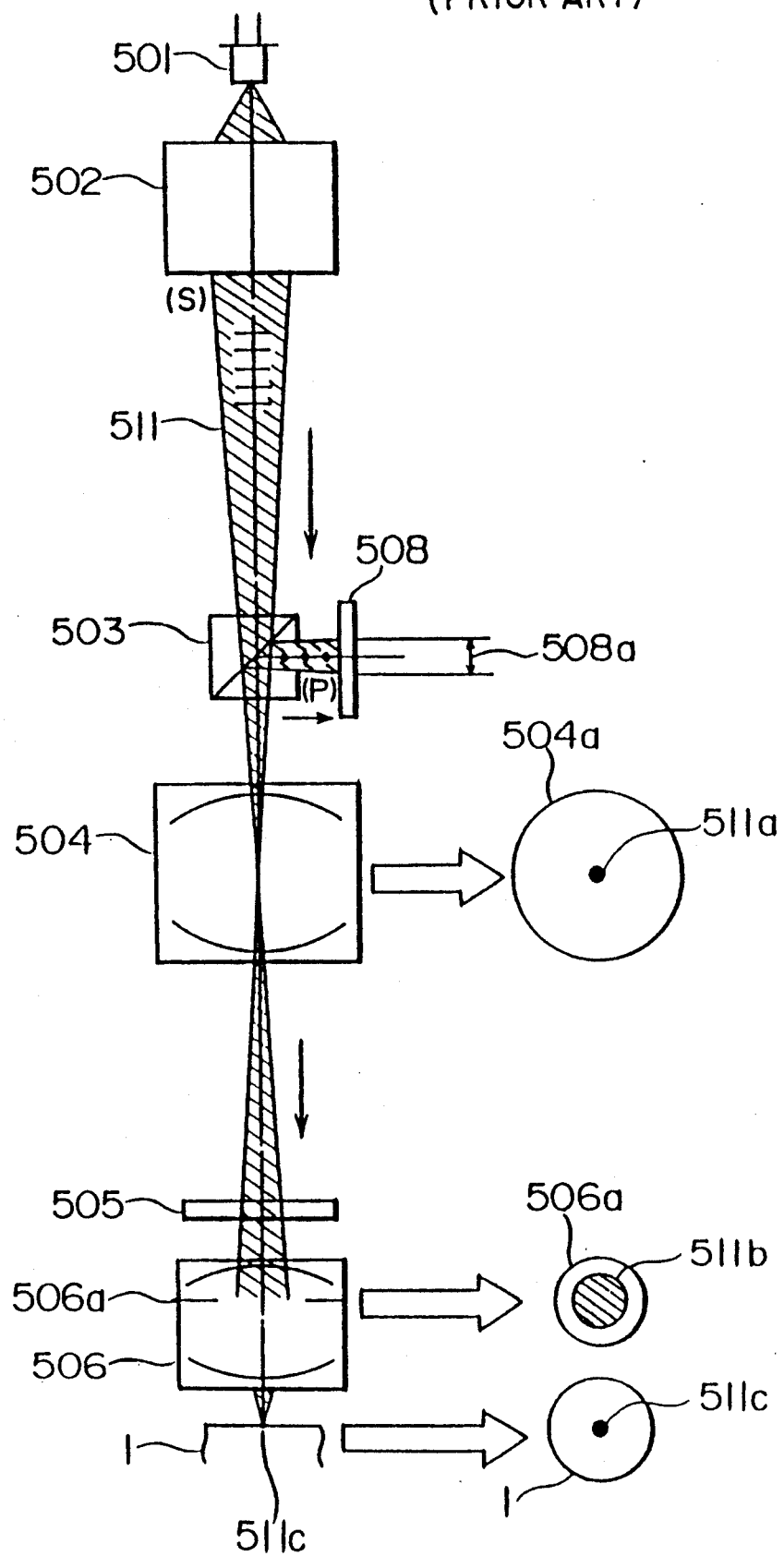
FIG. 33 is a scheme illustrating the state of the light reflected by the sample in the sample in the device indicated in FIG. 32.
Figure 34:
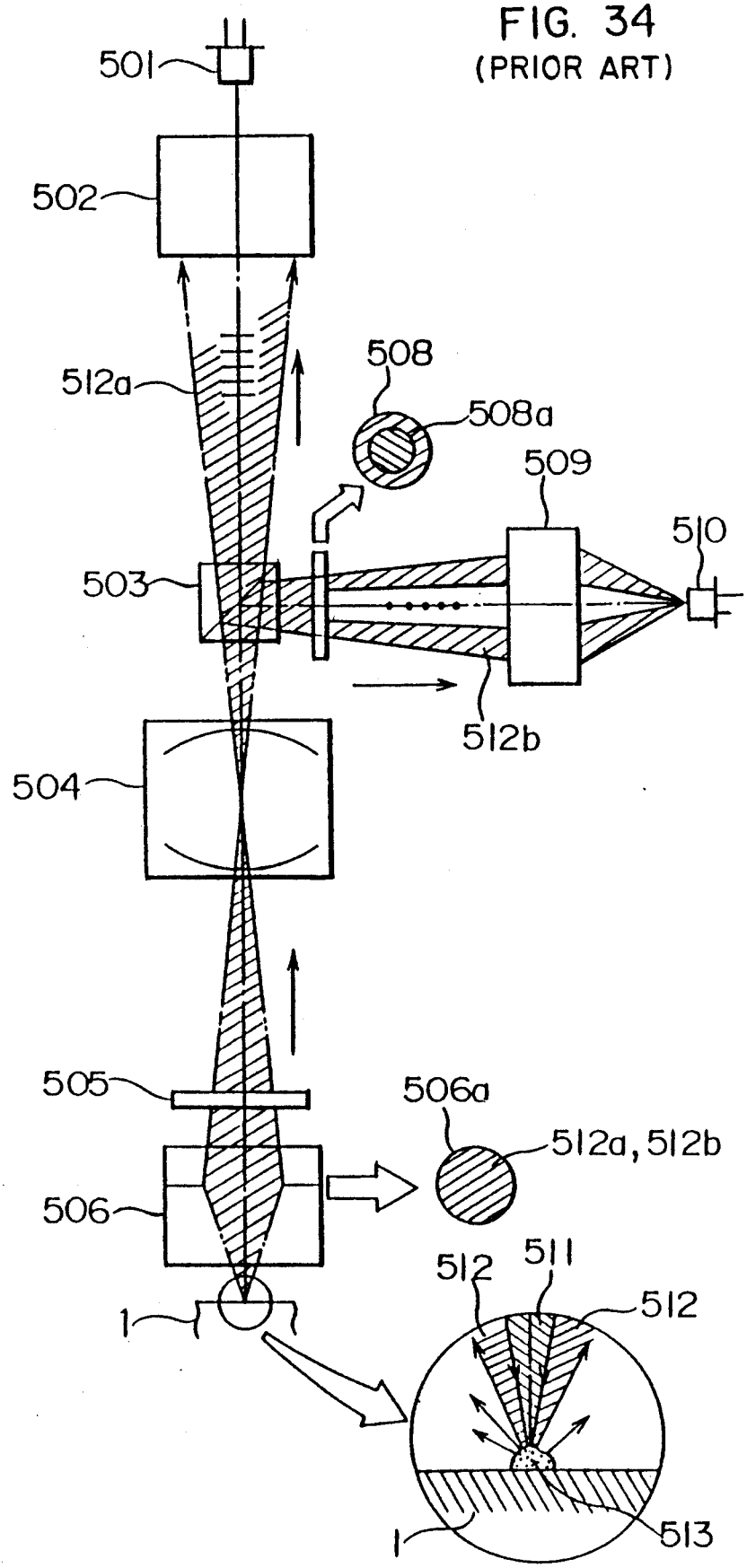
FIG. 34 is a scheme illustrating the state of the light scattered by the foreign matter in the device indicated in FIG. 32.

FIG. 31 shows a detecting signal processing circuit from 523 to 525 indicated in FIG. 30, in the case where parallel output type elements 510a and 517 are used.

FIG. 30 is a block diagram illustrating the construction of the foreign matter detecting device; FIGS. 29A to 29C are schemes for explaining the optical path of the light scattered by the foreign matter by the downward illumination; and FIG. 27 is a scheme for explaining the optical path of the light scattered by the foreign matter by the oblique illumination.

As explained above, according to the present invention, it is possible to simplify the mechanism for scanning the sample mechanically. Further, according to the present invention, it is possible to detect foreign matter with a high sensitivity.

As explained in the summary of the present invention and the preferred embodiments thereof, according to the present invention it is possible to detect considerably small particles of foreign matter with a high sensitivity.

We claim:

1. A method for detecting foreign matter on a sample comprising the steps of:
   illuminating the sample in a stripe-shaped illumination region with illuminating light having a high directivity to create reflected light using an illuminating apparatus;
   intercepting selected portions of the reflected light reflected by a regular pattern on the sample using a light intercepting apparatus for intercepting said portions of the reflected light and allowing to pass through the non-intercepted portions of said reflected light;
   leading the non-intercepted reflected light, reflected by the sample, which has passed through the light intercepting means, to a photo-electric converting device having a detecting region corresponding to said stripe-shaped illumination region provided within a photo-detector; and,
   detecting the non-intercepted reflected light by said photo-electric converting device.

2. The method for detecting foreign matter according to claim 1, wherein said sample is a semiconductor wafer.

3. The method for detecting foreign matter according to claim 1, wherein said sample is a magnetic disk.

4. The method for detecting foreign matter according to claim 1, further comprising:
   illuminating the sample obliquely, in a stripe-shaped region with illuminating light having a high directivity, in a direction forming a predetermined angle with a plane of the sample in accordance with a principal group of straight line edges comprising the regular pattern on a sample;
   intercepting regular reflected light reflected by remaining straight line edges not the principal straight lie edges, comprising a secondary pattern on the sample, by a light intercepting device for intercepting the regular reflected light in a spatial frequency region within a detecting optical system disposed so as to correspond to said striped-shaped illumination region to detect the non-intercepted reflected light reflected by the foreign matter on said sample; and,
   detecting the non-intercepted reflected light reflected by the foreign matter on the sample, the non-intercepted reflected light having passed through the light intercepting means, through said detecting optical system.

5. The method for detecting foreign matter according to claim 4, further comprising:
   implementing the predetermined angle for which said regular reflected light, reflected by said principal group of straight line edges do not enter said detecting optical system.

6. The method for detecting foreign matter according to claim 4, further comprising determining a numerical aperture value of said detecting optical system so that said regular reflected light reflected by said principal straight line edges do not enter the detecting optical system.

7. The method for detecting foreign matter according to claim 4, wherein said predetermined angle is about 45°.

8. The method for detecting foreign matter according to claim 1, further comprising:
   illuminating obliquely the sample in a stripe-shaped illumination region with linearly polarized illumination light to create the reflected light;
   intercepting the reflected light with a polarizing plate disposed in a predetermined restricted region in a spacial frequency region within a detecting optical system disposed adjacent said stripe-shaped illumination region to detect scattering light reflected by said sample; and,
   detecting a foreign matter reflected light reflected by the foreign matter on the sample, the foreign matter reflected light having passed through said light intercepting apparatus and through said detecting optical system, by selectively intercepting a polarization component in a predetermined spacial frequency region of the scattered light reflected by the sample using said light intercepting apparatus.

9. The method for detecting foreign matter according to claim 1, further comprising:
   illuminating obliquely the sample in a stripe-shaped region with linearly polarized illumination light having a high directivity to create the reflected light;
   forming a light intercepting apparatus for intercepting the reflected light by disposing an optical element for varying a polarization state of the reflected light in a predetermined restricted region in a spacial frequency region within a detecting optical system disposed adjacent said illumination region for detecting the reflected light scattered by said sample; and,
   detecting foreign matter reflected light reflected by the foreign matter on the sample, which has passed through said intercepting means, through said detecting optical system, by selectively intercepting a predetermined polarization component in a predetermined spacial frequency region in the reflected light scattered by the sample using said light intercepting apparatus.

10. The method for detecting foreign matter according to claim 1, further comprising:
    effecting strip-shaped downward illumination on the sample in a stripe-shaped region by means of a downward illuminating system to create reflected light;
    collecting scattered light coming from said stripe-shaped downward illumination region by means of a detecting optical system; and,
    receiving selected portions of the reflected light by a one-dimensional solid state imaging element, whose arrangement is directed in a direction of said stripe-shaped region, which light is transformed into image signals, and detecting the foreign matter on the sample by said image signals.

11. The method for detecting foreign matter according to claim 1, further comprising:
    effecting stripe-shaped downward illumination on the sample in a strip-shaped region by means of a downward illuminating system to create reflected light;
    intercepting a 0-th order diffraction light in the reflected light coming from said stripe-shaped illumination region using said light intercepting apparatus;
    collecting the intercepted reflected light by means of a detecting optical system;
    receiving selected portions of the reflected light by a one-dimensional solid state imaging element arranged in a direction of said stripe-shaped region, which received light is transformed into image signals; and, detecting the foreign matter on the sample by said image signals.

12. The method for detecting foreign matter according to claim 1, further comprising:
   effecting stripe-shaped downward illumination on the sample in a stripe-shaped region with light polarized in a predetermined direction by means of a downward illuminating system to generate scattered light;
   collecting the scattered light coming from said stripe-shaped region;
   separating the scattered light into a first linear polarization component and a second linear polarization component by means of polarization separating device;
   intercepting a 0-th order diffraction light of the scattered light by means of a light intercepting device;
   receiving selected portions of the scattered light by a one-dimensional solid state imaging element in a photo-detector arranged in a direction of said stripe-shaped region, which received light is transformed into image signals; and,
   detecting the foreign matter on the sample based on an image signal obtained by adding said image signals by means of an adder.

13. The method for detecting foreign matter for detecting foreign particles of foreign matter on a sample according to claim 1 further comprising:
   obliquely illuminating a stripe-shaped sample region on the sample;
   providing a mask at a position of an image of a Fourier transformation plane of an objective lens adjacent said stripe-shaped sample region, which mask includes a ½ wave plate for partially intercepting incident light, so that resolution at the imaging plane formed by scattered light coming from said stripe-shaped sample region is lowered to detect said particles of foreign matter by an image smoothing method, by which said scattered light is detected while smoothing pixels.

14. A device for detecting foreign matter on a sample, the device comprising:
   illuminating means for illuminating the sample in a stripe-shaped region with light having a high directivity;
   light intercepting means for intercepting select portions of sample reflected light reflected by the sample; and,
   a photo-detector provided with photo-electric converting means for detecting the sample reflected light reflected by the sample, which has passed through said light intercepting means, the photo-detector means having a detecting region shape corresponding to said stripe-shaped illumination region shape.

15. The device for detecting foreign matter according to claim 14, wherein said sample is a semiconductor wafer.

16. The device for detecting foreign matter according to claim 14, wherein said sample is a magnetic disk.

17. The device for detecting foreign matter according to claim 14, further comprising:
   illuminating means for illuminating obliquely the sample in a stripe-shaped illumination region with linearly polarized illumination light having a high directivity;
   a detecting optical system disposed adjacent said illumination region for detecting light scattered by said sample;
   light intercepting means for selectively intercepting a predetermined polarization component of foreign matter reflected light reflected by the foreign matter by disposing a polarizing plate in a predetermined restricted region in a spatial frequency region within said detecting optical system; and,
   a photo-detector means for detecting the foreign matter reflected light reflected by the foreign matter on the sample, the foreign matter reflected light having passed through said light intercepting means, through said detecting optical system.

18. The device for detecting foreign matter according to claim 17, wherein said linearly polarized illumination light is monochromatic light.

19. The device for detecting foreign matter according to claim 14, comprising:
   illuminating means for illuminating obliquely the sample in a stripe-shaped region with linearly polarized illumination light having a high directivity;
   a detecting optical system disposed adjacent said illumination region for detecting the light scattered by said sample;
   light intercepting means for selectively intercepting a predetermined polarization component of the sample reflected light reflected by the sample using an optical element for varying a polarization state of the sample reflected light in a predetermined restricted region, the optical element being disposed in a spatial frequency region within said detecting optical system; and,
   a photo-detector means for detecting foreign matter reflected light reflected by the foreign matter on the sample, the foreign matter reflected light having passed through said intercepting means.

20. The device for detecting foreign matter according to claim 19, wherein said optical element for varying the polarization state of the sample reflected light comprises a liquid crystal.

21. The device for detecting foreign matter according to claim 19, wherein said optical element for varying the polarization state of the sample reflected light comprises a wave plate.

22. The device for detecting foreign matter according to claim 14 further comprising:
   an illuminating optical system for illuminating the sample with light;
   a focusing lens system for focusing the sample reflected light reflected by the sample to obtain a focussed light;
   a plurality of detecting optical systems for separating the focussed light obtained by said focusing lens system into separated light, each detecting optical system including a one-dimensional solid state imaging element for converting the separated light into electric signals;
   driving means for driving said one-dimensional solid state imaging element in each of said detecting optical systems in order to output the electric signals synchronously, corresponding to pixels of said one-dimensional solid state imaging element;
   adding means for adding said electric signals outputted synchronously by said driving means to derive an added signal;
   quantizing means for quantizing the added signal to derive a quantized signal; and, detecting means for detecting the foreign matter based on the quantized signal.

23. The device for detecting foreign matter according to claim 22, wherein said one-dimensional solid state imaging element is a serial output type imaging element.

24. The device for detecting foreign matter according to claim 22, wherein said one-dimensional solid state imaging element is a parallel output type imaging element.

25. The device for detecting foreign matter according to claim 14, further comprising:
a downward illuminating optical system effecting stripe-shaped downward illumination on the sample in a stripe-shaped region;
light intercepting means for intercepting 0-th order diffraction light coming from said stripe-shaped downward illumination region illuminated by said downward illuminating optical system and for not intercepting passed diffraction light;
a photo-detector with a one-dimensional solid state imaging element arranged to correspond to the stripe-shaped region for receiving the passed diffraction light, which is not intercepted by said light intercepting means, to convert the passed diffraction light into image signals; and,
detecting means for detecting the foreign matter on the sample based on said image signals.

26. The device for detecting foreign matter according to claim 25, further comprising oblique illuminating means for obliquely illuminating said stripe-shaped downward illumination region on the sample in a stripe-shaped region.

27. The device for detecting foreign matter according to claim 14, comprising:
a downward illuminating system for illuminating the sample in a stripe-shaped region with light linearly polarized in a predetermined direction;
polarization separating means for separating the sample reflected light reflected from the sample and having various polarizations into reflected light parts, depending on polarization orientation;
light intercepting means for interception 0-th order diffraction light for each of said reflected light parts and for not intercepting passed diffraction light;
a plurality of photo-detectors for receiving the passed diffraction light, which is not intercepted by said light intercepting means and for transforming the passed diffraction light into an image signal; and,
detecting means for detecting the foreign matter on the sample based on said image signal obtained by each of said plurality of photo-detectors.

28. The device for detecting foreign matter according to claim 27, further comprising oblique illuminating means for obliquely illuminating said stripe-shaped downward illumination region on the sample in a stripe-shaped region.

29. The device for detecting foreign matter according to claim 14, comprising:
illuminating means for obliquely illuminating a stripe-shaped small region on the sample with linearly polarized light;
an objective lens located adjacent said stripe-shaped small region;
image smoothing means for reducing resolution at an imaging plane formed by scattered light coming from said stripe-shaped small region to smooth pixels by using a mask, the mask including a ½ wave plate intercepting partially incident light at the position of the image of a Fourier transformation plane of the objective lens; and,
light detecting means for detecting said scattered light through said image smoothing means.

30. A device for detecting foreign matter on a sample comprising:
illuminating means for illuminating obliquely the sample in a rectangular illumination region with light having a high directivity in a direction forming a predetermined angle with a plane of the sample in accordance with a principal group of straight line edges forming a principal pattern on the sample;
a detecting optical system disposed adjacent said illumination region for detecting reflected light reflected by said sample;
light intercepting means for intercepting regular reflected light scattered regularly by secondary straight line edges constituting a secondary pattern on the sample, the light intercepting means being disposed in a spatial frequency region within said detecting optical system; and,
a photo-detector means for detecting the foreign matter on the sample in accordance with an image signal obtained by detecting an image of scattering light reflected by the foreign matter, the scattering light having passed through said light intercepting means, through said light detecting optical system.

31. The device for detecting foreign matter according to claim 30, wherein the predetermined angle is an angle, for which principal pattern light reflected by said principal group of straight line edges does not enter said detecting optical system.

32. The device for detecting foreign matter according to claim 30, wherein said detecting optical system provides an objective lens determined by a numerical aperture value so that regular reflected light reflected by said principal straight line edges do not enter said detecting optical system.

33. The device for detecting foreign matter according to claim 30, wherein said predetermined angle is about 45°.

* * * * *

UNITED STATES PATENT AND TRADEMARK OFFICE
CERTIFICATE OF CORRECTION

PATENT NO. : 5,046,847

DATED : September 10, 1991

INVENTOR(S) : Toshihiko Nakata, et al.

It is certified that error appears in the above-identified patent and that said Letters Patent is hereby corrected as shown below:

Title Page: ITEM [75]
 Inventor: The third inventor's name should be Yoshihiko Yamauchi Claim 4, column 29, line 36, delete "lie" and insert therefor --line--.

Claim 11, column 30, line 55, delete "strip-shaped" and insert therefor --stripe-shaped--.

Signed and Sealed this

Sixteenth Day of February, 1993

*Attest:*

STEPHEN G. KUNIN

*Attesting Officer*     *Acting Commissioner of Patents and Trademarks*